(12) United States Patent
Park et al.

(10) Patent No.: US 10,967,073 B2
(45) Date of Patent: Apr. 6, 2021

(54) GLUCOCEREBROSIDASE GENE THERAPY FOR PARKINSON'S DISEASE

(71) Applicants: Shire Human Genetic Therapies, Inc., Lexington, MA (US); The McLean Hospital Corporation, Belmont, MA (US)

(72) Inventors: Yung Hee Park, Lexington, MA (US); Ole Isacson, Belmont, MA (US)

(73) Assignees: The McLean Hospital Corporation, Belmont, MA (US); Shire Human Genetic Therapies, Inc., Lexington, MA (US)

( * ) Notice: Subject to any disclaimer, the term of this patent is extended or adjusted under 35 U.S.C. 154(b) by 45 days.

(21) Appl. No.: 15/572,171

(22) PCT Filed: May 6, 2016

(86) PCT No.: PCT/US2016/031223
§ 371 (c)(1),
(2) Date: Nov. 7, 2017

(87) PCT Pub. No.: WO2016/179497
PCT Pub. Date: Nov. 10, 2016

(65) Prior Publication Data
US 2018/0147300 A1    May 31, 2018

Related U.S. Application Data

(60) Provisional application No. 62/158,244, filed on May 7, 2015.

(51) Int. Cl.
| | |
|---|---|
| A61K 48/00 | (2006.01) |
| A61K 38/47 | (2006.01) |
| C12N 9/24 | (2006.01) |
| A61K 35/76 | (2015.01) |
| A61P 25/16 | (2006.01) |
| A61K 9/00 | (2006.01) |
| C12N 15/86 | (2006.01) |

(52) U.S. Cl.
CPC ........ *A61K 48/0058* (2013.01); *A61K 9/0085* (2013.01); *A61K 35/76* (2013.01); *A61K 38/47* (2013.01); *A61P 25/16* (2018.01); *C12N 9/2402* (2013.01); *C12N 9/2405* (2013.01); *C12N 15/86* (2013.01); *C12Y 302/01045* (2013.01); *A01K 2227/105* (2013.01); *A01K 2267/0356* (2013.01); *C12N 2750/14143* (2013.01); *C12N 2750/14171* (2013.01)

(58) Field of Classification Search
CPC .. A61K 48/0058; A61K 35/76; A61K 9/0085; A61K 38/47; C12N 9/2402; C12N 9/2405; C12N 15/86; C12N 2750/14171; C12N 2750/14143; A01K 2267/0356; A01K 2227/105; C12Y 302/01045

USPC .......... 514/44 R; 424/199.1; 435/320.1, 456
See application file for complete search history.

(56) References Cited

U.S. PATENT DOCUMENTS

| | | | |
|---|---|---|---|
| 5,658,776 | A | 8/1997 | Flotte et al. |
| 5,962,313 | A | 10/1999 | Podsakoff et al. |
| 6,180,613 | B1 | 1/2001 | Kaplitt et al. |
| 6,270,989 | B1 | 8/2001 | Treco et al. |
| 6,335,011 | B1 | 1/2002 | Podsakoff et al. |
| 6,503,888 | B1 | 1/2003 | Kaplitt et al. |
| 6,582,692 | B1 | 6/2003 | Podsakoff et al. |
| 6,667,174 | B2 | 12/2003 | Yew |
| 6,696,272 | B1 | 2/2004 | Mahuran et al. |
| 6,797,265 | B2 | 9/2004 | Amalfitano et al. |
| 7,452,716 | B2 | 11/2008 | Yew |
| 8,454,954 | B2 | 6/2013 | Schlossmacher et al. |
| 8,628,956 | B2 | 1/2014 | Koh et al. |
| 2011/0038851 | A1 | 2/2011 | Schlossmacher et al. |
| 2012/0003202 | A1 | 1/2012 | Calias et al. |
| 2013/0177549 | A1 | 7/2013 | Schlossmacher et al. |
| 2013/0295071 | A1 | 11/2013 | Salamat-Miller et al. |
| 2013/0295077 | A1 | 11/2013 | Concino et al. |

FOREIGN PATENT DOCUMENTS

| | | |
|---|---|---|
| EP | 2154969 A2 | 2/2010 |
| WO | WO-95/00655 A1 | 1/1995 |
| WO | WO-95/11984 A2 | 5/1995 |
| WO | WO-95/27071 A2 | 10/1995 |
| WO | WO-2005/039643 A2 | 5/2005 |
| WO | WO 2006/133446   * | 12/2006 |
| WO | WO-2007/150064 A2 | 12/2007 |
| WO | WO 2014/071282   * | 5/2014 |
| WO | WO-2014/071282 A1 | 5/2014 |

(Continued)

OTHER PUBLICATIONS

Husain et al. (2009) Gene Ther., vol. 16(17), 927-932.*

(Continued)

*Primary Examiner* — Anne Marie S Wehbe
(74) *Attorney, Agent, or Firm* — Charles E. Lyon; David E. Shore; Choate, Hall & Stewart LLP

(57) ABSTRACT

The present invention is directed, in part, to the treatment of a subject having a neurodegenerative disorder, such as Parkinson's disease (PD), by providing glucocerebrosidase enzyme. The enzyme may be provided, e.g., through gene therapy or by administration of a glucocerebrosidase protein. Accordingly, the present invention encompasses glucocerebrosidase nucleic acids or proteins for use in the treatment of PD or other neurodegenerative disorders.

14 Claims, 10 Drawing Sheets
Specification includes a Sequence Listing.

(56) References Cited

FOREIGN PATENT DOCUMENTS

| WO | WO-2015/060722 A1 | 4/2015 |
| WO | WO-2016/179497 A1 | 11/2016 |

OTHER PUBLICATIONS

Burger et al. (2004) Mol. Ther., vol. 10(2), 302-317.*
Wan et al. (2012) PLoS One, vol. 7(6), e38545,doi:10.1371/journal.pone. 0038545, pp. 1-14.*
Yaguchi et al. (2013) Human Gene Therapy, vol. 24, 333-344).*
Bourdenx et al. (2014) Frontiers in Molecular Neuroscience, vol. 7, Article 50, doi:10.3389/fnmol.2014.0050, pp. 1-8.*
Beutler, E. et al. Polymorphisms in the human glucocerebrosidase gene, *Genomics*, 12(4): 795-800 (1992).
Beutler, E. et al., Glucocerebrosidase mutations in Gaucher disease, Molecular Medicine 1(1): 82-92 (1994).
Brumshtein, B. et al., Characterization of gene-activated human acid-beta-glucosidase: crystal structure, glycan composition, and internalization into macrophages, Glycobiology, 20(1): 24-32 (2010).
Burrow, T. A. and Leslie, N. D., Review of the use of idursulfase in the treatment of mucopolysaccharidosis II, Biologics: Targets & Therapy, 2(2): 311-320 (2008).
Calias, P. et al, CNS penetration of intrathecal-lumbar idursulfase in the monkey, dog and mouse: implications for neurological outcomes of lysosomal storage disorder, PLOS One, 7(1): e30341 (2012).
Daher, J.P.L. et al, Neurodegenerative phenotypes in an A53T α-synuclein trangenic mouse model are independent of LRRK2, Human Molecular genetics, 21(11): 2420-2431 (2012).
Gao, G-P. et al, Novel adeno-associated viruses from rhesus monkeys as vectors for human gene therapy, *PNAS* 99(18):11854-11859 (2002).
GenBank Accession No. AH006907.2 (J03059), *Homo sapiens* chromosome 1 glucocerebrosidase (GCB) gene, complete cds, (2016), <https://www.ncbi.nlm.nih.gov/nuccore/AH006907>. Retrieved on Jul. 11, 2018.
GenBank Accession No. NC_000069, (Jun. 22, 2016), Mus musculus strain C57BL/6J chromosome 3, GRCm38.p4 C57BLJ6J, <https://www.ncbi.nlm.nih.gov/nuccore/NC_000069>>. (Retrieved Jul. 13, 2018).
GenBank Accession No. NM_001077411, (2018), Mus musculus glucosidase, beta, acid (Gba), transcript variant 2, mRNA, <<https://www.ncbi.nlm.nih.gov/nuccore/NM_001077411>>. Retrieved on Jul. 13, 2018.
GenBank Accession No. M16328, Human glucocerebrosidase mRNA, complete cds, first referenced Apr. 27, 1993, <https:www.ncbi.nlm.nih.gov/nuccore/M16328.1/>. Retrieved on Jul. 11, 2018.
Gene ID No. 2629, GBA glucosylcermidase beta[*Homo sapiens*], updated on Jul. 8, 2018, <https://www.ncbi.nlm.nih.gov/gene/2629?report=full_report&formal=text>., Retrieved on Jul. 11, 2018.
Hermonat, P.L. and Muzyczka, N., Use of adeno-associated virus as a mammalian DNA cloning vector: transduction of neomycin resistance into mammalian tissue culture cells, PNAS, 81(10) :6466-6470 (1984).
International Preliminary Report on Patentability for PCT/US2016/031223 (Glucocerebrosidase Gene Therapy for Parkinson'S Disease, filed May 6, 2016), issued by WIPO, 9 pages (Nov. 7, 2017).
International Search Report for PCT/US2016/031223, 6 pages (dated Sep. 28, 2016).
Lebkowski, J.S. et al. Adeno-associated virus: a vector system for efficient introduction and integration of DNA into a variety of mammalian cell types, Mol. Cell. Biol. 8:3988-3996 (1988).
Lesage, S. et al, Large-scale screening of the Gaucher's disease-related glucocerebrosidase gene in Europeans with Parkinson's disease, Human Molecular Genetics 20(1):202-10 (2011).
Manfredsson, F.P. et al, AAV9: a potential blood-brain barrier buster, *Molecular Theraphy* 17(3): 403-405 (2009).
National Institute of Neurological Disorders and Stroke (NINDS), Clinical Trial NCT01621581, AAV2-GDNF for Advanced Parkinson's Disease, (2012), <https://clinicaltrials.gov/ct2/show/NCT01621581>. Retrieved on Jul. 11, 2018.
Rocha, E. et al., Glucocerebrosidase gene therapy prevents α-synucleinopathy of midbrain dopamine neurons, Neurobiology of Disease, 82:495-503 (2015).
Sardi, S. et al., CNS expression of glucocerebrosidase corrects α-synuclein pathology and memory in a mouse model of Gaucher-related synucleinopathy, PNAS, 108(29):12101-12106 (2011).
Sardi, S. P. et al, Augmenting CNS glucocerebrosidase activity as a therapeutic strategy for parkinsonism and other Gaucher-related synucleinopathies, PNAS, 110(9): 3537-3542 (2013).
UnitProtKB-P04062 (GLCM_HUMAN), <<https://www.uniprot.org/uniprot/P04062>>. Retrieved Jul. 13, 2018.
Viral Vectors for Gene Therapy: Methods and Protocols, Methods in Molecular Medicine, Edited by Curtis A. Machida, Humana Press, 606 pages (2003).
Voyager Therapeutics, Clinical Trial NCT01973543, Safety Study of AADC Gene Therapy (VY-AADC01) for Parkinson's Disease (AADC), (2013), <https://clinicaltrials.gov/ct2/show/NCT019753543>. Retrieved on Jul. 11, 2018.
Voznyi, Y.V. et al., a fluorimetric enzyme assay for the diagnosis of MPS II (Hunter disease), J. Inherit. Metab. Dis., 24: 675-680 (2001).
Written Opinion for PCT/US2016/031223, 9 pages (dated Sep. 28, 2016).

\* cited by examiner

SUBSTANTIA NIGRA

A

C

E

STRIATUM

B

D

F

GLUCOCEREBROSIDASE GENE THERAPY FOR PARKINSON'S DISEASE

CROSS-REFERENCE TO RELATED APPLICATIONS

This application is a National Stage Entry of International Application No. PCT/US2016/031223, filed May 6, 2016, which claims the benefit of U.S. Provisional Application No. 62/158,244, filed May 7, 2015, the contents of each of which is hereby incorporated by reference in its entirety.

BACKGROUND

Degenerative neurological diseases affect millions of individuals world-wide. Parkinson's disease (PD) is a progressive degenerative condition that involves the central nervous system (CNS). Cellular characteristics of PD can include degeneration of dopaminergic neurons, e.g., in the substantia nigra, a portion of the brain thought to participate in the control of voluntary movement. Clinical characteristics of PD can include increased stiffness of voluntary skeletal muscles, muscle rigidity, tremors, shaking, a slowness of physical movement (bradykinesia), impaired balance, difficulty walking (e.g., festination, characterized by rapid shuffling steps and a forward-flexed posture), altered gait, impaired coordination, or loss of physical movement (akinesia), amongst other symptoms. Depression, sleep disturbance, dizziness, stooped posture, dementia, and problems with speech (e.g., dysarthria), breathing (e.g., dyspnea), and swallowing (e.g., dysphagia) can also occur. Worldwide, the prevalence of PD has been estimated to be as high as 1% for individuals over the age of 60. Although certain treatments are available, such as drugs and physical therapy, PD is a progressive disorder and symptoms typically continue to worsen throughout life. In many cases, symptoms escalate with time and ultimately result in death. There is a need in the art for further means of treating neurodegenerative disorders such as PD.

SUMMARY OF THE INVENTION

The present invention provides improved methods for the treatment of neurodegenerative conditions such as Parkinson's disease (PD). The present invention includes, among other things, the administration of glucocerebrosidase nucleic acids for the treatment of PD. The treatments described herein are based, in part, on the discovery that glucocerebrosidase nucleic acids effectively treat neurodegenerative symptoms of PD in well-established mouse models of that condition. For example, the present disclosure relates, among other findings, that administration of glucocerebrosidase nucleic acids rescues dopaminergic neurons from α-synuclein-induced degeneration. Moreover, the present disclosure also relates that multiple biomarkers of PD are improved by administration of glucocerebrosidase nucleic acids.

At least one aspect of the present invention is a method of treating Parkinson's disease (PD), the method including administering to a subject in need thereof a nucleic acid encoding a glucocerebrosidase protein. In some embodiments, the nucleic acid includes a nucleotide sequence having at least 80% identity, at least 90% identity, or at least 95% identity to SEQ ID NO.: 1 or SEQ ID NO.: 2. In some embodiments, the glucocerebrosidase protein includes an amino acid sequence having at least 80% identity to SEQ ID No.: 3, SEQ ID No.: 4, or SEQ ID NO.: 5. In various embodiments of such methods, the nucleotide sequence can have at least 90% identity or at least 95% identity to SEQ ID No.: 3, SEQ ID No.: 4, or SEQ ID NO.: 5.

In various embodiments, the nucleic acid is present in a vector for gene therapy, such as an AAV vector. In some instances, the AAV vector is selected from the group consisting of AAV1, AAV2, AAV3, AAV4, AAV5, AAV6, AAV7, AAV8, and AAV9. In certain instances, the vector is a pseudotyped vector capable of infecting a human cell, e.g., a pseudotyped vector selected from the group consisting of AAV2/1, AAV2/2, AAV2/5, AAV2/6, AAV2/7, AAV2/8, and AAV2/9.

In various embodiments, the administration of the nucleic acid increases the amount and/or activity of glucocerebrosidase protein in one or more brain tissues, e.g., an increase of by at least about 10%, 20%, 30%, 40%, 50%, 60%, 70%, 80%, 90%, or 100%. Such an increase can be determined, e.g., by measuring the amount and/or activity of glucocerebrosidase protein in a sample of saliva, serum, or cerebrospinal fluid from the subject. In some instances, the administration of the nucleic acid decreases the amount of glucosylceramide in one or more brain tissues, which can be determined, e.g., by measuring the amount of glucosylceramide in a sample of saliva, serum, or cerebrospinal fluid from the subject. In particular instances, the decrease in the amount of glucosylceramide is correlated with an increase in the amount and/or activity of glucocerebrosidase protein in one or more brain tissues. In some instances, the administration of the nucleic acid decreases the amount of glucosylsphingosine in one or more brain tissues, which can be determined, e.g., by measuring the amount of glucosylsphingosine in a sample of saliva, serum, or cerebrospinal fluid from the subject. In particular instances, the decrease in the amount of glucosylsphingosine is correlated with an increase in the amount and/or activity of glucocerebrosidase protein in one or more brain tissues.

In various embodiments of the present invention, a method as described herein decreases the size or amount of α-synuclein aggregates in one or more brain tissues, which can be determined, e.g., by measuring the size or amount of α-synuclein aggregates in a sample of saliva, serum, or cerebrospinal fluid from the subject. In some instances, the decrease is by at least about 10%, 20%, 30%, 40%, 50%, 60%, 70%, 80%, 90%, or 100%.

In various embodiments of the present invention, a method as described herein increases the amount of LC3-II in one or more brain tissues. In some instances, the increase is by at least about 10%, 20%, 30%, 40%, 50%, 60%, 70%, 80%, 90%, or 100%.

In various embodiments of the present invention, a method as described herein increases the amount of any of one or more of beclin-1, LAMP-2A, and ceramide in one or more brain tissues. In some instances, the increase is by at least about 10%, 20%, 30%, 40%, 50%, 60%, 70%, 80%, 90%, or 100%.

In various embodiments of the present invention, a method as described herein increases the amount or concentration of ubiquitin-like protein p62 in one or more brain tissues. In some instances, the increase is by at least about 10%, 20%, 30%, 40%, 50%, 60%, 70%, 80%, 90%, or 100%.

In various embodiments of the present invention, the administration of the nucleic acid treats one or more symptoms associated with PD selected from degeneration of dopaminergic neurons, stiffness of voluntary skeletal muscles, muscle rigidity, tremors, bradykinesia, impaired balance, difficulty walking, impaired coordination, akinesia, depression, decreased use or presence of facial expressions, apathy, anxiety, cravings, binge eating, hypersexuality, pathological gambling, hallucinations, delusions, difficulty sleeping, daytime drowsiness, insomnia, dizziness, stooped posture, dementia, dysarthria, dyspnea, dysphagia, loss of dopaminergic innervation, loss of motor activity, accumulation of α-synuclein, accumulation of Lewy bodies, difficulty planning movements, difficulty initiating movement, difficulty executing movements, difficulty in the performance of sequential or simultaneous movements, muscle spasticity, progressive weakness, muscle atrophy, difficulty alternating movements between both hands or both feet, balance impairment, postural instability, cognitive executive dysfunction, cognitive difficulty in planning, cognitive difficulty in flexibility, cognitive difficulty in abstract thinking, cognitive difficulty in rule acquisition, cognitive difficulty in initiating appropriate actions, cognitive difficulty in inhibiting inappropriate actions, cognitive difficulty in differentiating relevant from irrelevant sensory information, cognitive difficulty with attention, difficulty in speed of cognition, difficulty with memory, difficulty with recall, difficulty with visuospatial perception, difficulty with facial recognition, decreased blink rate, dry eyes, deficient ocular pursuit, saccadic movements, difficulties in directing one's gaze upward, blurred vision, double vision, impaired sense of smell, sensation of pain, sensation of paresthesia, orthostatic hypotension, oily skin, excessive sweating, urinary incontinence, altered sexual function, constipation, gastric dysmotility, tendency toward choking, pneumonia, tendency toward falling, requirement for care, or requirement for institutionalization.

In various embodiments, the administration of the nucleic acid treats degeneration of neurons, e.g., degeneration of dopaminergic neurons. In particular instances, the treatment of the degeneration includes a decrease in the number or severity of one or more of swollen axons, bulging axons, and axons that are both swollen and bulging. The treatment of the degeneration can include an increase in macroautophagy.

In various embodiments of the present invention, the administration is intraparenchymal, intracerebral, intraventricular cerebral (ICV), intrathecal. In particular embodiments, the administration is intrathecal, e.g., where the intrathecal administration includes IT-Lumbar.

Another aspect of the present invention includes a gene therapy vector for the treatment of Parkinson's disease, the gene therapy vector including a nucleic acid encoding a glucocerebrosidase protein operably linked to a promoter capable of expression in neurons. In particular instances the vector is an AAV2/5 vector. In some embodiments, the nucleic acid includes a nucleotide sequence having at least 80% identity to SEQ ID NO.: 1 or SEQ ID NO.: 2. In some embodiments, the glucocerebrosidase protein includes an amino acid sequence having at least 80% identity to SEQ ID No.: 3, SEQ ID No.: 4, or SEQ ID NO.: 5. In some embodiments, the promoter is a synapsin promoter, nestin promoter, or neuron specific enolase promoter. In some embodiments, the promoter is a PGK promoter or DRD1/DRD2 poromoter.

Definitions

In order for the present invention to be more readily understood, certain terms are first defined below. Additional definitions for the following terms and other terms are set forth throughout the specification.

Administration: As used herein, the term "administration" refers to the delivery or application of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal. "Gene therapy" refers to any treatment including the direct or indirect administration of a nucleic acid to a subject. In particular instances, a protein of therapeutic value is expressed from an administered nucleic acid.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. Biological activity can also be determined by in vitro assays (for example, in vitro enzymatic assays). In particular embodiments, where a protein or polypeptide is biologically active, a portion of that protein or polypeptide that shares at least one biological activity of the protein or polypeptide is typically referred to as a "biologically active" portion. In some embodiments, a protein is produced and/or purified from a cell culture system, which displays biologically activity when administered to a subject.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control. In some embodiments, the control may be a "reference control", which is a sample used for comparison with a test sample, to look for differences or for the purposes of characterization.

Concentration: As used herein, the term "concentration" refers to a measure indicative of amount of substance in a volume. Typically, concentration is measured by a numerical value with physical units of mass*volume$^{-1}$, such as molar and millimolar. It is to be understood that the determination of an "amount" is typically commensurate with or equivalent to the determination of a "concentration."

Enzyme: As used herein, the term "enzyme" refers to any protein capable of producing changes in a biological substance by catalytic action.

Enzyme activity: As used herein, the term "enzyme activity", "enzymatic activity" or grammatical equivalent, refers to the general catalytic properties of an enzyme.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Various other sequence alignment programs are available and can be used to determine sequence identity such as, for example, Clustal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Neurodegeneration: As used herein, the term "neurodegeneration" means a process in which one or more neurons are damaged, decrease in function, become dysfunctional, are degraded, and/or accumulate structures such as Lewy bodies or α-synuclein aggregates. Neurodegeneration encompasses both rapid, gradual, and intermediate forms. Accordingly, a neurodegenerative disease, condition, or symptom is one characterized in that the disease is typically associated with neuronal damage, decrease in function, dysfunction, degradation, and/or accumulation of structures such as Lewy bodies or α-synuclein aggregates.

Sample: As used herein, the term "sample" means a small part of something intended to show the quality, nature or quantity of the whole thing. The term sample encompasses any sample obtained from any source. For example, a sample containing an enzyme of interest may be obtained from an enzyme production system, enzyme purification process, formulated drug substance, or a biological source.

Therapeutically effective amount: As used herein, the term "therapeutically effective amount" refers to an amount of a therapeutic protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

BRIEF DESCRIPTION OF THE DRAWINGS

FIG. 1 includes an exemplary diagram, exemplary graphs, and exemplary western blot images showing that AAV-GBA1 gene therapy induces an increase in GBA1 protein levels and GCase activity. The displayed diagram, graphs, and western blot images relate to 2-3 month old ASO mice that received unilateral injections into the substantia nigra, striatum and hippocampus of either AAV-GFP control or AAV-GBA1, as shown in the diagram of Panel A of FIG. 1. Panel B of FIG. 1 is a graph showing that overexpression of AAV-GBA1 caused an increase in GCase activity in brain in comparison to AAV-GFP control mice. Panel C of FIG. 1 is set including western blots and a graph quantifying the western blot results, where the western blots were performed using total lysate (20 μg) from the substantia nigra, striatum and hippocampus 3-months post-AAV injection to verify transgene overexpression.

FIG. 2 includes an exemplary series of western blots and graphs showing that intra-cerebral injection of AAV-GBA1 in ASO mice increases LC3-II and reduces levels of high molecular weight (HMW) α-synuclein, 3-months post gene therapy delivery. Panel A of FIG. 2 is a series of western blots and graphs showing that gene delivery of AAV-GBA1 increased protein levels of LC3-II in the substantia nigra and striatum in comparison to AAV-GFP control mice while, in contrast, levels of LC3-II remained unchanged in the hippocampus. Panel B of FIG. 2 is a western blot and set of graphs showing that AAV-GBA1 caused an increase in LC3-II, which corresponded to a reduction in the number of HMW α-synuclein oligomeric species in the substantia nigra and striatum in comparison to AAV-GFP control mice. Consistent with protein levels of LC3-II in the hippocampus, Panel B of FIG. 2 shows that the number of HMW α-synuclein oligomeric species remained unchanged in the hippocampus. N=5 animals per group. Data were analyzed using a 1-way ANOVA followed by Tukey's multiple comparison post-hoc test, * p<0.05, graphs expressed as mean±SEM.

FIG. 3 includes an exemplary series of images and graphs showing that intra-cerebral injection of AAV-GBA1 reduced insoluble α-synuclein aggregates ASO mice, 8-months post gene therapy delivery. Data were collected from 2-3 month old ASO mice having received unilateral injections of either AAV-GFP (control) or AAV-GBA1 transgene into the substantia nigra and striatum. Panel A of FIG. 3 and Panel D of FIG. 3 are images showing verification of transgene expression of AAV-GFP and AAV-GBA1 in the substantia nigra (Panel A) and striatum (Panel D), respectively, at 8-months post gene delivery. Panel B of FIG. 3, Panel C of FIG. 3, Panel E of FIG. 3, and Panel F of FIG. 3 are images and graphs showing that the number of insoluble α-synuclein aggregates (illustrated using white arrows) in the substantia nigra (Panel B of FIG. 3 and Panel C of FIG. 3) and striatum (Panel E of FIG. 3 and Panel F of FIG. 3), respectively, of ASO mice was decreased following AAV-GBA1 gene delivery as compared to AAV-GFP control ASO mice. Scale bar=25 μm. N=4-6 animals per group. Data were analyzed using a 1-way ANOVA followed by Tukey's multiple comparison post-hoc test, * p<0.05, graphs are expressed as mean±SEM.

FIG. 4 includes an exemplary diagram, exemplary charts, exemplary western blot, and exemplary images showing that intra-nigral administration of AAV-GBA1 causes an increase in GBA1 protein levels and GCase activity. Panel A of FIG. 4 is a diagram showing that naïve rats received an intra-nigral injection of AAV-GFP control transgene or a co-injection of either AAV-GFP+AAV-mutant A53T α-synuclein or AAV-GBA1+AAV-mutant A53T α-synuclein. Panel B of FIG. 4 is a graph showing confirmation of the expression of transgenes in the substantia nigra DA neurons using immunofluorescence at 24-weeks post-AAV injection. Panel C of FIG. 4 is a chart and a western blot showing that the treatment diagramed in Panel A of FIG. 4 resulted in an increase GCase activity in the substantia nigra at 8-weeks post AAV-injection. Panel D of FIG. 4 is a series of images showing labeling for GFP, human α-synuclein and TH. Right-most images show an overlay of the three labels.

FIG. 5 includes an exemplary series of images and a graph showing that intra-nigral administration of AAV-GBA1 is neuroprotective against the A53T α-synuclein induced neurodegeneration. Panel A of FIG. 5 and Panel B of FIG. 5 are images from which stereological analysis of the total number of DA neurons in the SNpc indicated that an intra-nigral administration of AAV-mutant A53T α-synuclein caused ~50% decrease in the DA neurons compared to control rats injected with AAV-GFP. Panel C of FIG. 5 is an image showing that intra-nigral administration of AAV-GBA1 rescued DA neurons from the mutant A53T α-synuclein induced degeneration. Panel D of FIG. 5 is a graph showing TH-ir/Nissl cells in SNc as related to Panel A of FIG. 5, Panel B of FIG. 5, and Panel C of FIG. 5, respectively. N=4-10 animals per group. Data were analyzed using a 1-way ANOVA followed by Tukey's multiple comparison post-hoc test, * p<0.05, graphs are expressed as mean±SEM.

FIG. 6 includes an exemplary series of western blots and graphs showing that mutant A53T α-synuclein induced changes in macroautophagy protein levels, which are restored by an intra-nigral injection of AAV-GBA1. Western blots were performed using total lysate (10-20 μg) of naïve rats that received an intra-nigral injection of AAV-GFP control transgene or a co-injection of either AAV-GFP+ AAV-mutant A53T α-synuclein or AAV-GBA1+AAV-mutant A53T α-synuclein. Panel A of FIG. 6 is a western blot and graph showing that, at 8-weeks post AAV-mutant A53T α-synuclein, the lipidated form of LC3 (LC3-II) remained unchanged in the substantia nigra. Panel B of FIG. 6 is a western blot and graph showing that, at 8-weeks post AAV-mutant A53T α-synuclein, the lipidated form of LC3 (LC3-II) decreased in the striatum of rats injected with mutant A53T α-synuclein, and was restored by AAV-GBA1. Panel C of FIG. 6 is a western blot and graph showing that levels of p62 were decreased in the substantia nigra of rats that received AAV-mutant A53T α-synuclein and restored when co-administered with AAV-GBA1. Panel D of FIG. 6 is a western blot and graph showing that levels of p62 were increased in the striatum of rats that also were co-administered AAV-mutant A53T α-synuclein and AAV-GBA1. Panel E of FIG. 6 and Panel F of FIG. 6 are each a western blot and graph showing that LAMP-2A remained unchanged in the substantia nigra (Panel E of FIG. 6) and striatum (Panel F of FIG. 6), respectively. Data were analyzed using a 1-way ANOVA followed by Tukey's multiple comparison post-hoc test, *p<0.05, graphs expressed as mean±SEM.

DETAILED DESCRIPTION

Figure 1:
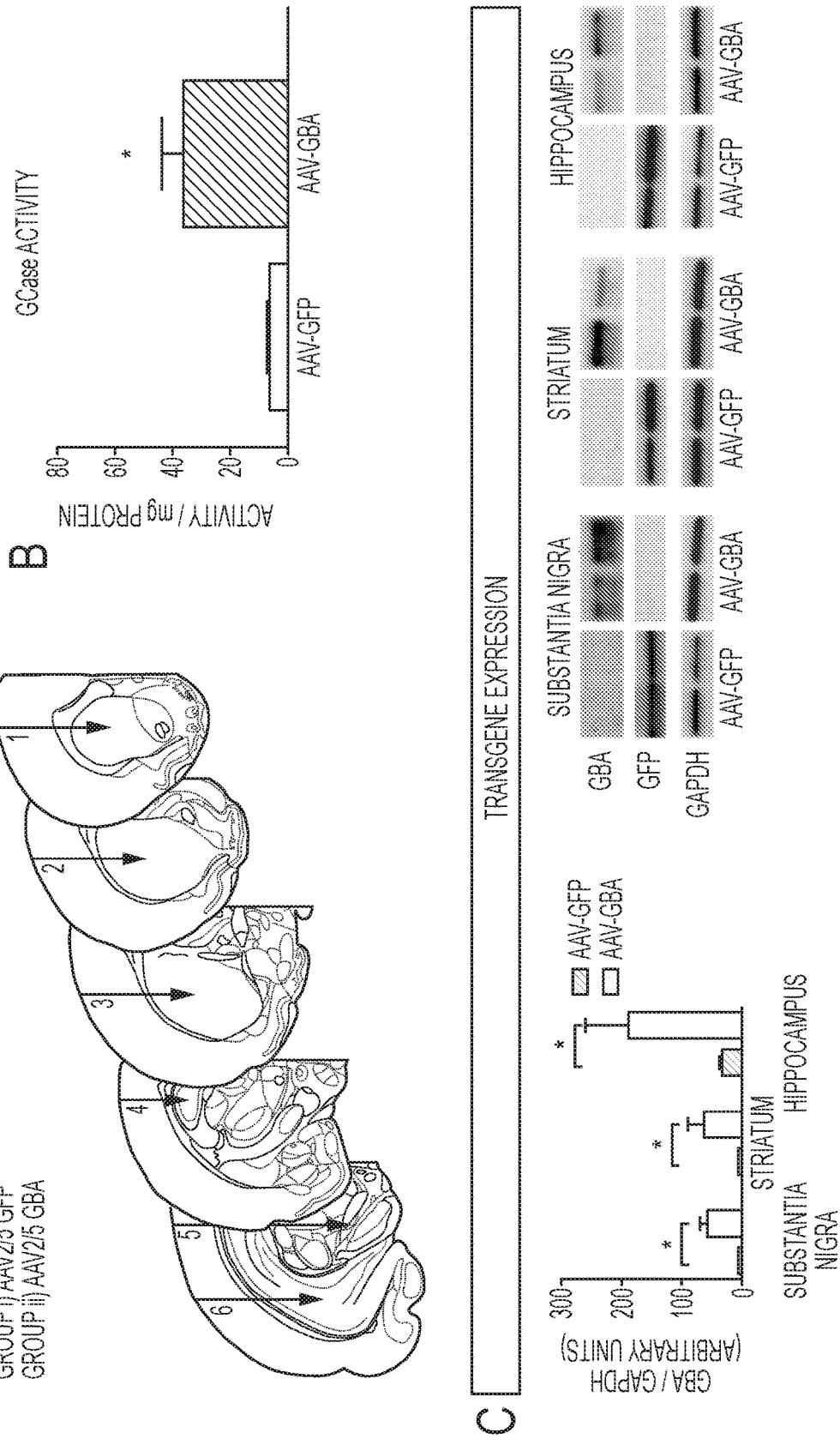
FIG. 1 is a figure including three panels: A, B, and C.

The present invention is directed, in part, to the treatment of a subject having a neurodegenerative disorder, such as Parkinson's disease (PD), by providing glucocerebrosidase nucleic acid or protein. The glucocerebrosidase may be provided, e.g., through gene therapy or by administration of a glucocerebrosidase protein. Accordingly, the present application encompasses glucocerebrosidase nucleic acids or proteins for use in the treatment of PD or other neurodegenerative disorders.

Glucocerebrosidase

Glucocerebrosidase enzyme is typically capable of breaking down glucosylceramide into the products glucose and ceramide. In some instances, glucocerebrosidase can also cleave glucosylsphingosine to generate glucose and sphingosine. In certain instances, glucocerebrosidase is capable of catalyzing transglucosylation between glucosylceramide and n-alkanols. Deficiency of glucocerebrosidase enzyme can result in clinical phenotypes. For instance, deficiency of glucocerebrosidase can lead to the progressive accumulation of glucosylceramide within macrophages, potentially leading to symptoms such as hepatosplenomegaly, anemia, thrombocytopenia, and skeletal involvement.

Glucocerebrosidases of the present invention include any protein or nucleic acid having at least 40% homology or identity (e.g., 40%, 45%, 50%, 55%, 60%, 65%, 70%, 75%, 80%, 85%, 90%, 95%, 99%, or 100% homology or identity) to a known glucocerebrosidase enzyme or nucleic acid, respectively; any protein capable of recapitulating all or a portion of one or more native glucocerebrosidase enzyme activities; or any nucleic acid encoding a protein capable of recapitulating all or a portion of one or more native glucocerebrosidase enzyme activities. Thus, "glucocerebrosidase" and grammatical equivalents can refer to either or both of a glucocerebrosidase protein and a glucocerebrosidase nucleic acid.

As used herein, the terms "glucocerebrosidase enzyme," "glucocerebrosidase protein," and grammatical equivalents, are used interchangeably. Glucocerebrosidase enzyme can also be referred to as acid β-glucosidase, β-glucosidase, glucosidase, glucosidase β acid, GBA, D-glucosyl-N-acyl sphingosine glucohydrolase, glucosylceramidase, or GCase.

As used herein, "glucocerebrosidase nucleic acid" and grammatical equivalents mean any nucleic acid or segment of a nucleic acid encoding one or more amino acids that may be expressed within a glucocerebrosidase protein as described herein. Accordingly, a vector including a segment encoding a glucocerebrosidase protein is a glucocerebrosidase nucleic acid and any segment of such a vector that encodes a glucocerebrosidase protein is also a glucocerebrosidase nucleic acid. A glucocerebrosidase nucleic acid, e.g., a vector including a segment that encodes a glucocerebrosidase protein, may include nucleotides that do not encode a glucocerebrosidase protein, including but not limited to regulatory sequences and other nucleotides that contribute to the functions of the vector.

The present invention may include any glucocerebrosidase protein or nucleic acid, including any recombinant or naturally-occurring glucocerebrosidase protein or nucleic acid.

The present invention encompasses naturally-occurring glucocerebrosidases (e.g., wild-type or mutant forms) or glucocerebrosidases produced through in vivo or in vitro gene or protein recombination, engineering, synthesis, combinations thereof, or other techniques of molecular biology.

Glucocerebrosidase enzyme can be encoded by various nucleic acids. For instance, in humans, GBA-1 gene is thought to ubiquitously express a glucocerebrosidase enzyme. The art includes the sequences of many glucocerebrosidase nucleic acids, including, for instance, glucocerebrosidase nucleic acids identified as a result of the sequencing of GBA-1 genes from human subjects, e.g., subjects having Gaucher disease, subjects being diagnosed for Gaucher disease, control subjects, random subjects, or the bulk analysis of two or more subjects, e.g., to identify normative sequences (see, e.g., Beutler et al., 1994, Molecular Medicine 1(1): 82-92; Lesage et al. 2011 Human Molecular Genetics 20(1):202-10). Known glucocerebrosidase nucleic acids include the human glucocerebrosidase gene, located on chromosome 1q21 and spanning 7.6 kb of genomic DNA divided into 11 exons (see, e.g., Beutler et al. 1992 Genomics 12(4): 795-800 and GenBank Accession No. J03059; SEQ ID NO.: 1; see also), human glucocerebrosidase mRNA and cDNA sequences (see, e.g., GenBank Accession No. M16328; SEQ ID NO.: 2), mouse glucocerebrosidase gene (see, e.g., GenBank Accession No. NC_000069), and mouse glucocerebrosidase mRNA and cDNA sequences (see, e.g., GenBank Accession No. NM_001077411). Alternative splicing can result in multiple glucocerebrosidase transcript variants. For example, at least five mRNA variants of glucocerebrosidase have been identified (see, e.g., Entrez Gene ID No. 2629).

Glucocerebrosidase enzyme may also be encoded by nucleic acids derived from natural or laboratory-induced mutation of a naturally-occurring glucocerebrosidase nucleic acids or other glucocerebrosidase nucleic acid described herein.

In some embodiments, a glucocerebrosidase nucleic acid of the present invention is any nucleic acid or portion of a nucleic acid (e.g., comprising 100, 200, 300, 400, 500, 600, 700, 800, 900, 1,000, 1,500, 2,000, 2,500, 3,000, 3,500, 4,000, 4,500, 5,000, 6,000, 7,000, 8,000, 9,000, 10,000, 20,000, 30,000, 40,000, 50,000 or more nucleotides) of a glucocerebrosidase nucleic acid having at least 70% homology or identity (e.g., 70, 71, 72, 73, 74, 75, 80, 85, 90, 95, or 100% homology or identity) to a naturally-occurring or recombinant glucocerebrosidase nucleic acid, including, but not limited to, nucleic acids encoding those recombinant glucocerebrosidase proteins described herein, such as velaglucerase alfa, alglucerase, imiglucerase, taliglucerase, and ceridase. In some embodiments, a glucocerebrosidase nucleic acid of the present invention is a nucleic acid or a portion of a nucleic acid (e.g., comprising 100, 200, 300, 400, 500, 600, 700, 800, 900, 1,000, 1,500, 2,000, 2,500, 3,000, 3,500, 4,000, 4,500, 5,000, 6,000, 7,000, 8,000, 9,000, 10,000, 20,000, 30,000, 40,000, 50,000, or more, or all nucleotides) having at least 70% homology or identity (e.g., 70, 71, 72, 73, 74, 75, 80, 85, 90, 95, or 100% homology or identity) over all or a portion of its length (e.g., over 100, 200, 300, 400, 500, 600, 700, 800, 900, 1,000, 1,500, 2,000, 2,500, 3,000, 3,500, 4,000, 4,500, 5,000, 6,000, 7,000, 8,000, 9,000, 10,000, or more nucleotides, and/or over its full length) to all or a portion of SEQ ID NO.: 1 or SEQ ID NO.: 2 (e.g., 100, 200, 300, 400, 500, 600, 700, 800, 900, 1,000, 1,500, 2,000, 2,500, 3,000, 3,500, 4,000, 4,500, 5,000, 6,000, 7,000, 8,000, or more nucleotides, and/or the full length of SEQ ID NO.: 1 or SEQ ID NO.: 2).

Glucocerebrosidase nucleic acids may be derived from a variety of sources. A glucocerebrosidase nucleic acid of the present invention may be isolated or purified. In particular embodiments, a nucleic acid of the present invention is a purified nucleic acid for gene therapy.

In some embodiments, glucocerebrosidase nucleic acids of the present invention include recombinant glucocerebrosidase nucleic acids. As used herein, the term recombinant glucocerebrosidase nucleic acid refers to any glucocerebrosidase nucleic acid produced using a recombinant technology.

Glucocerebrosidase nucleic acids of the present invention can include DNA, such as genomic DNA, isolated DNA, recombinant DNA, in vitro synthesized DNA, or any other DNA known in the art. Glucocerebrosidase nucleic acids can include cDNA, such as cDNA of the coding sequence of a glucocerebrosidase nucleic acid known in the art or disclosed herein or encoding a glucocerebrosidase protein known in the art or disclosed herein. Glucocerebrosidase nucleic acids can include RNA, such as endogenously expressed mRNA, transgenically expressed mRNA, or in vitro synthesized mRNA. The present invention further encompasses modified nucleic acids and nucleic acids including nucleotides other than A, C, G, T, and U, such as synthetic nucleotides.

A composition of glucocerebrosidase nucleic acids may include nucleic acids having multiple distinct sequences, e.g., nucleic acids having non-coding differences and capable of expressing identical primary glucocerebrosidase protein sequences or nucleic acids having glucocerebrosidase coding sequence differences and therefore capable of expressing distinct primary glucocerebrosidase protein sequences.

In humans, GBA-1 is thought to ubiquitously express a glucocerebrosidase enzyme that is typically initially synthesized as a 519 amino acid protein. Some reports identify a human glucocerebrosidase enzyme having 536 amino acids. In some instances, following translation, a 23 amino acid signal peptide is removed from the protein. Various glucocerebrosidase protein sequences are known in the art, including, e.g., the human glucocerebrosidase sequence provided in UniProt P04062 (SEQ ID NO.: 3).

Glucocerebrosidase proteins can include additional co-translational and/or post-translational modifications. For instance, glucocerebrosidase can accumulate four co-translationally acquired N-linked glycans and/or acquire post-translational modifications. Insofar as co-translational and post-translational modification of proteins are ingrained functions of many cells and cell types, one of skill in the art will appreciate that a provided cell will be understood to provide sufficient or appropriate modifications to facilitate substantial protein function, e.g., of an expressed glucocerebrosidase protein, if any are in fact required, under any particular circumstance for any particular use or function, barring clear evidence to the contrary. Moreover, those of skill in the art will appreciate that certain cells are expected to provide sufficient modifications, e.g., mammalian cells. Further, methods of modifying the range or frequency of modifications of which any particular cell or cell type is capable are known in the art.

In some embodiments, the present invention is applicable to recombinant glucocerebrosidases including, but not limited to the recombinant enzymes known as velaglucerase alfa, alglucerase, imiglucerase, taliglucerase, and ceridase, or nucleic acids by which these or other recombinant enzymes are encoded. Velaglucerase alfa is an enzyme indicated for long-term enzyme replacement therapy for pediatric and adult patients with Gaucher disease Type 1. Velaglucerase alfa may also be known as VPRIV®. The sequences of velaglucerase alfa can be:

```
                                        (SEQ ID NO.: 4)
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPAQ

NLLLKSYFSEEGIGYNIIRVPMASCDFSIRTYTYADTPDDFQLHNFSLPEE

DTKLKIPLIHRALQLAQRPVSLLASPWTSPTWLKTNGAVNGKGSLKGQPGD

IYHQTWARYFVKFLDAYAEHKLQFWAVTAENEPSAGLLSGYPFQCLGFT
```

```
PEHQRDFIARDLGPTLANSTHEINVRLLMLDDQRLLLPHWAKVVLTDPEA

AKYVHGIAVHWYLDFLAPAKATLGETHRLFPNTMLFASEACVGSKFWEQ

SVRLGSWDRGMQYSHSIITNLLYHVVGWTDWNLALNPEGGPNWVRNFV

DSPIIVDITKDTFYKQPMFYHLGHFSKFIPEGSQRVGLVASQKNDLDAVAL

MHPDGSAVVVVLNRSSKDVPLTIKDPAVGFLETISPGYSIHTYLWRRQ
```

Imiglucerase is recombinant, infusible enzyme that is produced in Chinese hamster ovary cells and differs from the archetypal wild-type human enzyme sequence by a single amino-acid substitution at position 495. Imiglucerase can have the sequence:

```
                                        (SEQ ID NO.: 5)
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAKATLGETHRLFPNTMLFASEACVGSKFWEQ

SVRLGSWDRGMQYSHSIITNLLYHVVGWTDWNLALNPEGGPNWVRNFV

DSPIIVDITKDTFYKQPMFYHLGHFSKFIPEGSQRVGLVASQKNDLDAVA

LMHPDGSAVVVVLNRSSKDVPLTIKDPAVGFLETISPGYSIHTYLWRRQ
```

Taliglucerase alfa is a novel plant cell-derived recombinant human glucocerebrosidase enzyme. Taliglucerase alfa is a 506 amino acid enzyme, of which 497 amino acids encode for human glucocerebrosidase. This sequence differs from the archetypal wild-type human glucocerebrosidase enzyme sequence by the addition of amino acids at the N-terminus and C-terminus of the protein. For instance, taliglucerase alfa may differ from human glucocerebrosidase by two amino acids at the N terminus and up to 7 amino acids at the C terminus.

The present invention includes any glucocerebrosidase enzymes provided herein, within the definition of glucocerebrosidase enzyme provided herein, or that may be derived from natural or laboratory-induced mutation of a naturally-occurring glucocerebrosidase or other glucocerebrosidase enzyme.

In some embodiments, a glucocerebrosidase enzyme of the present invention is any protein or a portion of a protein (e.g., comprising at least 30, 35, 40, 45, 50, 60, 70, 80, 90, 100, 200, 300, 400, 450, 500, 525, 550, or more, or all amino acids) of a glucocerebrosidase protein having at least 70% homology or identity (e.g., 70, 71, 72, 73, 74, 75, 80, 85, 90, 95, or 100% homology or identity) to a naturally-occurring or recombinant glucocerebrosidase enzyme, including, but not limited to, those recombinant glucocerebrosidase proteins described herein such as velaglucerase alfa, alglucerase, imiglucerase, taliglucerase, and ceridase. In some embodiments, a glucocerebrosidase enzyme suitable for the present invention is any protein or portion of a protein (e.g., comprising at least 30, 35, 40, 45, 50, 60, 70, 80, 90, 100, 200, 300, 400, 450, 500, 525, 550, or more, or all amino acids) of a glucocerebrosidase protein having at least 70% homology or identity (e.g., 70, 71, 72, 73, 74, 75, 80, 85, 90, 95, or 100% homology or identity) to SEQ ID NO.: 3, SEQ ID NO.: 4 or SEQ ID NO.: 5.

Glucocerebrosidase enzyme may be derived from a variety of sources. A suitable sample for the present invention may contain glucocerebrosidase in any form (e.g., isolated or not, purified or unpurified). In particular embodiments, a suitable sample for the present invention is a sample containing a purified glucocerebrosidase for enzyme replacement therapy, also referred to as replacement glucocerebrosidase enzyme. Such a sample may be a drug substance, drug product, or a stability sample. Purified replacement glucocerebrosidase may be recombinant, synthetic, gene-activated or natural enzyme.

In some embodiments, glucocerebrosidase enzyme of the present invention includes recombinant glucocerebrosidase. As used herein, the term recombinant glucocerebrosidase refers to any glucocerebrosidase produced using a recombinant technology. Suitable expression systems for recombinant technology include, for example, egg, baculovirus, plant, yeast, or mammalian cells. In some embodiments, a recombinant glucocerebrosidase is produced by cells engineered to express glucocerebrosidase. Typically, cells encoding a glucocerebrosidase enzyme may be cultured under standard cell culture conditions such that glucocerebrosidase enzyme is produced by the cells.

In some embodiments, glucocerebrosidase enzymes are produced in mammalian cells. Non-limiting examples of mammalian cells that may be used in accordance with the present invention include BALB/c mouse myeloma line (NSO/1, ECACC No.: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59, 1977); human fibrosarcoma cell line (e.g., HT1080); baby hamster kidney cells (BHK21, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TM cells (Mather et al., Annals N.Y. Acad. Sci., 383:44-68, 1982); MRC 5 cells; FS4 cells; and a human hepatoma line (Hep G2).

In some embodiments, recombinant glucocerebrosidase enzymes produced from human cells (e.g., HT1080) are purified. In some embodiments, recombinant glucocerebrosidase enzymes produced from CHO cells are purified.

Typically, cells that are engineered to express recombinant glucocerebrosidase may comprise a transgene that encodes a glucocerebrosidase protein described herein. It should be appreciated that the nucleic acids encoding glucocerebrosidase may contain regulatory sequences, gene control sequences, promoters, non-coding sequences and/or other appropriate sequences for expressing the glucocerebrosidase. Typically, the coding region is operably linked with one or more of these nucleic acid components. A glucocerebrosidase sample may be purified according to any of a variety of methods known in the art.

In some instances, a sample is taken from an organism and contains a naturally-occurring glucocerebrosidase. Such a sample may be derived, for example, from a tissue sample (e.g., a tissue biopsy, e.g. an organ biopsy), from drawn blood, from bodily fluids, from cells, or by other means known in the art. A glucocerebrosidase enzyme sample may be derived for a mammal, such as a mouse, rat, guinea pig, dog, cat, horse, pig, non-human primate, or human. Samples may be used with or without further processing. In some instances a sample may be sterilized, homogenized, diluted, disassociated, or processed to isolate particular cell types or cellular components, such as lysosomes. Methods thereof are well known to those of skill in the art.

A composition of glucocerebrosidase enzyme may include multiple forms of the enzyme.

Gene Therapy Vectors

Glucocerebrosidase nucleic acids described herein may be incorporated within a wide variety of gene therapy constructs, e.g., to deliver a glucocerebrosidase nucleic acid to a subject in need thereof. A vector construct refers to a polynucleotide molecule including all or a portion of a viral genome and a transgene. In some instances, gene transfer can be mediated by a DNA viral vector, such as an adenovirus (Ad) or adeno-associated virus (AAV). Other vectors useful in methods of gene therapy are known in the art. For example, a construct of the present invention can include an alphavirus, herpesvirus, retrovirus, lentivirus, or vaccinia virus.

Adenoviruses are a relatively well characterized group of viruses, including over 50 serotypes (see, e.g., WO 95/27071, which is herein incorporated by reference). Adenoviruses are tractable through the application of techniques of molecular biology and may not require integration into the host cell genome. Recombinant Ad-derived vectors, including vectors that reduce the potential for recombination and generation of wild-type virus, have been constructed (see, e.g., international patent publications WO 95/00655 and WO 95/11984, which are herein incorporated by reference). Wild-type AAV has high infectivity and is capable of integrating into a host genome with a high degree of specificity (see, e.g. Hermonat and Muzyczka 1984 Proc. Natl. Acad. Sci., USA 81:6466-6470 and Lebkowski et al. 1988 Mol. Cell. Biol. 8:3988-3996).

AAV of any serotype or pseudotype can be used. Certain AAV vectors are derived from single stranded (ss) DNA parvoviruses that are nonpathogenic for mammals. Briefly, rep and cap viral genes that can account for 96% of the archetypical wild-type AAV genome can be removed in the generation of certain AAV vectors, leaving flanking inverted terminal repeats (ITRs) that can be used to initiate viral DNA replication, packaging and integration. Wild type AAV integrates into the human host cell genome with preferential site specificity at chromosome 19q13.3. Alternatively, AAV can be maintained episomally.

At least twelve human serotypes of AAV (AAV serotype 1 (AAV-1) to AAV-12) and more than 100 serotypes from nonhuman primates have been discovered to date. Any of these serotypes, as well as any combinations thereof, may be used within the scope of the present invention in a glucocerebrosidase nucleic acid.

A serotype of a viral vector used in certain embodiments of the invention can be selected from the group consisting from AAV1, AAV2, AAV3, AAV4, AAV5, AAV6, AAV7, AAV8, and AAV9 (see, e.g., Gao 2002 PNAS 99:11854 11859 and Manfredsson 2009 *Molecular Therapy* 17(3): 403-405). Other serotypes are known in the art or described herein and are also applicable to the present invention. In particular instances, the present invention includes an AAV9 viral vector including a glucocerebrosidase nucleic acid of the present invention.

A vector of the present invention can be a pseudotyped vector. Pseudotyping provides a mechanism for modulating a vector's target cell population. For instance, pseudotyped AAV vectors can be utilized in various methods described herein. Pseudotyped vectors are those that contain the genome of one vector, e.g., the genome of one AAV serotype, in the capsid of a second vector, e.g., a second AAV serotype. Methods of pseudotyping are well known in the art. For instance, a vector may be pseudotyped with envelope glycoproteins derived from Rhabdovirus vesicular stomatitis virus (VSV) serotypes (Indiana and Chandipura strains), rabies virus (e.g., various Evelyn-Rokitnicki-Abelseth ERA strains and challenge virus standard (CVS)), Lyssavirus Mokola virus, a rabies-related virus, vesicular stomatitis virus (VSV), Mokola virus (MV), lymphocytic choriomeningitis virus (LCMV), rabies virus glycoprotein (RV-G), glycoprotein B type (FuG-B), a variant of FuG-B (FuG-B2) or Moloney murine leukemia virus (MuLV). A virus may be pseudotyped for transduction of one or more neurons or groups of neurons, e.g., neurons of the brain, e.g., neurons of the substantia nigra.

Without limitation, illustrative examples of pseudotyped vectors include recombinant AAV2/1, AAV2/2, AAV2/5, AAV2/6, AAV2/7, and AAV2/8 serotype vectors. It is known in the art that such vectors may be engineered to include a transgene encoding a human protein or other protein. In particular instances, the present invention includes a pseudotyped AAV9 viral vector including a glucocerebrosidase nucleic acid of the present invention. and Viral Vectors for Gene Therapy: Methods and Protocols, ed. Machida, Humana Press, 2003.

In some instances, a particular AAV serotype vector may be selected based upon the intended use, e.g., based upon the intended route of administration. For example, for direct injection into the brain, e.g., either into the striatum, an AAV2 serotype vector can be used.

Various methods for application of AAV vector constructs in gene therapy are known in the art, including methods of modification, purification, and preparation for administration to human subjects (see, e.g., Viral Vectors for Gene Therapy: Methods and Protocols, ed. Machida, Humana Press, 2003). In addition, AAV based gene therapy targeted to cells of the CNS has been described (see, e.g., U.S. Pat. Nos. 6,180,613 and 6,503,888). High titer AAV preparations can be produced using techniques known in the art, e.g., as described in U.S. Pat. No. 5,658,776

The inclusion of non-native regulatory sequences, gene control sequences, promoters, non-coding sequences, introns, or coding sequences in a glucocerebrosidase nucleic acid of the present invention is contemplated herein. The inclusion of nucleic acid tags or signaling sequences, or nucleic acids encoding protein tags or protein signaling sequences, is further contemplated herein. Typically, the coding region is operably linked with one or more regulatory nucleic acid components.

A promoter included in a glucocerebrosidase nucleic acid of the present invention can be a tissue- or cell type-specific promoter, a promoter specific to multiple tissues or cell types, an organ-specific promoter, a promoter specific to multiple organs, a systemic or ubiquitous promoter, or a nearly systemic or ubiquitous promoter. Promoters having stochastic expression, inducible expression, conditional expression, or otherwise discontinuous, inconstant, or unpredictable expression are also included within the scope of the present invention. A promoter of the present invention may include any of the above characteristics or other promoter characteristics known in the art.

In some instances, a promoter of the present invention will be a promoter having specific expression in neurons, preferential expression in neurons, or that typically drives expression of an associated coding sequence in neurons or a subset of neurons but not in one or more other tissues or cell types. Examples of such promoters include synapsin I (SYN), calcium/calmodulin-dependent protein kinase II, tubulin alpha I, neuron-specific enolase, microtubule-associated protein 1B (MAP1B), and platelet-derived growth factor beta chain promoters, as well as derivatives thereof. Other examples of promoters include, but are not limited to, the cytomegalovirus (CMV) promoter (Kaplitt (1994) *Nat. Genet.* 8: 148-154), CMV/human .beta.3 globin promoter (Mandel (1998) *J. Neurosci.* 18: 4271-4284), GFAP promoter (Xu (2001) *Gene Ther.* 8: 1323-1332), the 1.8 kb neuron specific enolase (NSE) promoter (Klein (1998) *Exp. Neurol.* 150: 183-194), chicken beta actin (CBA) promoter (Miyazaki (1989) *Gene* 79: 269-277), the β-glucuronidase (GUSB) promoter (Shipley (1991) *Genetics* 10: 1009-1018), and ubiquitin promoters such as those isolated from human ubiquitin A, human ubiquitin B, and human ubiquitin C, as described in U.S. Pat. No. 6,667,174. Other promoters capable of neuronal expression are known in the art.

In some instances a promoter of the present invention can be, e.g., a promoter that confers or directs expression in glial cells, e.g., a promoter that selectively confers or directs expression in glial cells. In particular instances, a glial promoter of the present invention can be an IBA1 promoter or glial fibrillary acidic protein (GFAP) promoter. Other glial promoters are known in the art.

In some instances a promoter of the present invention can be, e.g., a promoter that confers or directs expression in neurons, e.g., a promoter that selectively confers or directs neuronal expression. A neuronal promoter of the present invention can be, e.g., a nestin promoter or a neuron specific enolase promoter. In some instances a promoter of the present invention will be, e.g., a phosphoglycerate kinase (PGK) promoter or a D1 and/or D2 dopamine receptor (DRD1/DRD2) promoter, or other promoter known in the art (see, e.g., Delzor et al. 2012 *Human Gene Therapy Methods* 23(4): 242-254, which is herein incorporated by reference).

Other regulatory elements may additionally be operably linked to the transgene, such as, e.g., the Woodchuck Hepatitis Virus Post Regulatory Element (WPRE) (Donello (1998) *J. Virol,* 72: 5085-5092) or the bovine growth hormone (BGH) polyadenylation site. For certain methods of the present invention, regulation of transcriptional activity in the CNS is regulated by inclusion of various regulatory elements and drug responsive promoters as described, for example, in Haberma (1998) *Gene Ther.,* 5: 1604-16011, and Ye (1995) *Science,* 283: 88-91.

Moreover, the promoter or other regulatory elements of any gene known or hypothesized to be neuronally expressed may be operably linked to a glucocerebrosidase coding sequence by methods known in the art.

In various embodiments of the present invention, expression of a glucocerebrosidase protein form a glucocerebrosidase nucleic acid, e.g., in the CNS or in a manner that results in the presence of transgenic protein in the CNS, treats PD.

In certain instances, glucocerebrosidase gene therapy includes compositions and methods according to the Sangamo method as known in the art. Sangamo technology can include the use of a zinc-finger nuclease/zinc-finger nicking enzyme (ZFN) to produce a site-specific double-stranded break (DSB) at a site having a predetermined sequence, where subsequent repair of the break results in targeted gene disruption or gene addition (see, e.g., Wang 2012 *Genome Research* 22: 1316-1326). According to Sangamo and similar methods, two ZFNs must be used such that DNA is bound by the two ZFNs at an appropriate orientation and spacing (for example, the two ZFNs may bind on opposite sides of DNA and with 5 or 6 bp separating them), permitting two cleavage domains to dimerize and subsequently cleave the bound segment of DNA. When a composition of the present invention is administered such that this cleavage occurs in the presence of a suitably designed donor DNA molecule, e.g., a DNA molecule having homology to the cleaved DNA and also including a segment encoding glucocerebrosidase, glucocerebrosidase nucleic acid can thereby be incorporated into the DNA.

Neurodegenerative Diseases, Disorders, and Conditions

Many neurodegenerative disorders are known in the art. One common neurodegenerative disorder is Parkinson's disease (PD). Other neurodegenerative disorders include Alzheimer's disease, Huntington's disease, and Amyotrophic lateral sclerosis (ALS; also referred to as motor neuron disease (MND), Charcot disease, or Lou Gehrig's disease).

As used herein, PD includes a range of symptoms and conditions. Further, as used herein, PD includes "Parkinson plus diseases," encompassing conditions sharing symptoms with primary parkinsonisms while presenting additional features. Examples of Parkinson plus diseases include progressive supranuclear palsy and multiple system atrophy. Other Parkinson plus diseases are known in the art.

PD can result from a variety of causes, including drug use, cerebral infarction, genetic factors, environmental factors, other medical conditions, such as Alzheimer's disease, or a combination thereof. In certain instances, PD has no known or identifiable cause.

Neurodegeneration is a hallmark of PD. Amongst possible neurodegenerative events in PD, a common event is the death of cells in the substantia nigra, a region of the midbrain. Certain neurons of the substantia nigra are specialized to synthesize and release dopamine. PD can include a reduction in the number or activity of dopamine-secreting cells, e.g., in the substantia nigra. In particular instances, cell death occurs in a region of the substantia nigra known as the pars compacta. Some studies have indicated that symptoms of PD are apparent when 50% or more, or even 75-80%, of dopaminergic innervation is lost.

PD can affect many of the brains pathways, including the motor, oculo-motor, associative, limbic, and orbitofrontal circuits. Without wishing to adhere to any particular scientific theory, PD may result in the loss of neural activity that normally serves to prevent motor systems from becoming active at inappropriate times, a process in which dopamine is theorized to function.

Also without wishing to be bound by any particular scientific theory, pathological accumulation of alpha-synuclein, e.g. of alpha-synuclein bound to ubiquitin, has been associated with cellular damage and PD. Accumulated alpha-synuclein can form inclusions known as Lewy bodies. In some instances of PD, Lewy bodies first appear in the olfactory bulb, medulla oblongata, and pontine tegmentum, in some instances prior to development of clinical symptoms. As PD progresses, Lewy bodies can sometimes appear in the substantia nigra, areas of the midbrain and basal forebrain, and final in the neocortex. Neural degeneration in PD is associated with areas of the brain in which Lewy bodies appear.

Symptoms of PD are well known in the art. One commonly observed symptom of PD is tremors, observed in approximately 70% of patients during early stages of disease, and more as the disease progresses. A rest tremor is a type of tremor occurs when a muscle is at rest and is not normally observed during voluntary movement or during sleep. Such tremors typically occur in a distal portion of the body and are often largely isolated to a particular limb, such as a single arm or leg, at onset, with bilateral involvement during later stages. The frequency of such tremors is typically between 4 and 6 cycles per second. One archetypal type of tremor, "pill-rolling," involves contacting the thumb and index finger followed by circular movement.

PD can result in difficulty across a broad range of movements and movement-related processes, including planning, initiation, and execution. PD can result in difficulty in the performance of sequential and/or simultaneous movements. For example, PD can result in difficulty with motor control tasks such as writing, sewing, dressing. PD can result in muscle spasticity, progressive weakness, muscle atrophy, and other symptoms. Tasks such as alternating movements between both hands or both feet can be used in the assessment of PD.

A common symptom of PD is bradykinesia, or slowness of movement, sometimes described as a slowness of initiation of voluntary movement with progressive reduction in speed and amplitude of repetitive actions. Bradykinesia can occur early in PD, affecting tasks such as writing and dressing, or others that require fine motor control. Presence or severity of bradykinesia can be subject to emotional state, the nature of the activity, or environmental factors such as the presence of an external cue.

Another common symptom of PD is rigidity, or stiffness and resistance to movement, e.g., limb movement. This can occur, in some instances, as a result of increased, excessive, and/or continuous muscle contraction. Rigidity encompasses uniform rigidity, also referred to as lead-pipe rigidity, and ratchetry, also referred to as cogwheel rigidity. Rigidity can be associated with joint pain. Rigidity may be initially effect the neck or shoulder muscles, with involvement of extremities and facial muscles at later stages, in some cases spread throughout large portions of a subject's body or a subject's entire body.

Another common symptom of PD is impaired balance, leading to frequent falls and bone fractures. Impaired balance is associated with postural instability.

In some instances, PD includes neuropsychiatric symptoms, such as pathological changes in cognition, mood, or behavior. The most common cognitive deficit in PD-affected individuals is executive dysfunction, which can include problems with planning, cognitive flexibility, abstract thinking, rule acquisition, initiating appropriate actions, inhibiting inappropriate actions, or differentiating relevant from irrelevant sensory information. Difficulty in attention, speed of cognition, memory, recall (e.g., recall of learned information), visuospatial perception, and facial recognition have also been observed in some cases. Other examples of neuropsychiatric symptoms of PD can include, e.g., depression, apathy, anxiety, decreased use or presence of facial expressions (e.g., a mask-like facial expression), decreased movement, a state of indifference, quiet speech, impulsive behaviors (such as medication overuse), cravings, binge eating, hypersexuality, pathological gambling, hallucinations, delusions, difficulty sleeping, daytime drowsiness, disturbances in REM sleep, or insomnia.

PD is related to several eye and vision abnormalities such as decreased blink rate, dry eyes, deficient ocular pursuit (eye tracking), decreased, saccadic movements (fast automatic movements of both eyes in the same direction), difficulties in directing one's gaze upward, blurred, and double vision. Changes in perception may include an impaired sense of smell, sensation of pain and paresthesia (skin tingling and numbness).

PD-associated alterations in the autonomic nervous system can lead to orthostatic hypotension (low blood pressure upon standing), oily skin, excessive sweating, urinary incontinence and altered sexual function. Constipation and gastric dysmotility can also occur.

Late stages of PD may be associated with complications such as choking, pneumonia, and falls. Progression of PD can require the assignment of a caregiver or institutionalization (e.g., entry into a nursing home or other care facility). PD can result in death. Other symptoms of PD and other neurodegenerative disorders are known in the art.

Symptoms can occur years before diagnosis of the disease. Any of the symptoms described herein can occur as a result of or in association with any other neurodegenerative disorder described herein.

Various criteria are available for the diagnosis of PD. Standards for the diagnosis of PD are known in the art. For instance, one set of standards is provided by the UK Parkinson's Disease Society Brain Bank (Table 1). Another set of standards for the diagnosis of PD is provided by the U.S. National Institute of Neurological Disorders and Stroke (NINDS; Table 2).

TABLE 1

| | |
|---|---|
| Step 1: Inclusion criteria (Both requirements must be met) | Bradykinesia And at least one of: Muscular rigidity; 4-6 Hz rest tremor; Postural instability not caused by primary visual, vestibular, cerebellar, or proprioceptive dysfunction |
| Step 2: Exclusion criteria | History of repeated strokes with stepwise progression of parkinsonian features History of repeated head injury History of definite encephalitis Oculogyric crises Neuroleptic treatment at onset of symptoms More than one affected relative Sustained remission Strictly unilateral features after 3 yr. Supranuclear gaze palsy Cerebellar signs Early severe autonomic involvement Early severe dementia with disturbances of memory, language, and praxis Babinski sign Presence of cerebral tumor or communicating hydrocephalus on CT scan Negative response to large doses of L-dopa (if malabsorption excluded) MPTP exposure |
| Step 3: Supportive criteria (Three or more required for definite diagnosis of PD) | Unilateral onset Rest tremor present Progressive disorder Persistent asymmetry affecting side of onset most Excellent response (70-100%) to levodopa Severe levodopa-induced chorea Levodopa response for 5 yr. or more Clinical course of 10 yr. or more |

TABLE 2

| | |
|---|---|
| Group A features (characteristic of PD) | Resting tremor Bradykinesia Rigidity Asymmetric onset |
| Group B features (suggestive of alternative diagnoses) | Features unusual early in the clinical course Prominent postural instability in the first 3 years after symptom onset |

TABLE 2-continued

| | |
|---|---|
| | Freezing phenomenon in the first 3 years Hallucinations unrelated to medications in the first 3 years Dementia preceding motor symptoms or in the first year Supranuclear gaze palsy (other than restriction of upward gaze) or slowing of vertical saccades Severe, symptomatic dysautonomia unrelated to medications Documentation of condition known to produce parkinsonism and plausibly connected to the patient's symptoms (such as suitably located focal brain lesions or neuroleptic use within the past 6 months) |
| Criteria for definite PD | All criteria for probable Parkinson's are met; histopathological confirmation of the diagnosis is obtained at autopsy |
| Criteria for probable PD | At least three of the four features in group A are present; none of the features in group B is present for a duration >3 years; substantial and sustained response to levodopa or a dopamine agonist has been documented |
| Criteria for possible PD | At least two of the four features in group A are present; at least one of these is tremor or bradykinesia; either none of the features in group B is present or has not been present for 3 years; and either substantial and sustained response to levodopa or a dopamine agonist has been documented or the patient has not had an adequate trial of levodopa or a dopamine agonist |

Additional standards have been developed for determining the stage of PD in a subject. For instance, staging the progression of PD may occur through Braak staging (Table 3) or Hoehn and Yahr Staging (Table 4). Braak staging includes 6 stages based largely on synuclein pathology.

TABLE 3

| Braak staging | |
|---|---|
| Stage one (Medulla oblongata) | Lesions initially occur in the dorsal glossopharyngeal/vagal motor nucleus and frequently in the anterior olfactory nucleus. This explained the reason in some pre-symptomatic PD victims has loss of sense of smell. There may also have involvement of intermediate reticular zone. Along with this stage is the Lewy pathology in the enteric nervous system, which explained gastrointestinal symptoms in pre-symptomatic phase. The pathology in the anterior olfactory nucleus expands less readily into related areas than that expanding from the brain stem which takes an upward course. |
| Stage two (Medulla oblongata + pontine tegmentum) | This include the pathology of stage 1 with s lesions in caudal raphe nuclei, gigantocellular reticular nucleus, and coeruleus-subcoeruleus complex. |
| Stage three (Midbrain) | Pathology of stage 2 plus midbrain lesions, particularly in the pars compacta of the substantia nigra. |
| Stage four (basal prosencephalon and mesocortex) | Pathology of stage 3 with lesion at prosencephalon. Cortical involvement is confined to the temporal mesocortex (transentorhinal region) and allocortex (CA2-plexus). The neocortex is however, unaffected. |
| Stage five (Neocortex) | Stage 5 and above involved the neocortex. Its lesion include those of stage 4 plus lesions in high order sensory association areas of the neocortex and prefrontal neocortex. |

TABLE 3-continued

Braak staging

| | |
|---|---|
| Stage six (Neocortex) | Pathology of stage 5 plus lesions in first order sensory association areas of the neocortex and premotor areas, occasionally mild changes in primary sensory areas and the primary motor field. |

TABLE 4

Hoehn and Yahr staging

| | |
|---|---|
| Stage one | Symptoms on one side of the body only. |
| Stage two | Symptoms on both sides of the body. No impairment of balance. |
| Stage three | Balance impairment. Mild to moderate disease. Physically independent. |
| Stage four | Severe disability, but still able to walk or stand unassisted. |
| Stage five | Wheelchair-bound or bedridden unless assisted. |

In various embodiments, a patient of the present invention, e.g. a patient having a neurodegenerative condition, e.g., a patient having PD, is a patient that does not have or has not been diagnosed as having a lysosomal storage disease, e.g., a lysosomal storage disease associated with reduced level or activity of a lysosomal enzyme. In various embodiments, a patient of the present invention, e.g. a patient having a neurodegenerative condition, e.g., a patient having PD, is a patient that does not have or has not been diagnosed as having a lysosomal storage disease associated with reduced level or activity of glucocerebrosidase. In certain such embodiments, it is understood that a lysosomal storage disease is a condition diagnosed as being etiologically distinct from the patient's neurodegenerative condition and/or having developed prior to the patient's neurodegenerative condition. In some embodiments, a patient to be treated according to the present invention is a patient that does not have or has not been diagnosed as having any of one or more of the lysosomal storage disease from the group consisting of aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leukodystrophy, mucolipidosis type I, sialidosis types I/II, mucolipidosis types II/III, mucolipidosis type IV, I-cell disease, mucolipidosis type IIIC pseudo-Hurler polydystrophy, mucopolysaccharidosis type I, mucopolysaccharidosis type II, Hunter syndrome, mucopolysaccharidosis type IIIA, Sanfilippo syndrome type A, B, or D (mucopolysaccharidosis type IIIB, mucopolysaccharidosis type IIIC, mucopolysaccharidosis type IIID), mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, Gaucher disease, and sialic acid storage disease.

In some instances, treatment of a neurodegenerative condition of the present invention, e.g., PD, is characterized, evaluated, or recognized according to one or more biomarkers as described herein or known in the art. A biomarker, e.g., a PD-associated biomarker, can have a range or constellation of values. A PD-associated biomarker can have a PD-associated value, range of values, constellation of values, or PD-associated relationship with patient or population normative or control values (e.g., where values above or below a certain standard value are considered to be PD-associated). A PD-associated biomarker can also have a non-PD-associated value, range of values, constellation of values, or non-PD-associated relationship with a patient or population normative or control values. In some instances, treatment will encompass the change or trend in the temporal mean, mode, or moment-to-moment value of a biomarker from a PD-associated value to or toward a non-PD-associated value. Moreover, a biomarker may be measured in the course of determining disease progress and/or treatment progress or efficacy.

Biomarkers of PD can include, without limitation, information obtained through imaging techniques and the analysis of patient samples. For instance, cerebrospinal fluid biomarkers, serum biomarkers, plasma biomarkers, microRNA biomarkers, DNA biomarkers, or protein biomarkers. In particular instances, a biomarker is the concentration of α-synuclein in bodily fluids, e.g., in cerebrospinal fluid, serum, or saliva. In particular instances, a low concentration of α-synuclein in cerebrospinal fluid, serum, or saliva may be indicative of disease. In certain instances, a high concentration of α-synuclein in cerebrospinal fluid, serum, or saliva may be indicative of disease. In certain instances, a biomarker is one or more particular forms of α-synuclein, e.g., phospho-α-synuclein or monomeric-α-synuclein. In certain instances, antibodies against α-synuclein are a biomarker of disease. In various instances, a biomarker can be total tau protein, phosphorylated tau, amyloid β peptide 1-42 (Aβ-42), Aβ-42/t-tau, brain-derived neurotrophic factor (BDNF), Flt3 ligand, or fractalkine levels in a bodily fluid, e.g., cerebrospinal fluid, serum, or saliva. Where applicable, biomarkers provided herein may be measured in a sample, e.g., of serum, saliva, or cerebrospinal fluid. In certain instances, a biomarker is dopamine or a related species or a dopamine receptor. For instance, a biomarker can be the expression of dopamine D2 and/or D3 receptors in peripheral blood lymphocytes, e.g., wherein a decrease is associated with disease. In some instances, a biomarker is a metabolite or constellation of two or more metabolites, e.g., as measured by a method of metabolomics. In particular instances, a biomarker is the ratio of xanthine to homovallinic acid, e.g., where increased xanthine/homovallinic acid ratio is associated with disease.

In some instances, a biomarker of disease is the level of glucosylceramide or glucosylsphingosine. In particular examples, a biomarker of disease is the level of glucosylceramide. In particular examples, a biomarker of disease is the level of glucosylsphingosine. In some examples, the level of one or both of glucosylceramide and glucosylsphingosine are both measured, where, e.g., each measure is individually a biomarker of disease or are together a biomarker of disease.

In some instances, a biomarker of disease is measured in serum and/or CSF.

In some instances, a biomarker is the level of glucosylceramide in one or both of the serum and CSF. In some examples, the level of glucosylceramide is measured in both serum and CSF, where, e.g., each measure is individually a biomarker of disease or the measures are together a biomarker of disease.

In some instances, a biomarker is the level of glucosylsphingosine in one or both of the serum and CSF. In some examples, the level of glucosylsphingosine is measured in both serum and CSF, where, e.g., each measure is individually a biomarker of disease or the measures are together a biomarker of disease.

In some examples, the level of one or both of glucosylceramide and glucosylsphingosine are measured in both serum and/or CSF, where, e.g., each measure is individually a biomarker of disease or the measures are together a biomarker of disease.

In some instances, a biomarker is the level of glucocerebrosidase enzyme in one or both of the serum and CSF. In some examples, the level of glucocerebrosidase enzyme is measured in both serum and CSF, where, e.g., each measure is individually a biomarker of disease or the measures are together a biomarker of disease. In some instances, a biomarker of disease is a biomarker associated with inflammation, e.g., systemic inflammation. For instance, high-sensitivity C-reactive protein (hs-CRP), e.g. a high level of hs-CRP, can be associated with disease.

A biomarker can be a nucleic acid, e.g., a nucleic acid present in a bodily fluid sample. In certain instances, a biomarker is a micro RNA, such as miR-1, miR-22,] miR-29, miR-16-2, miR-26a2, or miR30a.

Biomarkers of the present invention include protein or RNA diagnostic or generic sequencing results. Insofar as the targeted or bulk sequencing of protein or RNA, e.g., protein or RNA from a sample from a subject, e.g., a sample of spinal fluid, serum, saliva, or other tissue, can provide a biomarker of PD. For instance, the expression of one or more particular RNA molecules or a constellation of RNA molecules may be recognized as a biomarker of PD or other neurodegenerative disease or condition.

Another biomarker of neurodegenerative disease can be idiopathic Rapid Eye Movement sleep behavior disorder (iRBD). In some instances, a biomarker is postprandial ghrelin response.

Biomarkers of the present invention include those assayed using imaging techniques. For instance, a biomarker may be brain imaging using 123I-ioflupane ligand with single-photon emission computed tomography. Other biomarkers may relate to imaging of the brain, e.g. the substantia nigra, by methods such as ultrasound, MM, pseudocontinuous arterial spin labeling, electroencephalograms (EEG), or diffusion tensor imaging (e.g., using a 4 Tesla magnetic field). Imaging can be used to measure characteristics including anisotropy. In some instances, a biomarker of the present invention is a biomarker assayed by quantitative EEG (QEEG) methods, e.g., low background rhythm frequency (e.g., lower than 8.5 Hz). In some instances, a biomarker of the present invention is a biomarker assayed by single-photon emission computed tomography (SPECT), positron emission tomography (PET), or functional magnetic resonance imaging (fMRI). In particular instances, e.g., a dopamine transporter (DAT) is imaged.

In some instances, a biomarker is assayed by uptake of a tracer, such as assays including β-CIT uptake measured, e.g., by SPECT, or uptake of $^{18}$F-fluorodopa (18FDOPA). In some instances, a biomarker is measured by magnetic resonance spectroscopy (MRS), e.g., aminobutyric acid (GABA) concentration.

In some instances a biomarker is measured by the computer sampling of motor performance. In other instances, a biomarker is rapid eye movement (REM) behavior disorder (RBD), bowel dysfunction, olfactory deficits, or a mood disorder.

Any of the symptoms of one or more neurodegenerative conditions described herein can be a biomarker of the present invention.

Other biomarkers of the present invention include biomarkers associated with protein degradation or cellular degradative processes. For instance, the conversion of LCII to LCIII can be a biomarker of disease, e.g., PD.

A static biomarker of the present invention can include DNA diagnostic or generic sequencing results. Insofar as certain genetic sequences are associated with an increased risk of PD or other neurodegenerative diseases or conditions, the presence or absence of any such sequence in the genome of an individual, or the presence or absence of any such constellation of sequences in the genome of an individual, can be incorporated into diagnostic or treatment strategies including, e.g., the formulation of therapeutic formulations or regimens.

Other biomarkers are known in the art, including without limitation those studied by the Parkinson's Progression Markers Initiative.

In other instances, a biomarker is the activity, amount, or concentration of glucocerebrosidase enzyme in one or more samples representative of a particular patient. In particular instances, the enzyme is detected by a method of protein analysis, e.g., mass spectrometry or western blot, comparable methods of protein analysis, or other applicable methods of protein analysis known in the art. A wide variety of protein-specific detection methods are known the art. A biomarker may be a measure of the activity or concentration of glucocerebrosidase, e.g., a pharmacokinetic (PK), pharacodynamic (PD), or PK/PD value. A biomarker may be a measure of the activity or concentration of glucocerebrosidase that is a kinetic parameter such as $V_{max}$, $K_m$, $k_{cat}$, or another kinetic parameter known in the art. Enzyme activity assays are known in the art. Similarly, the amount, concentration, or ribosome occupancy of glucocerebrosidase-encoding mRNA, or related measures, in a patient sample may be used as a biomarker in connection with the present invention. Methods of isolating and analyzing mRNA are well known in the art.

In some instances, a biomarker can be a second degree biomarker, i.e., a biomarker of a biomarker. A biomarker may be a combination of one or more biomarkers including any of the above-mentioned biomarkers or others known in the art, e.g., a "fingerprint" of disease.

PD can be diagnosed by a medical practitioner, such as a primary care physician, a specialist such as a neurologist or geriatrician, or other medical practitioner having sufficient knowledge of PD.

The glucocerebrosidase compositions and methods of the present invention can be used to treat (e.g., to cure or ameliorate one or more symptoms of) PD of any degree of severity or any stage, regardless of particular manifestations, symptoms, diagnostic criteria, or difficulty of diagnosis. In particular instances, the compositions and methods of the present invention are effective in subjects refractory to other treatments.

Those of skill in the art will appreciate compositions and methods of the present invention are applicable to other neurodegenerative diseases, including diseases having similarity to PD. Examples of diseases having similarity to PD include, without limitation, multiple system atrophy (MSA), dementia with Lewy bodies, progressive supranuclear palsy, and corticobasal degeneration.

Other diseases or conditions to which compositions and methods of the present invention may be applied, e.g., to treat subjects having the disease or condition, include, without limitation, Neuronopathic Gaucher (Type 2&3), Frontotemporal dementia, and neurodegeneration with brain iron accumulation.

Treatment

The present invention encompasses treatment of neurodegenerative conditions with glucocerebrosidase, e.g., a glucocerebrosidase nucleic acid or protein, described herein. A neurodegenerative condition to be treated by glucocerebrosidase can be PD, e.g., X-linked parkinsonism with spasticity (e.g., PD resulting from or contributed by mutation in the lysosomal proton transporting ATPase, ATP6AP2) or an autosomal dominant form of PD (e.g., PD resulting from or contributed to by a mutation in the VPS35). A neurodegenerative condition to be treated by administration of glucocerebrosidase can be Niemann-Pick disease Type A or Niemann-Pick disease Type B, e.g., Niemann-Pick disease caused or contributed to by a loss-of-function mutation in SMPD1. A neurodegenerative condition to be treated by glucocerebrosidase can be Kufor-Rakeb syndrome or a juvenile or young-onset form of PD (e.g., Kufor-Rakeb syndrome or a juvenile or young-onset form of PD caused or contributed to by a loss-of-function mutation in the cation-transporting ATPase, Adenosine-3-phosphate 13A2 (ATP13A2). Other neurodegenerative conditions as described herein or encompassed by the definition thereof can also be treated by glucocerebrosidase of the present invention. Neurodegenerative diseases that can be treated by the methods and compositions of the present invention include Alzheimer's disease, Huntington's disease, Amyotrophic lateral sclerosis (ALS; also referred to as motor neuron disease (MND), Charcot disease, or Lou Gehrig's disease), progressive supranuclear palsy multiple system atrophy, and Parkinson plus diseases not otherwise mentioned herein.

Those of skill in the art will appreciate the compositions and methods of the present invention are applicable to other neurodegenerative diseases, including diseases having similarity to PD. Examples of diseases having similarity to PD include, without limitation, multiple system atrophy (MSA), dementia with Lewy bodies, progressive supranuclear palsy, and corticobasal degeneration.

Other diseases or conditions to which compositions and methods of the present invention may be applied, e.g., to treat subjects having the disease or condition, include, without limitation, Neuronopathic Gaucher (Type 2&3), Frontotemporal dementia, and neurodegeneration with brain iron accumulation.

A subject having any condition or symptom provided herein is to be recognized as a subject in need of a composition or method of the present invention. Thus, a therapeutic or effective amount of a composition of the present invention may be administered to a subject in need thereof.

It is contemplated that the underlying pathology of PD may significantly predate the involvement of certain clinical symptoms. Accordingly, early diagnosis of PD-associated biomarkers may be used to prompt treatment prior to manifestation of any of one or more of the clinical symptoms provided herein, e.g., prior to the time at which a diagnosis of PD may be achieved through traditional methods. Accordingly, the present invention encompasses treatment prior to diagnosis through traditional methods. Such treatment need not be classified as strictly prophylactic, as biomarkers of aging provide significant basis for determining that a patient is in the process of developing PD not yet diagnosable by traditional methods. In other instances, treatment can be prophylactic. For instance, biomarkers of aging can provide significant basis for determining that a subject is at risk of a later PD diagnosis, prompting treatment. In other instances, treatment will be partially, significantly, or entirely prophylactic. For instance, age itself is a significant risk factor for PD, such that prophylactic treatment of individuals may be appropriate, e.g., individuals greater than 30, 40, 50, 60, 65, 70, 75, 80, 85, or 90 or more years of age.

Treatment of PD or other neurodegenerative conditions as described herein can include improving, inhibiting the progression of, or delaying the onset of one or more symptoms selected from degeneration of dopaminergic neurons (e.g., in the substantia nigra), stiffness of voluntary skeletal muscles, muscle rigidity, tremors, rest tremors, pill-rolling tremors, shaking, bradykinesia, impaired balance, difficulty walking (e.g., festination, characterized by rapid shuffling steps and a forward-flexed posture), altered gait, impaired coordination, akinesia, depression, neuropsychiatric symptoms (e.g., pathological changes in cognition, mood, or behavior), decreased use or presence of facial expressions (e.g., a mask-like facial expression), apathy, anxiety, a state of indifference, quiet speech, impulsive behaviors (such as medication overuse), cravings, binge eating, hypersexuality, pathological gambling, hallucinations, delusions, sleep disturbance, difficulty sleeping, daytime drowsiness, disturbances in REM sleep, Insomnia, dizziness, stooped posture, dementia, dysarthria, dyspnea, dysphagia, loss of dopaminergic innervation, loss of motor activity, accumulation of alpha-synuclein, accumulation of Lewy bodies, difficulty planning movements, difficulty initiating movement, difficulty executing movements, difficulty in the performance of sequential and/or simultaneous movements, difficulty with motor control tasks (e.g., writing, sewing, or dressing), muscle spasticity, progressive weakness, muscle atrophy, difficulty alternating movements between both hands or both feet, balance impairment, postural instability, cognitive executive dysfunction, cognitive difficulty in planning, cognitive difficulty in flexibility, cognitive difficulty in abstract thinking, cognitive difficulty in rule acquisition, cognitive difficulty in initiating appropriate actions, cognitive difficulty in inhibiting inappropriate actions, cognitive difficulty in differentiating relevant from irrelevant sensory information, cognitive difficulty with attention, difficulty in speed of cognition, difficulty with memory, difficulty with recall (e.g., recall of learned information), difficulty with visuospatial perception, difficulty with facial recognition, decreased blink rate, dry eyes, deficient ocular pursuit, saccadic movements, difficulties in directing one's gaze upward, blurred vision, double vision, impaired sense of olfaction, sensation of pain, sensation of paresthesia, orthostatic hypotension, oily skin, excessive sweating, urinary incontinence, altered sexual function, constipation, gastric dysmotility, tendency toward choking, pneumonia, tendency toward falling, requirement for care, requirement for institutionalization, or death. It is not intended that the order of the above symptoms has bearing on the significance of the symptom to the present invention or its scope. Nor is it intended that the inclusion of any species of symptom detract from the scope of any broader term also provided herein. In some instances treatment encompasses a change in the character of one or more symptoms, such as improvement in the bilateral character of one or more symptoms. Other symptoms of PD and other neurodegenerative disorders are known in the art. Treatment further encompasses the modulation of any of or improvement in one or more biomarkers, e.g., a biomarker of PD and/or any biomarker described herein or known in the art.

Treatment of, according to, determined by, or determined in view of one or more symptoms or biomarkers of the present invention is encompassed by the present invention, e.g., where the treatment is the treatment of PD by the administration of a glucocerebrosidase protein or nucleic acid. Treatment that modulates, ameliorates, reduces the severity of, inhibits the onset if, or inhibits the progression of one or more symptoms or biomarkers of the present invention is encompassed by the present invention, e.g., where the treatment is the treatment of PD by the administration of a glucocerebrosidase protein or nucleic acid.

In certain instances glucocerebrosidase gene therapy results in an increase in the amount or concentration of one or both of glucocerebrosidase mRNA or glucocerebrosidase protein in one or more cells, cell types, tissues, organs, or other cell populations. In particular instances, the amount or concentration of one or both of glucocerebrosidase mRNA or glucocerebrosidase protein is increased in the substantia nigra. In particular instances, the amount or concentration of one or both of glucocerebrosidase mRNA or glucocerebrosidase protein is increased in the substantia nigra pars compacta. In particular instances, the amount or concentration of one or both of glucocerebrosidase mRNA or glucocerebrosidase protein is increased in the striatum. In particular instances, the amount or concentration of one or both of glucocerebrosidase mRNA or glucocerebrosidase protein is increased in the hippocampus. In particular instances, the amount or concentration of one or both of glucocerebrosidase mRNA or glucocerebrosidase protein is increased in the substantia nigra and striatum. In particular instances, the amount or concentration of one or both of glucocerebrosidase mRNA or glucocerebrosidase protein is increased in the substantia nigra, striatum, and the hippocampus. In particular instances, the amount or concentration of one or both of glucocerebrosidase mRNA or glucocerebrosidase protein is increased in the substantia nigra and striatum but not in the hippocampus. In particular instances, the amount or concentration of one or both of glucocerebrosidase mRNA or glucocerebrosidase protein is increased in the substantia nigra but not in the striatum or hippocampus. In particular instances, the amount or concentration of one or both of glucocerebrosidase mRNA or glucocerebrosidase protein is increased in the striatum but not in the substantia nigra or hippocampus. In particular instances in which transgenic glucocerebrosidase expression occurs in the substantia nigra, expression may include or be limited to expression in the pars compact or be preferentially expressed in the pars compact. The embodiments of the present invention are not intended to exclude expression of transgenic glucocerebrosidase in any of one or more cells, cell types, tissues, organs, or other cell populations, except where explicitly stated.

In various embodiments of the present invention, the amount or concentration of glucocerebrosidase protein in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In various embodiments of the present invention, the amount or concentration of glucocerebrosidase mRNA in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In certain instances glucocerebrosidase gene therapy results in an increase in the amount or concentration of glucocerebrosidase activity in one or more cells, cell types, tissues, organs, or other cell populations. In particular instances, the amount or concentration of glucocerebrosidase activity is increased in the substantia nigra. In particular instances, the amount or concentration of glucocerebrosidase activity is increased in the substantia nigra pars compacta. In particular instances, the amount or concentration of glucocerebrosidase activity is increased in the striatum. In particular instances, the amount or concentration of glucocerebrosidase activity is increased in the hippocampus. In particular instances, the amount or concentration of glucocerebrosidase activity is increased in the substantia nigra and striatum. In particular instances, the amount or concentration of glucocerebrosidase activity is increased in the substantia nigra, striatum, and the hippocampus. In particular instances, the amount or concentration of glucocerebrosidase activity is increased in the substantia nigra and striatum but not in the hippocampus. In particular instances, the amount or concentration of glucocerebrosidase activity is increased in the substantia nigra but not in the striatum or hippocampus. In particular instances, the amount or concentration of glucocerebrosidase activity is increased in the striatum but not in the substantia nigra or hippocampus. In particular instances in which transgenic glucocerebrosidase expression occurs in the substantia nigra, the increase in glucocerebrosidase activity may include or be limited to expression in the pars compact or be preferentially increased in the pars compact. The embodiments of the present invention are not intended to exclude increased glucocerebrosidase activity in any of one or more cells, cell types, tissues, organs, or other cell populations, except where explicitly stated.

In various embodiments of the present invention, the activity of glucocerebrosidase in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In certain instances glucocerebrosidase gene therapy results in an increase in the amount or concentration of one or more of macroautophagy, macroautophagy-associated protein expression, chaperone-mediated autophagy, and autophagosome formation in one or more cells, cell types, tissues, organs, or other cell populations. In particular instances, the amount or concentration of one or more of macroautophagy, macroautophagy-associated protein expression, chaperone-mediated autophagy, and autophagosome formation is increased in the substantia nigra. In particular instances, the amount or concentration of one or more of macroautophagy, macroautophagy-associated protein expression, chaperone-mediated autophagy, and autophagosome formation is increased in the substantia nigra pars compacta. In particular instances, the amount or concentration of one or more of macroautophagy, macroautophagy-associated protein expression, chaperone-mediated autophagy, and autophagosome formation is increased in the striatum. In particular instances, the amount or concentration of one or more of macroautophagy, macroautophagy-associated protein expression, chaperone-mediated autophagy, and autophagosome formation is increased in the hippocampus. In particular instances, the amount or concentration of one or more of macroautophagy, macroautophagy-associated protein expression, chaperone-mediated autophagy, and autophagosome formation is increased in the substantia nigra and striatum. In particular instances, the amount or concentration of one or more of macroautophagy, macroautophagy-associated protein expression, chaperone-mediated autophagy, and autophagosome formation is increased in the substantia nigra, striatum, and the hippocampus. In particular instances, the amount or concentration of one or more of macroautophagy, macroautophagy-associated protein expression, chaperone-mediated autophagy, and autophagosome formation is increased in the substantia nigra and striatum but not in the hippocampus. In particular instances, the amount or concentration of one or more of macroautophagy, macroautophagy-associated protein expression, chaperone-mediated autophagy, and autophagosome formation is increased in the substantia nigra but not in the striatum or hippocampus. In particular instances, the amount or concentration of one or more of macroautophagy, macroautophagy-associated protein expression, chaperone-mediated autophagy, and autophagosome formation is increased in the striatum but not in the substantia nigra or hippocampus. In particular instances in which transgenic glucocerebrosidase expression occurs in the sub stantia nigra, the increase in the amount or concentration of one or more of macroautophagy, macroautophagy-associated protein expression, chaperone-mediated autophagy, and autophagosome formation may include or be limited to the pars compact or be preferentially increased in the pars compact. The embodiments of the present invention are not intended to exclude an increase of one or more of macroautophagy, macroautophagy-associated protein expression, chaperone-mediated autophagy, and autophagosome formation activity in any of one or more cells, cell types, tissues, organs, or other cell populations, except where explicitly stated.

In various embodiments of the present invention, one or more of macroautophagy, macroautophagy-associated protein expression, chaperone-mediated autophagy, and autophagosome formation in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In certain instances glucocerebrosidase gene therapy results in a decrease in the number, size, amount, or concentration of α-synuclein aggregates (e.g., any of one or more of aggregates of 0-0.5 $\mu m^2$, aggregates of 0.6-1 $\mu m^2$, aggregates of 1.1-1.9 $\mu m^2$, aggregates of 2-5 $\mu m^2$, aggregates of 5.1-5.9 $\mu m^2$, aggregates of 6-10 $\mu m^2$, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species in one or more cells, cell types, tissues, organs, or other cell populations. In particular instances, the number, size, amount, or concentration of α-synuclein aggregates (e.g., any of one or more of aggregates of 0-0.5 µm2, aggregates of 0.6-1 µm2, aggregates of 1.1-1.9 µm2, aggregates of 2-5 µm2, aggregates of 5.1-5.9 µm2, aggregates of 6-10 µm2, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the substantia nigra. In particular instances, the number, size, amount, or concentration of α-synuclein aggregates (e.g., any of one or more of aggregates of 0-0.5 µm2, aggregates of 0.6-1 µm2, aggregates of 1.1-1.9 µm2, aggregates of 2-5 µm2, aggregates of 5.1-5.9 µm2, aggregates of 6-10 µm2, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the substantia nigra pars compacta. In particular instances, the number, size, amount, or concentration of α-synuclein aggregates (e.g., any of one or more of aggregates of 0-0.5 $\mu m^2$, aggregates of 0.6-1 $\mu m^2$, aggregates of 1.1-1.9 $\mu m^2$, aggregates of 2-5 $\mu m^2$, aggregates of 5.1-5.9 $\mu m^2$, aggregates of 6-10 $\mu m^2$, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the striatum. In particular instances, the number, size, amount, or concentration of α-synuclein aggregates (e.g., any of one or more of aggregates of 0-0.5 $\mu m^2$, aggregates of 0.6-1 $\mu m^2$, aggregates of 1.1-1.9 $\mu m^2$, aggregates of 2-5 $\mu m^2$, aggregates of 5.1-5.9 $\mu m^2$, aggregates of 6-10 $\mu m^2$, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the hippocampus. In particular instances, the number, size, amount, or concentration of α-synuclein aggregates (e.g., any of one or more of aggregates of 0-0.5 $\mu m^2$, aggregates of 0.6-1 $\mu m^2$, aggregates of 1.1-1.9 $\mu m^2$, aggregates of 2-5 $\mu m^2$, aggregates of 5.1-5.9 $\mu m^2$, aggregates of 6-10 $\mu m^2$, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the substantia nigra and striatum. In particular instances, the number, size, amount, or concentration of α-synuclein aggregates (e.g., any of one or more of aggregates of 0-0.5 $\mu m^2$, aggregates of 0.6-1 $\mu m^2$, aggregates of 1.1-1.9 $\mu m^2$, aggregates of 2-5 $\mu m^2$, aggregates of 5.1-5.9 $\mu m^2$, aggregates of 6-10 $\mu m^2$, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the substantia nigra, striatum, and the hippocampus. In particular instances, the number, size, amount, or concentration of α-synuclein aggregates (e.g., any of one or more of aggregates of 0-0.5 $\mu m^2$, aggregates of 0.6-1 $\mu m^2$, aggregates of 1.1-1.9 $\mu m^2$, aggregates of 2-5 $\mu m^2$, aggregates of 5.1-5.9 $\mu m^2$, aggregates of 6-10 $\mu m^2$, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the substantia nigra and striatum but not in the hippocampus. In particular instances, the number, size, amount, or concentration of α-synuclein aggregates (e.g., any of one or more of aggregates of 0-0.5 $\mu m^2$, aggregates of 0.6-1 $\mu m^2$, aggregates of 1.1-1.9 $\mu m^2$, aggregates of 2-5 $\mu m^2$, aggregates of 5.1-5.9 $\mu m^2$, aggregates of 6-10 $\mu m^2$, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the substantia nigra but not in the striatum or hippocampus. In particular instances, the number, size, amount, or concentration of α-synuclein aggregates (e.g., any of one or more of aggregates of 0-0.5 $\mu m^2$, aggregates of 0.6-1 $\mu m^2$, aggregates of 1.1-1.9 $\mu m^2$, aggregates of 2-5 $\mu m^2$, aggregates of 5.1-5.9 $\mu m^2$, aggregates of 6-10 $\mu m^2$, aggregates of 0-10 $\mu m^2$, aggregates of 11-20 $\mu m^2$, aggregates of 21-50 $\mu m^2$, aggregates of 51-99 $\mu m^2$, aggregates of 100 or more $\mu m^2$, or total aggregates) or α-synuclein oligomeric species is decreased in the striatum but not in the substantia nigra or hippocampus. In particular instances in which the number, size, amount, or concentration of α-synuclein aggregates (e.g., any of one or more of aggregates of 0-0.5 μm², aggregates of 0.6-1 μm², aggregates of 1.1-1.9 μm², aggregates of 2-5 μm², aggregates of 5.1-5.9 μm², aggregates of 6-10 μm², aggregates of 0-10 μm², aggregates of 11-20 μm², aggregates of 21-50 μm², aggregates of 51-99 μm², aggregates of 100 or more μm², or total aggregates) or α-synuclein oligomeric species is decreased in the substantia nigra, the decrease in the number, size, amount, or concentration of α-synuclein aggregates (e.g., any of one or more of aggregates of 0-0.5 μm², aggregates of 0.6-1 μm², aggregates of 1.1-1.9 μm², aggregates of 2-5 μm², aggregates of 5.1-5.9 μm², aggregates of 6-10 μm², aggregates of 0-10 μm², aggregates of 11-20 μm², aggregates of 21-50 μm², aggregates of 51-99 μm², aggregates of 100 or more μm², or total aggregates) or α-synuclein oligomeric species may include or be limited to expression in the pars compact or be particularly great in the pars compact. The embodiments of the present invention are not intended to exclude decrease in the number, size, amount, or concentration of α-synuclein aggregates (e.g., any of one or more of aggregates of 0-0.5 μm², aggregates of 0.6-1 μm², aggregates of 1.1-1.9 μm², aggregates of 2-5 μm², aggregates of 5.1-5.9 μm², aggregates of 6-10 μm², aggregates of 0-10 μm², aggregates of 11-20 μm², aggregates of 21-50 μm², aggregates of 51-99 μm², aggregates of 100 or more μm², or total aggregates) or α-synuclein oligomeric species in any of one or more cells, cell types, tissues, organs, or other cell populations, except where explicitly stated. In any particular embodiment, the α-synuclein can be one or more of the total of high molecular weight α-synuclein, proteinase-K resistant insoluble α-synuclein, or other α-synuclein.

In various embodiments of the present invention, the number, size, amount, or concentration of α-synuclein aggregates (e.g., any of one or more of aggregates of 0-0.5 μm², aggregates of 0.6-1 μm², aggregates of 1.1-1.9 μm², aggregates of 2-5 μm², aggregates of 5.1-5.9 μm², aggregates of 6-10 μm², aggregates of 0-10 μm², aggregates of 11-20 μm², aggregates of 21-50 μm², aggregates of 51-99 μm², aggregates of 100 or more μm², or total aggregates) or α-synuclein oligomeric species in any of one or more cells, cell types, tissues, organs, or other cell populations is decreased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In certain instances glucocerebrosidase gene therapy results in an increase in the conversion of LC3-I to LC3-II in one or more cells, cell types, tissues, organs, or other cell populations. In particular instances, the conversion of LC3-I to LC3-II is increased in the substantia nigra. In particular instances, the conversion of LC3-I to LC3-II is increased in the substantia nigra pars compacta. In particular instances, the conversion of LC3-I to LC3-II is increased in the striatum. In particular instances, the conversion of LC3-I to LC3-II is increased in the hippocampus. In particular instances, the conversion of LC3-I to LC3-II is increased in the substantia nigra and striatum. In particular instances, the conversion of LC3-I to LC3-II is increased in the substantia nigra, striatum, and the hippocampus. In particular instances, the conversion of LC3-I to LC3-II is increased in the substantia nigra and striatum but not in the hippocampus. In particular instances, the conversion of LC3-I to LC3-II is increased in the substantia nigra but not in the striatum or hippocampus. In particular instances, the conversion of LC3-I to LC3-II is increased in the striatum but not in the substantia nigra or hippocampus. In particular instances in conversion of LC3-I to LC3-II is increased in the substantia nigra, the increase may include or be limited to expression in the pars compact or be particularly great in the pars compact. The embodiments of the present invention are not intended to exclude increased conversion of LC3-I to LC3-II in any of one or more cells, cell types, tissues, organs, or other cell populations, except where explicitly stated.

In various embodiments of the present invention, the conversion of LC3-I to LC3-II in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In certain instances glucocerebrosidase gene therapy results in an increase in the amount or concentration of LC3-II in one or more cells, cell types, tissues, organs, or other cell populations. In particular instances, the amount or concentration of LC3-II is increased in the substantia nigra. In particular instances, the amount or concentration of LC3-II is increased in the substantia nigra pars compacta. In particular instances, the amount or concentration of LC3-II is increased in the striatum. In particular instances, the amount or concentration of LC3-II is increased in the hippocampus. In particular instances, the amount or concentration of LC3-II is increased in the substantia nigra and striatum. In particular instances, the amount or concentration of LC3-II is increased in the substantia nigra, striatum, and the hippocampus. In particular instances, the amount or concentration of LC3-II is increased in the substantia nigra and striatum but not in the hippocampus. In particular instances, the amount or concentration of LC3-II is increased in the substantia nigra but not in the striatum or hippocampus. In particular instances, the amount or concentration of LC3-II is increased in the striatum but not in the substantia nigra or hippocampus. In particular instances in which the increase in LC3-II occurs in the substantia nigra, the increase in LC3-II may include or be limited to expression in the pars compact or be particularly great in the pars compact. The embodiments of the present invention are not intended to exclude increased LC3-II in any of one or more cells, cell types, tissues, organs, or other cell populations, except where explicitly stated.

In various embodiments of the present invention, the amount or concentration of LC3-II in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In certain instances glucocerebrosidase gene therapy results in an increase in the amount or concentration of any of one or more of beclin-1, LAMP-2A, and ceramide in one or more cells, cell types, tissues, organs, or other cell populations. In particular instances, the amount or concentration of any of one or more of beclin-1, LAMP-2A, and ceramide is increased in the substantia nigra. In particular instances, the amount or concentration of any of one or more of beclin-1, LAMP-2A, and ceramide is increased in the substantia nigra pars compacta. In particular instances, the amount or concentration of any of one or more of beclin-1, LAMP-2A, and ceramide is increased in the striatum. In particular instances, the amount or concentration of any of one or more of beclin-1, LAMP-2A, and ceramide is increased in the hippocampus. In particular instances, the amount or concentration of any of one or more of beclin-1, LAMP-2A, and ceramide is increased in the substantia nigra and striatum. In particular instances, the amount or concentration of any of one or more of beclin-1, LAMP-2A, and ceramide is increased in the substantia nigra, striatum, and the hippocampus. In particular instances, the amount or concentration of any of one or more of beclin-1, LAMP-2A, and ceramide is increased in the substantia nigra and striatum but not in the hippocampus. In particular instances, the amount or concentration of any of one or more of beclin-1, LAMP-2A, and ceramide is increased in the substantia nigra but not in the striatum or hippocampus. In particular instances, the amount or concentration of any of one or more of beclin-1, LAMP-2A, and ceramide is increased in the striatum but not in the substantia nigra or hippocampus. In particular instances in which any of one or more of beclin-1, LAMP-2A, and ceramide are increased in the substantia nigra, an increase in the amount or concentration of any of one or more of beclin-1, LAMP-2A, and ceramide activity may include or be limited to the pars compact or be particularly great in the pars compact. The embodiments of the present invention are not intended to exclude an increase in the amount or concentration of beclin-1, LAMP-2A, and/or ceramide in any of one or more cells, cell types, tissues, organs, or other cell populations, except where explicitly stated.

In various embodiments of the present invention, the increase in the amount or concentration of any of one or more of beclin-1, LAMP-2A, and ceramide in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In certain instances glucocerebrosidase gene therapy is neuroprotective (e.g., prevents neurodegeneration). In particular instances, glucocerebrosidase gene therapy is neuroprotective for one or more neurons of the substantia nigra. In particular instances, glucocerebrosidase gene therapy is neuroprotective for one or more neurons of the substantia nigra pars compacta. In particular instances, glucocerebrosidase gene therapy is neuroprotective for one or more neurons of the striatum. In particular instances, glucocerebrosidase gene therapy is neuroprotective for one or more neurons of the hippocampus. In particular instances, glucocerebrosidase gene therapy is neuroprotective for one or more neurons of the substantia nigra and striatum. In particular instances, glucocerebrosidase gene therapy is neuroprotective for one or more neurons of the substantia nigra, striatum, and hippocampus. In particular instances, glucocerebrosidase gene therapy is neuroprotective for one or more neurons of the substantia nigra and striatum but not of the hippocampus. In particular instances, glucocerebrosidase gene therapy is neuroprotective for one or more neurons of the substantia nigra but not of the striatum or hippocampus. In particular instances, glucocerebrosidase gene therapy is neuroprotective for one or more neurons of the striatum but not of the substantia nigra or hippocampus. In particular instances in which glucocerebrosidase gene therapy is neuroprotective for one or more neurons of the substantia nigra, the protection may include or be limited to the pars compact or be particularly great in neurons of the pars compact. The embodiments of the present invention are not intended to exclude neuroprotection of neurons of in any of one or more tissues, except where explicitly stated. In any of the above embodiments, protected neurons can include any of one or more of dopaminergic DA neurons (e.g., DA neurons of the substantia nigra), DA neurons of the substantia nigra pars compacta, nigrostriatal dopaminergic neurons, DA neurons of the nigrostriatal pathway, and TH-positive DA neurons.

In certain instances glucocerebrosidase gene therapy results in a decrease in the number, concentration, or phenotypic severity of swollen axons, bulging axons, and/or axons that are both swollen and bulging in one or more cells, cell types, tissues, organs, or other cell populations. In particular instances, the amount or concentration of the number, concentration, or phenotypic severity of swollen axons, bulging axons, and/or axons that are both swollen and bulging is increased in the substantia nigra. In particular instances, the number, concentration, or phenotypic severity of swollen axons, bulging axons, and/or axons that are both swollen and bulging is decreased in the substantia nigra pars compacta. In particular instances, the number, concentration, or phenotypic severity of swollen axons, bulging axons, and/or axons that are both swollen and bulging is decreased in the striatum. In particular instances, the number, concentration, or phenotypic severity of swollen axons, bulging axons, and/or axons that are both swollen and bulging is decreased in the hippocampus. In particular instances, the number, concentration, or phenotypic severity of swollen axons, bulging axons, and/or axons that are both swollen and bulging is decreased in the substantia nigra and striatum. In particular instances, the number, concentration, or phenotypic severity of swollen axons, bulging axons, and/or axons that are both swollen and bulging is decreased in the substantia nigra, striatum, and the hippocampus. In particular instances, the number, concentration, or phenotypic severity of swollen axons, bulging axons, and/or axons that are both swollen and bulging is decreased in the substantia nigra and striatum but not in the hippocampus. In particular instances, the number, concentration, or phenotypic severity of swollen axons, bulging axons, and/or axons that are both swollen and bulging is decreased in the substantia nigra but not in the striatum or hippocampus. In particular instances, the number, concentration, or phenotypic severity of swollen axons, bulging axons, and/or axons that are both swollen and bulging is decreased in the striatum but not in the substantia nigra or hippocampus. In particular instances in which the number, concentration, or phenotypic severity of swollen axons, bulging axons, and/or axons that are both swollen and bulging is decreased in the substantia nigra, the decrease may include or be limited to expression in the pars compact or be particularly great in the pars compact. The embodiments of the present invention are not intended to exclude decreased number, concentration, or phenotypic severity of swollen axons, bulging axons, and/or axons that are both swollen and bulging in any of one or more cells, cell types, tissues, organs, or other cell populations, except where explicitly stated.

In various embodiments of the present invention, the decrease in the number, concentration, or phenotypic severity of swollen axons, bulging axons, and/or axons that are both swollen and bulging in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

In certain instances glucocerebrosidase gene therapy results in an increase in the amount or concentration of ubiquitin-like protein p62 in one or more cells, cell types, tissues, organs, or other cell populations. In particular instances, the amount or concentration of ubiquitin-like protein p62 is increased in the substantia nigra. In particular instances, the amount or concentration of ubiquitin-like protein p62 is increased in the substantia nigra pars compacta. In particular instances, the amount or concentration of ubiquitin-like protein p62 is increased in the striatum. In particular instances, the amount or concentration of ubiquitin-like protein p62 is increased in the hippocampus. In particular instances, the amount or concentration of ubiquitin-like protein p62 is increased in the substantia nigra and striatum. In particular instances, the amount or concentration of ubiquitin-like protein p62 is increased in the substantia nigra, striatum, and the hippocampus. In particular instances, the amount or concentration of ubiquitin-like protein p62 is increased in the substantia nigra and striatum but not in the hippocampus. In particular instances, the amount or concentration of ubiquitin-like protein p62 is increased in the substantia nigra but not in the striatum or hippocampus. In particular instances, the amount or concentration of ubiquitin-like protein p62 is increased in the striatum but not in the substantia nigra or hippocampus. In particular instances in which increased amount or concentration of ubiquitin-like protein p62 occurs in the substantia nigra, the increase may include or be limited to the pars compact or be particularly great in the pars compact. The embodiments of the present invention are not intended to exclude increased ubiquitin-like protein p62 in any of one or more cells, cell types, tissues, organs, or other cell populations, except where explicitly stated.

In various embodiments of the present invention, the amount or concentration of ubiquitin-like protein p62 in any of one or more cells, cell types, tissues, organs, or other cell populations is increased by 5%, 10%, 20%, 30%, 40%, 50%, 60%, 70%, 80%, 90%, 100%, 150%, 2-fold, 3-fold, 4-fold, 5-fold, 10-fold, or more, or any range therebetween.

Compositions and methods of the present invention are applicable to the treatment of PD and other neurodegenerative conditions in human subjects. Compositions and methods of the present invention may also be useful in the treatment of animals, such as non-human primates, livestock, and domestic animals. For example, compositions and methods of the present invention may be applicable to cats, dogs, chickens, horses, cows, sheep, goats, and other animals known to those of skill in the art.

Numerous factors may be considered in determining an appropriate dosage of a glucocerebrosidase nucleic acid for use in treating a subject. The level of protein expression, localization of protein expression, severity of subject's condition (e.g., PD), stage of subject's condition (e.g., PD), age of subject, health of subject, clinical history of subject, sex of subject, and other factors may all be taken into consideration in the determination of proper treatment regimens, including formulations and dosages.

While dosages may vary depending on the disease and the patient, the targeted dose of glucocerebrosidase protein is generally from about 0.1 to about 1000 milligrams per 50 kg of patient each administration. Dosage may be administered repeated, e.g., weekly, monthly, or at other time intervals, or as needed. In certain embodiments, the polypeptide is administered to a subject in amounts of about 1 to about 500 milligrams per 50 kg per month. In other embodiments, the polypeptide is administered to the patient in amounts of about 5 to about 300 milligrams per 50 kg per month, or about 10 to about 200 milligrams per 50 kg of patient per month. Depending on the type and severity of the disease, a targeted systemic or local concentration of glucocerebrosidase protein may be about 100 pg/ml to about 100 µg/ml, 1 ng/ml to about 95 µg/ml, 10 ng/ml to about 85 µg/ml, 100 ng/ml to about 75 µg/ml, from about 100 ng/ml to about 50 µg/ml, from about 1 µg/ml to about 25 µg/ml, from about 1 µg/ml to about 15 µg/ml, from about 1 µg/ml to about 10 µg/ml, or from about 1 µg/ml to about 4 µg/ml.

Glucocerebrosidase proteins can be administered by protein or chemical therapy, in which instance the dose can be from about 0.1 mg to about 50 mg, from about 0.1 mg to about 25 mg, from about 0.1 mg to about 10 mg, from about 0.5 mg to about 5 mg, or from about 0.5 mg to about 2.5 mg per unit dose.

With respect to gene therapy, a glucocerebrosidase nucleic acid, such as a viral-based glucocerebrosidase nucleic acid, can be administered at a dosage, e.g., of $2 \times 10^6$ to $2 \times 10^{12}$ DNA-containing viral particles, e.g., AAV particles, $2 \times 10^7$ to $2 \times 10^{11}$ particles, or $2 \times 10^8$ to $2 \times 10^{11}$ particles per dose.

In certain embodiments, the concentration or titer of the vector in a unit dosage form at least: (a) $1 \times 10^{12}$ particles per ml, $2 \times 10^{12}$ particles per ml, $3 \times 10^{12}$ particles per ml, $4 \times 10^{12}$ particles per ml, $5 \times 10^{12}$ particles per ml, $6 \times 10^{12}$ particles per ml, $7 \times 10^{12}$ particles per ml, $8 \times 10^{12}$ particles per ml, $9 \times 10^{12}$ particles per ml, $10 \times 10^{12}$ particles per ml, $15 \times 10^{12}$ particles per ml, $20 \times 10^{12}$ particles per ml, $25 \times 10^{12}$ particles per ml, or $50 \times 10^{12}$ particles per ml; (b) $1 \times 10^9$ TU/ml, $2 \times 10^9$ TU/ml, $3 \times 10^9$ TU/ml, $4 \times 10^9$ TU/ml, $5 \times 10^9$ TU/ml, $6 \times 10^9$ TU/ml, $7 \times 10^9$ TU/ml, $8 \times 10^9$ TU/ml, $9 \times 10^9$ TU/ml, $10 \times 10^9$ TU/ml, $15 \times 10^9$ TU/ml, $20 \times 10^9$ TU/ml, 25, or $50 \times 10^9$ TU/ml; or (c) $1 \times 10^{10}$ IU/ml, $2 \times 10^{10}$ IU/ml, $3 \times 10^{10}$ IU/ml, $4 \times 10^{10}$ IU/ml, $5 \times 10^{10}$ IU/ml, $6 \times 10^{10}$ IU/ml, $7 \times 10^{10}$ IU/ml, $8 \times 10^{10}$ IU/ml, $9 \times 10^{10}$ IU/ml, $10 \times 10^{10}$ IU/ml, $15 \times 10^{10}$ IU/ml, $20 \times 10^{10}$ IU/ml, $25 \times 10^{10}$ IU/ml, or $50 \times 10^{10}$ IU/ml. Those of skill in the art will appreciate that such embodiments do not limit the unit dosages encompassed by the present invention and do not limit the various measures of dosage that may be used in conjunction with various compositions of the present invention. For instance, a particle dosage, concentration, or amount may be measured and/or expressed in terms of vector genomes per kilogram subject (Vg/Kg) or Vg/dose. The preferred means of measuring and/or expressing particle dosage, concentration, or amount may vary depending upon various factors, e.g., route of administration.

In some instances, the dosage of a formulation for administration to humans is measured by volume. For example, in a composition for administration by real time convection enhanced delivery, volumes could be, e.g., 100 to 1,000 microliters per striatum in one or several injections. In another example, in a composition for administration by stereotactic administration, a delivery volume of up to, e.g., 300 µL may be used. This could be the case, e.g., for the administration of an AAV2 construct by direct injection into the striatum or into the substantia nigra. In some instances, injection into the striatum would be administered with the intent of retrograde transport to the substantia nigra.

In certain instances, an AAV is administered at a dose of $10^{14}$/kg body weight, although total dose may depend on the route of administration. For example, in some instances of administration by systemic delivery, up to $10^{13}$ particles/kg to $5 \times 10^{"}$ particles/kg can be used. In some instances of intrathecal administration into the CSF, a volume of $10^{13}$ virus particles may be administered. Various routes of intracranial administration include administration into the cisterna magna, intracerebroventricularly, or intraparenchymal, e.g., into the striatum or directly into the substantia nigra. Direct administration to the substantia nigra can sometimes include a smaller volume dosage and can involve certain technical challenges. Examples of the use of AAV vectors in clinical trials can be found, e.g., in Clinical Trial NCT01973543 (Bankiewicz, AADC Gene Therapy for Parkinson's Disease) and Clinical Trial NCT01621581 (National Institute of Neurological Disorders and Stroke (NINDS), AAV2-GDNF for Advanced Parkinson s Disease), which are herein incorporated by reference.

The terms "genome particles (gp)," or "genome equivalents," as used in reference to a viral titer, refer to the number of virions containing the recombinant viral genome, e.g., recombinant AAV DNA genome, regardless of infectivity or functionality. The number of genome particles in a particular vector preparation can be measured by procedures known in the art. The terms "infection unit (IU)," "infectious particle," or "replication unit," as used in reference to a viral titer, refer to the number of infectious and replication-competent recombinant virus, e.g., of recombinant AAV vector particles, as can be measured by the infectious center assay, also known as replication center assay, as well as other methods known in the art. The term "transducing unit (tu)" as used in reference to a viral titer, refers to the number of infectious recombinant vector particles, e.g., recombinant AAV vector particles, that result in the production of a functional transgene product as measured by methods known in the art.

Compositions of the present invention can include a glucocerebrosidase protein or nucleic acid and, optionally, a carrier or other material, e.g., one or more inert components (for example, a detectable agent or label) or one or more active components. Compositions of the present invention can include components such as adjuvants, diluents, binders, stabilizers, buffers, salts, lipophilic solvents, preservatives, mixtures thereof, or any component known in the art for inclusion in therapeutic compositions.

Carriers can be pharmaceutically acceptable carriers such as excipients, additives, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers). A composition of the present invention that includes carriers can include one or more carriers that comprise, singly or in combination, 1-99.99% by weight or volume of the composition. Excipients, e.g., for use in a proteinaceous composition, can include serum albumin such as human serum albumin (HSA), recombinant human albumin (rHA), gelatin, casein, and related agents known in the art. Amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. The compositions of the present invention can also include carbohydrate excipients, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myo-inositol.

Carriers can also encompass a buffer or a pH adjusting agent. A buffer can be a salt prepared from an organic acid or base. Buffers of the present invention include organic acid salts such as salts of citric acid, ascorbic acid, gluconic acid, carbonic acid, tartaric acid, succinic acid, acetic acid, or phthalic acid, Tris, tromethamine hydrochloride, and phosphate buffers. Additional carriers include polymeric excipients or additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as TWEEN 20® and TWEEN 80®), lipids (e.g., phospholipids, fatty acids), steroids (e.g., cholesterol), and chelating agents (e.g., EDTA).

As used herein, the term "pharmaceutically acceptable carrier" encompasses any known pharmaceutical carrier or carriers, including saline, solvents, dispersion media, coatings, antibacterial and antifungal agents, isotonic and absorption delaying agents, and the like, a phosphate buffered saline solution, water, and emulsions, such as an oil/water or water/oil emulsion, and various types of wetting agents, compatible with pharmaceutical administration. Supplementary active compounds can also be incorporated into compositions of the present invention. Compositions of the present invention can include stabilizers and preservatives and any of the carriers described herein with the optional additional proviso that they be acceptable for use in vivo. For examples of additional carriers, stabilizers, and adjuvants, see Martin REMINGTON'S PHARM. SCI., 15th Ed. (Mack Publ. Co., Easton (1975) and Williams & Williams, (1995), and in the "PHYSICIAN'S DESK REFERENCE," 52nd ed., Medical Economics, Montvale, N.J. (1998). In addition, the compositions described herein can include agents that increase the level or activity of glucocerebrosidase.

The methods described herein include the manufacture and use of pharmaceutical compositions. Pharmaceutical compositions are typically formulated to be compatible with their intended route of administration. Examples of routes of administration include parenteral, e.g., intravenous, intracranial, intradermal, subcutaneous, oral (e.g., inhalation), transdermal (topical), transmucosal, and rectal administration.

Methods of formulating pharmaceutical compositions are known in the art, see, e.g., the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. Parenteral preparations can be enclosed, e.g., in ampoules, disposable syringes, or multiple dose vials made of glass or plastic.

Pharmaceutical compositions suitable for injection can include sterile aqueous solutions or dispersions and sterile powders for the extemporaneous preparation of sterile injectable solutions or dispersion. For intravenous administration, suitable carriers can include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof.

Sterility, stability, viscosity and other factors relating to effective therapeutic use can be considered. One method of maintaining fluidity, for example, includes the use of a coating such as lecithin, the maintenance of required particle size, or the use of surfactants. In some instances, it will be preferable to include isotonic agents, for example, sugars, polyalcohols such as mannitol, sorbitol, sodium chloride in the composition. In some instances, prolonged absorption of injectable compositions can be brought about by including in the composition an agent that delays absorption, for example, aluminum monostearate and gelatin.

Sterile injectable solutions can be prepared by incorporating one or a combination of ingredients such as antibacterial and antifungal agents (for example, parabens, chlorobutanol, phenol, ascorbic acid, thimerosal, and the like), and/or by filtered sterilization. In some instances, dispersions are prepared by incorporating the active compound into a sterile vehicle, which contains a basic dispersion medium and antibacterial or antifungal agents. In the case of sterile powders for the preparation of sterile injectable solutions, methods of preparation include vacuum drying and freeze-drying from a previously sterile-filtered solution thereof.

Oral compositions can include an inert diluent or an edible carrier. For the purpose of oral therapeutic administration, glucocerebrosidase can be incorporated with excipients and used, e.g., in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Sterotes®; a glidant such as colloidal silicon dioxide; a sweetening agent such as sucrose or saccharin; or a flavoring agent such as peppermint, methyl salicylate, or orange flavoring.

Glucocerebrosidase can also be prepared for administration by inhalation, e.g., delivery in the form of an aerosol spray from a pressured container or dispenser that contains a suitable propellant, e.g., a gas such as carbon dioxide, or a nebulizer. Such methods include those described, e.g., in U.S. Pat. No. 6,468,798.

Glucocerebrosidase can be administered systematically. Systemic administration of a glucocerebrosidase composition can be by transmucosal or transdermal means. For transmucosal or transdermal administration, penetrants appropriate to the barrier to be permeated can be used in a transmucosal or transdermal therapeutic formulation. Such penetrants are generally known in the art, and include, for example, detergents, bile salts, and fusidic acid derivatives. Transmucosal administration can be accomplished through the use of nasal sprays or suppositories. For transdermal administration, glucocerebrosidase can be formulated or incorporated into ointments, salves, gels, or creams, with respect to which methods and examples are known in the art.

Glucocerebrosidase compositions can also be prepared in the form of suppositories (e.g., with conventional suppository bases such as cocoa butter and other glycerides) or retention enemas for rectal delivery.

In particular embodiments, glucocerebrosidase nucleic acids can be administered by any method suitable for administration of nucleic acid agents, such as a DNA vaccine. These methods include, e.g., gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, e.g., Hamajima et al., (1998) Clin. Immunol. Immunopathol. 88(2), 205-10. Liposomes (e.g., as described in U.S. Pat. No. 6,472,375). In certain instances, microencapsulation can be used. In addition, biodegradable targetable microparticle delivery systems can be used (e.g., as described in U.S. Pat. No. 6,471,996).

In certain embodiments, glucocerebrosidase therapeutic compositions are prepared with carriers capable of protecting the glucocerebrosidase against rapid elimination from the body. Such embodiments can include controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using techniques known in the art using materials that can be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In certain embodiments, a glucocerebrosidase composition, such as a glucocerebrosidase nucleic acid or glucocerebrosidase protein, is administered by a method that directs the composition to the central nervous system. In some instances, techniques or routes can be used for CNS delivery of a glucocerebrosidase protein or nucleic acid of the present invention including, without limitation, intraparenchymal, intracerebral, intraventricular cerebral (ICV), intrathecal (e.g., IT-Lumbar, IT-cisterna magna) administrations and any other techniques and routes for directly or indirectly injecting a glucocerebrosidase protein or nucleic acid to the CNS and/or cerebrospinal fluid (CSF).

Additional methods of delivering compositions to the central nervous system are known in the art. In particular instances, a glucocerebrosidase composition, such as a glucocerebrosidase nucleic acid or glucocerebrosidase protein, is administered according to the formulations and/or methods described in U.S. patent publication 2012-0003202, which is herein incorporated by reference in its entirety, or U.S. Pat. No. 8,545,837, which is herein incorporated by reference in its entirety. In particular embodiments a glucocerebrosidase composition is delivered to the central nervous system by intrathecal administration.

Intrathecal Administration

In various embodiments of the present invention, a glucocerebrosidase protein or nucleic acid is administered by a means that facilitates delivery to the central nervous system, to the brain, or to one or more tissues or regions of the brain. Such means are described, e.g., in U.S. patent publications 2012-0003202, 2013-0295071, and 2013-0295077, each of which is herein incorporated by reference in its entirety.

As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

A glucocerebrosidase protein or nucleic acid can, in some embodiments, be directly introduced into the cerebrospinal fluid (CSF) of a subject in need of treatment at a high concentration such that, e.g., the protein or nucleic acid effectively and extensively diffuses across various surfaces and penetrates various regions across the brain, including deep brain regions. In certain instances, delivery can be achieved using simple saline or buffer-based formulations without inducing substantial adverse effects, such as severe immune response, in the subject. The availability of IT, e.g., as described herein, as a route for the administration of glucocerebrosidase proteins and/or nucleic acids represents a valuable tool for CNS targeting.

In certain embodiments of the present invention, a glucocerebrosidase protein or nucleic acid can be injected at any region surrounding the spinal canal. In some embodiments, an enzyme is injected into the lumbar area or the cisterna magna or intraventricularly into a cerebral ventricle space. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intraventricular Cerebral (ICV) delivery.

Various formulations for IT administration are known in the art. in some embodiments, formulations suitable for intrathecal delivery according to the present invention are not synthetic or artificial CSF. In some embodiments, formulations for intrathecal delivery have been formulated such that they are capable of stabilizing, or alternatively slowing or preventing the degradation, of one or more therapeutic agents formulated therewith. Suitable formulations for intrathecal administration may have various concentrations of therapeutic agent.

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord.

In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4). In other embodiments, an Ommaya reservoir is employed.

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before IT administration. In those cases, a suitable single dose volume may be e.g., more than about 3 ml, 4 ml, 5 ml, 6 ml, 7 ml, 8 ml, 9 ml, 10 ml, 15 ml, or 20 ml.

Accordingly, in certain embodiments, the present invention provides methods including a step of administering a glucocerebrosidase enzyme or nucleic acid intrathecally to a subject, e.g., a subject having PD.

In certain embodiments, the present invention provides methods that include a step of administering a glucocerebrosidase enzyme or nucleic acid by direct intracranial administration (see, e.g., International Publication WO 2005/039643, which is hereby incorporated by reference). In various embodiments, direct intracranial injection may be to any portion of the brain described herein. In particular embodiments, direct intracranial injection may be, e.g., to one or more of the striatum or substantia nigra.

Combination Therapy

Glucocerebrosidase may be used in conjunction with one or more therapeutic agents that are not glucocerebrosidase. For instance, when glucocerebrosidase is used in the treatment of PD, it may be administered to the same patient as a drug known to treat PD or symptoms thereof. In particular, known agents used in the treatment of patients having PD include, without limitation, dopamine replacement therapies such as levodopa or carbidopa, dopamine agonists such as pramipexole, ropinerole, and bromocriptine, MAO-inhibitors such as seleglinc and rasagilene, Catechol O-methyltransferase (COMT) inhibitors such as entracapone and tolcapone, and various other compounds including, without limitation, any agent known in the art to treat one or more symptoms associated with PD, e.g., as described herein. An agent used in combination with glucocerebrosidase may be administered in a single therapeutic composition with glucocerebrosidase, at the same time as glucocerebrosidase in the form of a separate composition, or in a manner temporally distinct from the administration of glucocerebrosidase. Further, the administration regimen, e.g. timing and dosage, of glucocerebrosidase administration and that of any of one or more combination therapy agents may be determined independently and administered independently, while in certain circumstances dosages may be co-modulated, interdependent, co-administered, or have any other relationship known to those of skill in the art. It is contemplated that glucocerebrosidase combination therapies may demonstrate synergy between glucocerebrosidase and one or more combination agents or demonstrate greater-than-additive effects. A glucocerebrosidase may be administered in any effective amount as determined independently or as determined by the joint action of glucocerebrosidase and any of one or more combination therapy agents.

Methods of the present invention can also include increasing activation of the administered GBA polypeptides or any endogenous GBA by administering GBA-activating polypeptides, such as prosaposin (PS) and/or its derivatives, saposin A (SA), saposin B (SB), saposin C (SC), and saposin D (SD). Additional information regarding GBA activation is known in the art, e.g., in WO2007150064, which is herein incorporated by reference.

Kits

Kits of the present invention can include any combination of agents, compositions, components, reagents, administration devices or mechanisms, or other entities provided herein. For instance, a kit of the present invention may include a glucocerebrosidase protein or nucleic acid and one or more of a carrier composition, an administration device, and a combination therapy agent. In some instances, a glucocerebrosidase protein or nucleic acid will be provided in a pharmaceutical carrier or excipient and/or in a dosage form. Kits may further include a device or other entity to facilitate delivery, such as a syringe for injection or a tool that facilitates the delivery of therapeutic compositions to the brain, e.g., the substantia nigra. Kits may further include components require to activate a glucocerebrosidase protein or nucleic acid either in vitro prior to administration or after administration where the activating agent is administered to the same patient as the glucocerebrosidase protein or nucleic acid at the same time or at a different time. Any of the kits provided herein can be included in a container, pack, or dispenser together with instructions for administration.

EXAMPLES

The present examples are provided in support of the compositions and methods of the present invention. In particular, the below examples demonstrate that the administration of a glucocerebrosidase nucleic acid to an animal can treat PD or PD-like symptoms. The below examples support to the use of glucocerebrosidase nucleic acids in the treatment of PD in human subjects. The below examples demonstrate that glucocerebrosidase gene therapy is neuroprotective in α-synuclein based rodent models of Parkinson's disease.

Example 1

Glucocerebrosidase Gene Delivery Reduces Symptoms of PD

The present example demonstrates that GBA1 gene delivery reduces the number and size of insoluble α-synuclein aggregates in mice overexpressing human wild type α-synuclein. Some of the experiments described herein address whether overexpression of glucocerebrosidase activity could decrease levels of the oligomeric and aggregated forms of α-synuclein. To achieve overexpression of glucocerebrosidase (GBA1) in the striatum, substantia nigra and hippocampus, unilateral injections of either AAV-GBA1 or AAV-GFP control were delivered to 2-month old ASO mice (Panel A of FIG. 1 and Panel C of FIG. 1).

Glucocerebrosidase activity was quantified in the brain of ASO mice 3-months post AAV-injection. A 3-fold increase ($T_{1,7}$=5.53, p<0.05) in GBA1 activity was found (Panel B of FIG. 1). This corresponded to an increase in the protein levels of GBA1 in the ASO mice that received AAV-GBA1. Western blots revealed a significant increase in amount of GBA1 in the substantia nigra ($T_{1,7}$=4.033, p<0.05), striatum ($T_{1,7}$=2.60, p<0.05), and hippocampus ($T_{1,7}$=2.496, p<0.05).

Figure 2:
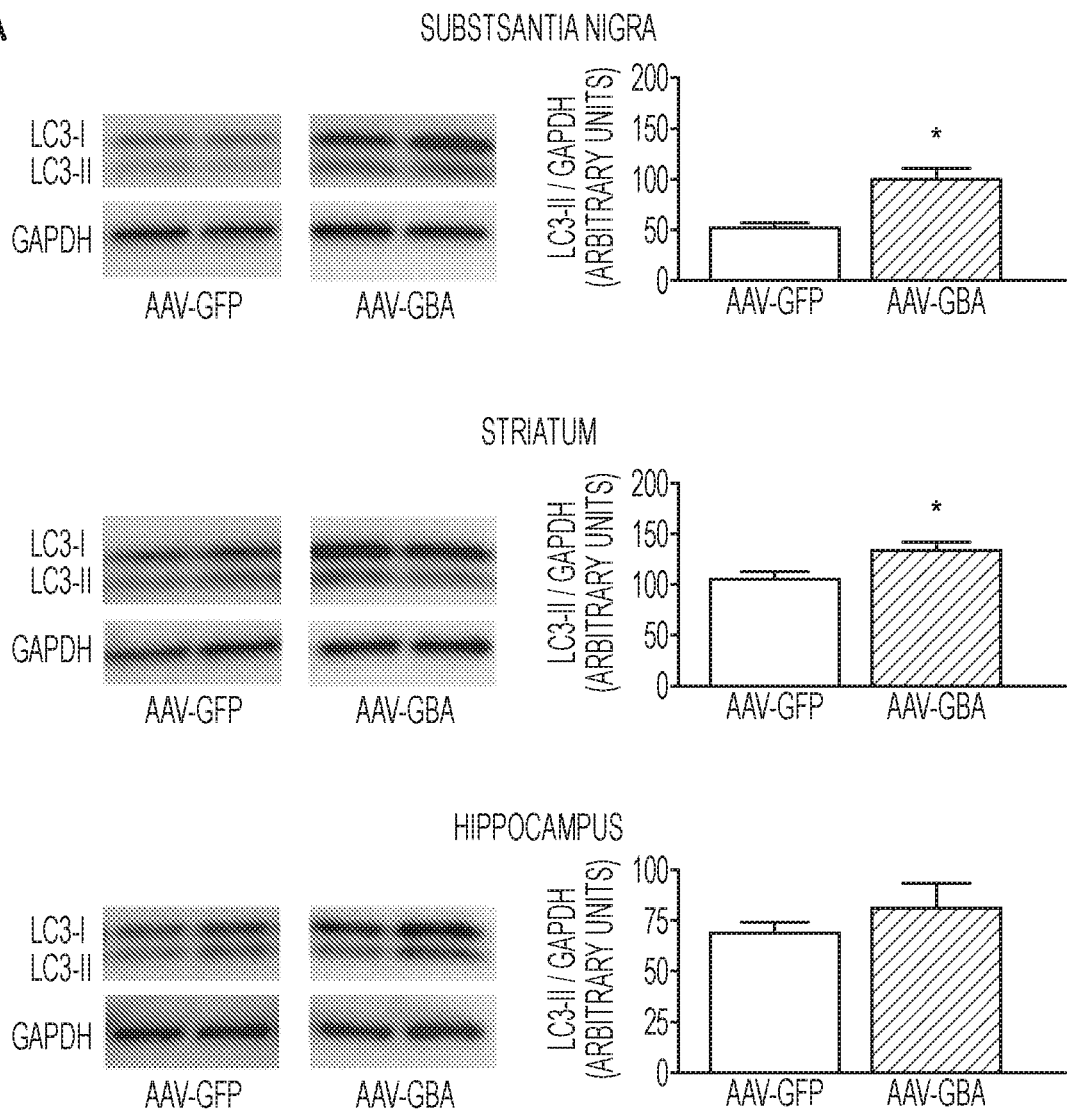
FIG. 2 is a figure including two panels: A and B.
Figure 2:
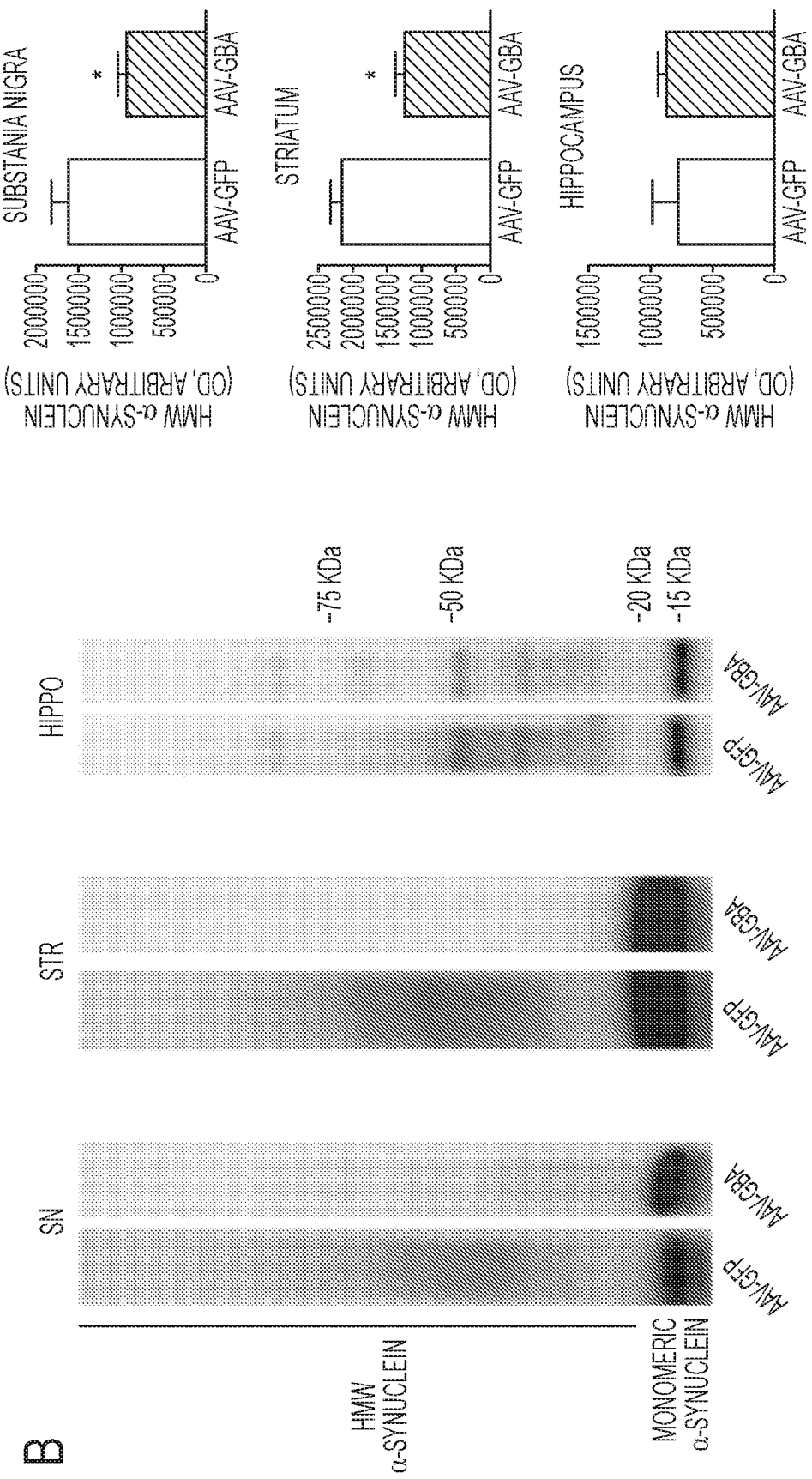

At 5-months of age, when ASO mice display modest pathology, AAV-GBA1 injection induced autophagosome formation (Panel A of FIG. 2), which was paralleled by a decrease in HMW α-synuclein (Panel B of FIG. 2). It was found that AAV-GBA1 delivery induced macroautophagy, as evidenced by the increase in LC3-II in the substantia nigra ($T_{2,4}$=3.80 p<0.05) and striatum ($T_{2,7}$=2.65, p<0.05) in comparison to AAV-GFP littermate-control mice (FIG. 2A). This induction coincided with a 40% reduction in BMW α-synuclein oligomeric species in the substantia nigra ($T_{2,6}$=3.18 p<0.05) and in the striatum ($T_{2,8}$=4.67 p<0.05) in comparison to AAV-GFP littermate-control mice (Panel B of FIG. 2). In contrast, levels of LC3-II and HMW α-synuclein remained unchanged in the hippocampus in comparison to AAV-GFP littermate-control mice (Panel A of FIG. 2 and Panel B of FIG. 2).

Figure 3:
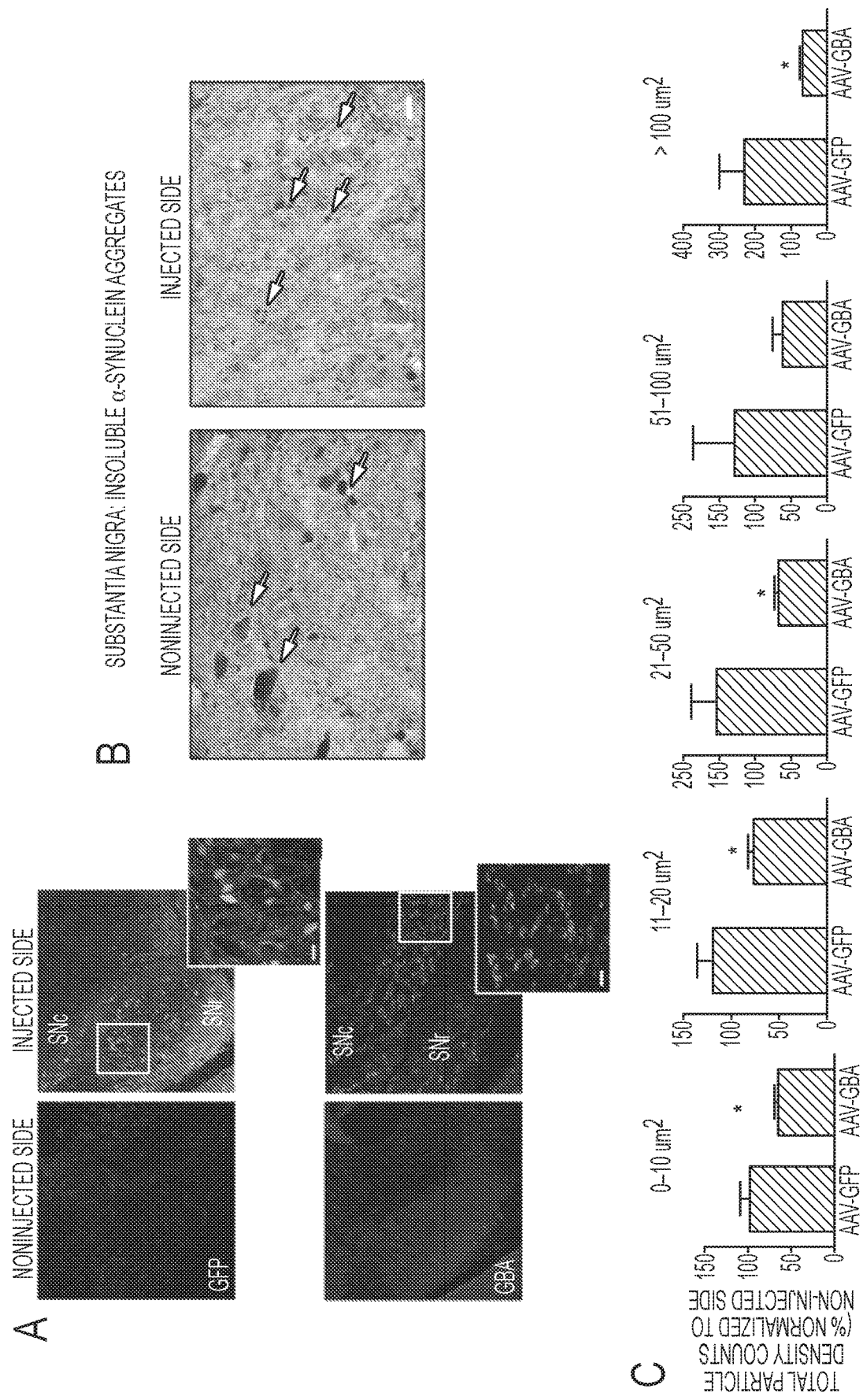
FIG. 3 is a figure including six panels: A, B, C, D, E, and F.
Figure 3:
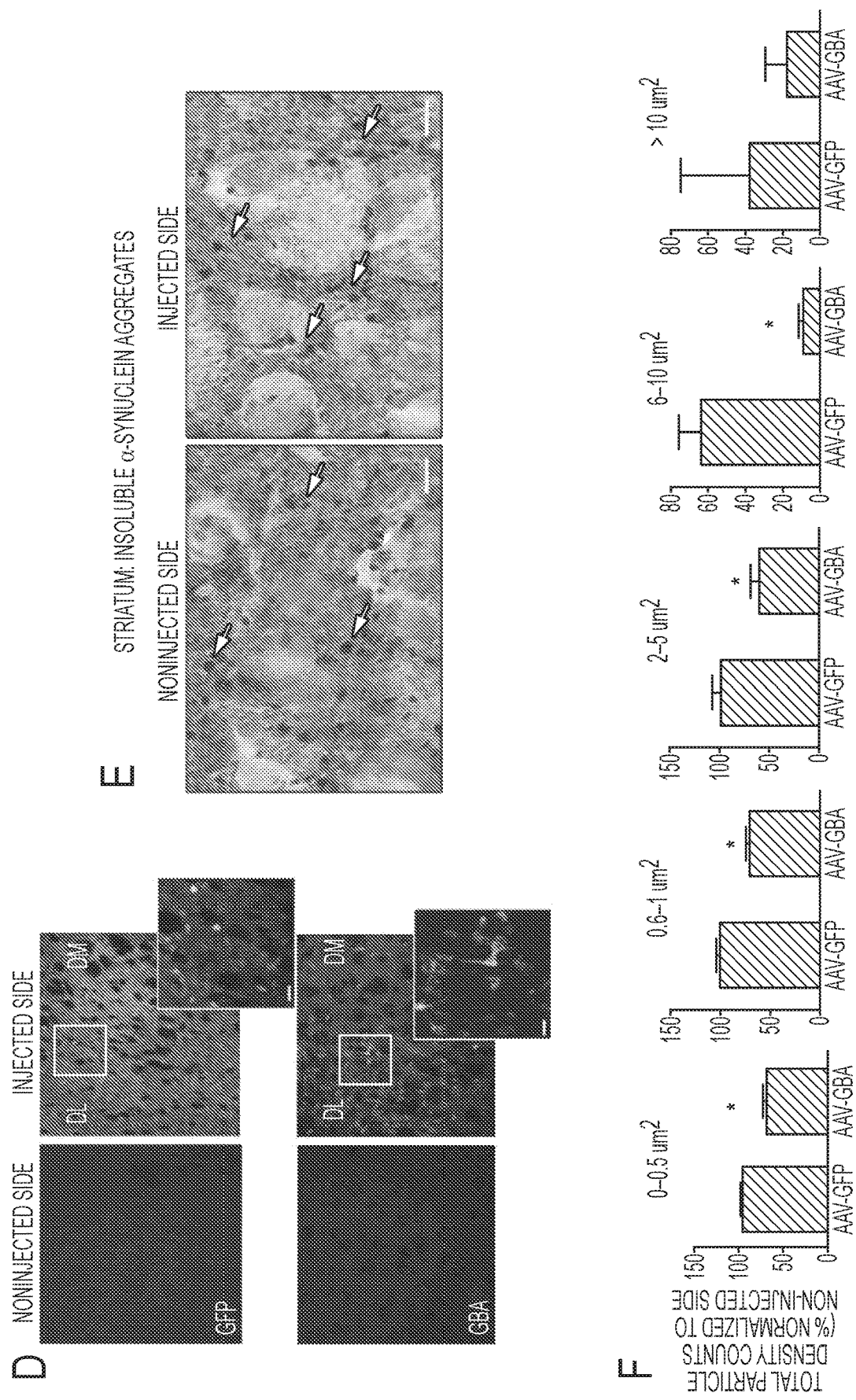

The present example also assessed whether GBA1 overexpression could decrease the number of insoluble α-synuclein aggregates. The number and size of proteinase-K resistant insoluble α-synuclein aggregates were quantified in ASO mice with severe pathology 8-months post AAV-GBA1 injection. Transgene expression of GBA was confirmed in the substantia nigra (Panel A of FIG. 3), striatum (Panel D of FIG. 3) and hippocampus by immunofluorescence. The proteinase-K resistant insoluble α-synuclein aggregates were quantified and normalized to the contra-lateral (non-injected) side. Overexpression of GBA1 reduced the number and size of the proteinase-K resistant insoluble α-synuclein aggregates, in comparison to AAV-GFP control ASO mice, 8-months post gene delivery. Specifically, AAV-GBA1 overexpression caused a reduction the number of α-synuclein aggregates in the substantia nigra of ASO mice between 0-10 μm$^2$ ($T_{2,7}$=2.73 p<0.05), 11-20 μm$^2$ ($T_{2,7}$=2.59 p<0.05), 21-50 μm$^2$ ($T_{2,7}$=2.61 p<0.05) and >100 μm$^2$ ($T_{2,7}$=2.73 p<0.05) compared to AAV-GFP injected littermate control ASO mice (Panel B of FIG. 3 and Panel C of FIG. 3). Consistent with the measurements of the number of α-synuclein aggregates in the substantia nigra, overexpression of GBA1 reduced the number of α-synuclein aggregates in the striatum between 0-0.5 μm$^2$ ($T_{2,8}$=5.05 p<0.05), 0.6-1 μm$^2$ ($T_{2,8}$=4.34 p<0.05), 2-5 μm$^2$ ($T_{2,8}$=2.85 p<0.05) and 6-10 μm$^2$ ($T_{2,7}$=5.06 p<0.05) compared to AAV-GFP injected littermate control ASO mice (Panel E of FIG. 3 and Panel F of FIG. 3). Consistent with data from the hippocampus 3-months post gene therapy, AAV-GBA1 did not decrease the number of insoluble aggregates in the hippocampus.

The data provided in this example demonstrates that AAV-GBA1 gene delivery induced autophagosome formation by inducing the expression of LC3-II, 3-months post AAV-injection. In addition, it demonstrates that GBA1 gene therapy reduced the amount of HMW α-synuclein oligomeric species 3-months post AAV-injection, which was consistent with the reduction in the number of proteinase-K resistant insoluble α-synuclein aggregates of all sizes, including larger aggregates (>100 μm$^2$).

Example 2

Glucocerebrosidase Gene Therapy is Neuroprotective

This example demonstrates the neuroprotective effects of overexpressing GBA1. In particular, the present example demonstrates that gene delivery of GBA1 protects nigrostriatal dopaminergic neurons from degeneration. GBA1 gene delivery was tested using a rat model of α-synucleinopathy, in which a 50% reduction in TH-positive neurons and accumulation of misfolded α-synuclein are observed, 24 weeks post-AAV injection. This differs from the model of Example 1, which manifests a progressive and widespread accumulation of insoluble α-synuclein but does not cause a loss of the TH-positive DA neurons in the substantia nigra.

Figure 4:
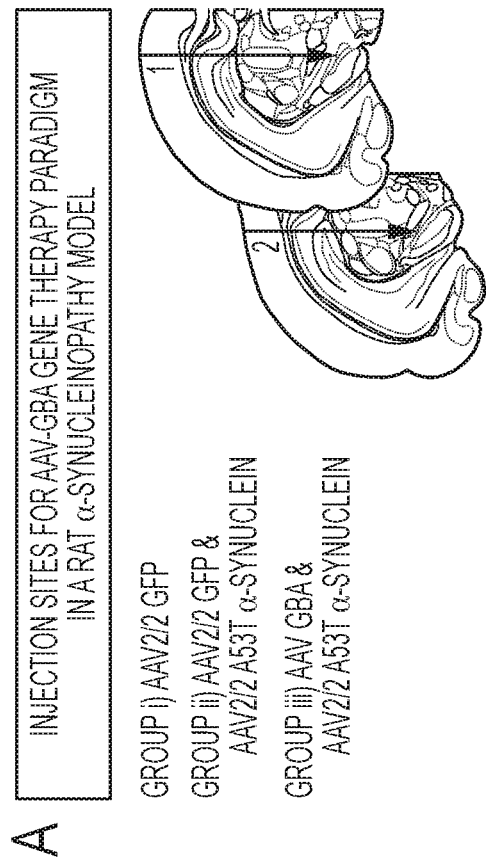
FIG. 4 is a figure including 4 panels: A, B, C, and D.
Figure 4:
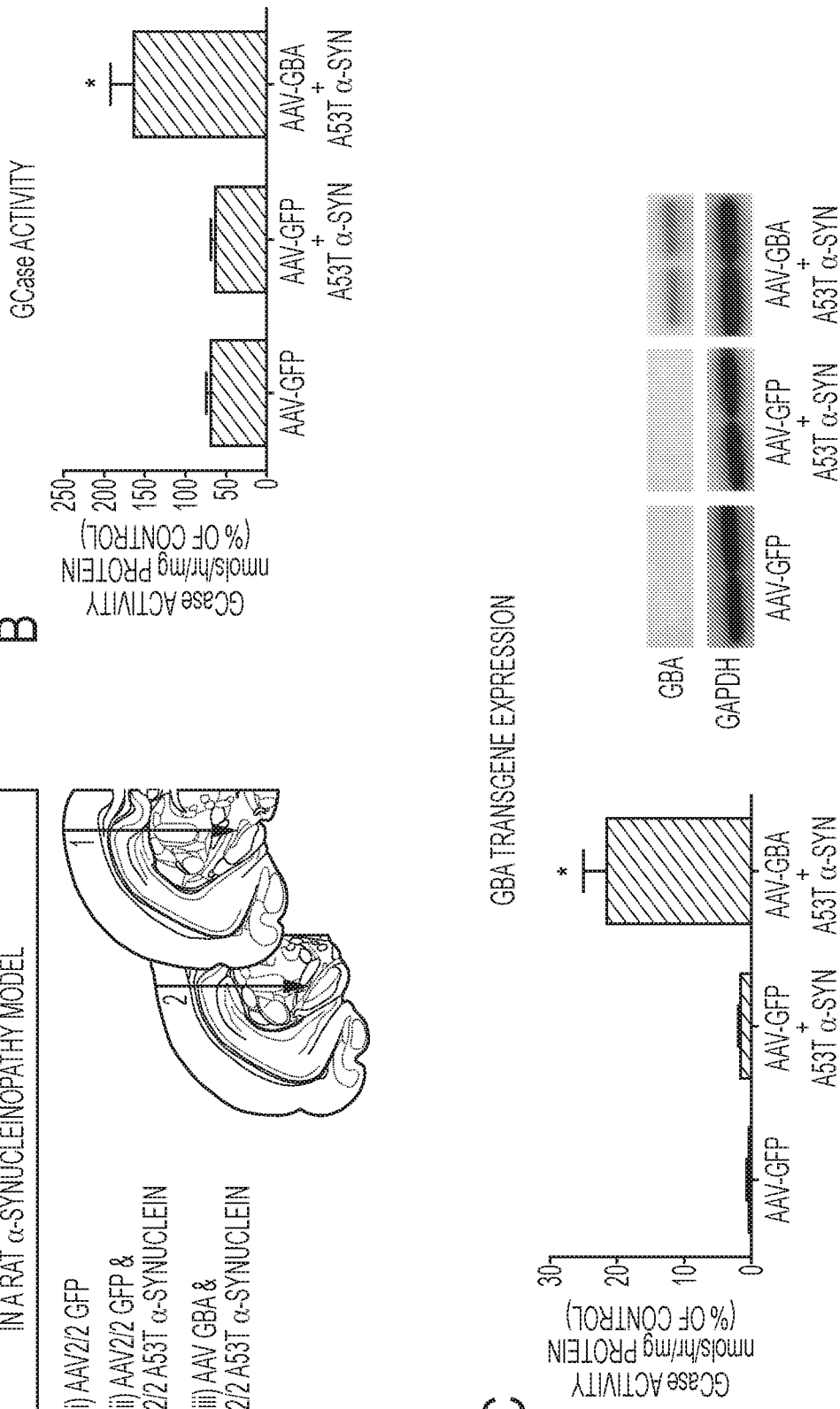
Figure 4:
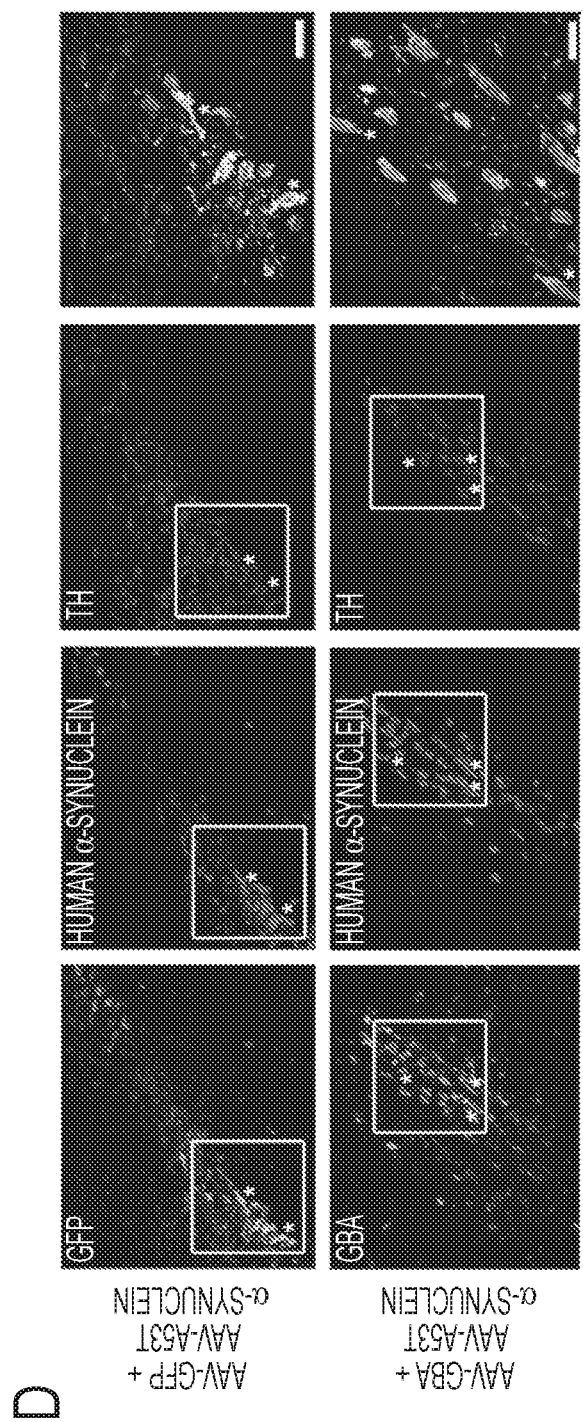

Naïve rats received an intra-nigral injections of either (1) AAV-GFP (control), (2) AAV-GFP+AAV-mutant A53T α-synuclein, or (3) AAV-GBA1+AAV-mutant A53T α-synuclein (Panel A of FIG. 4). GBA1 gene delivery caused an increase in Glucocerebrosidase activity ($F_{2,11}$=32.34, p<0.05) in the substantia nigra, as measured 8-weeks post AAV-injection (Panel B of FIG. 4). This increase in Glucocerebrosidase activity was paralleled by an increase in glucocerebrosidase protein levels ($F_{2,11}$=9.994, p<0.05) in the substantia nigra, 8-weeks post AAV-injection (Panel C of FIG. 4). At 24-weeks post-AAV injection, the transgene expressions of the viruses remained elevated in the DA neurons of the substantia nigra (Panel D of FIG. 4).

Figure 5:
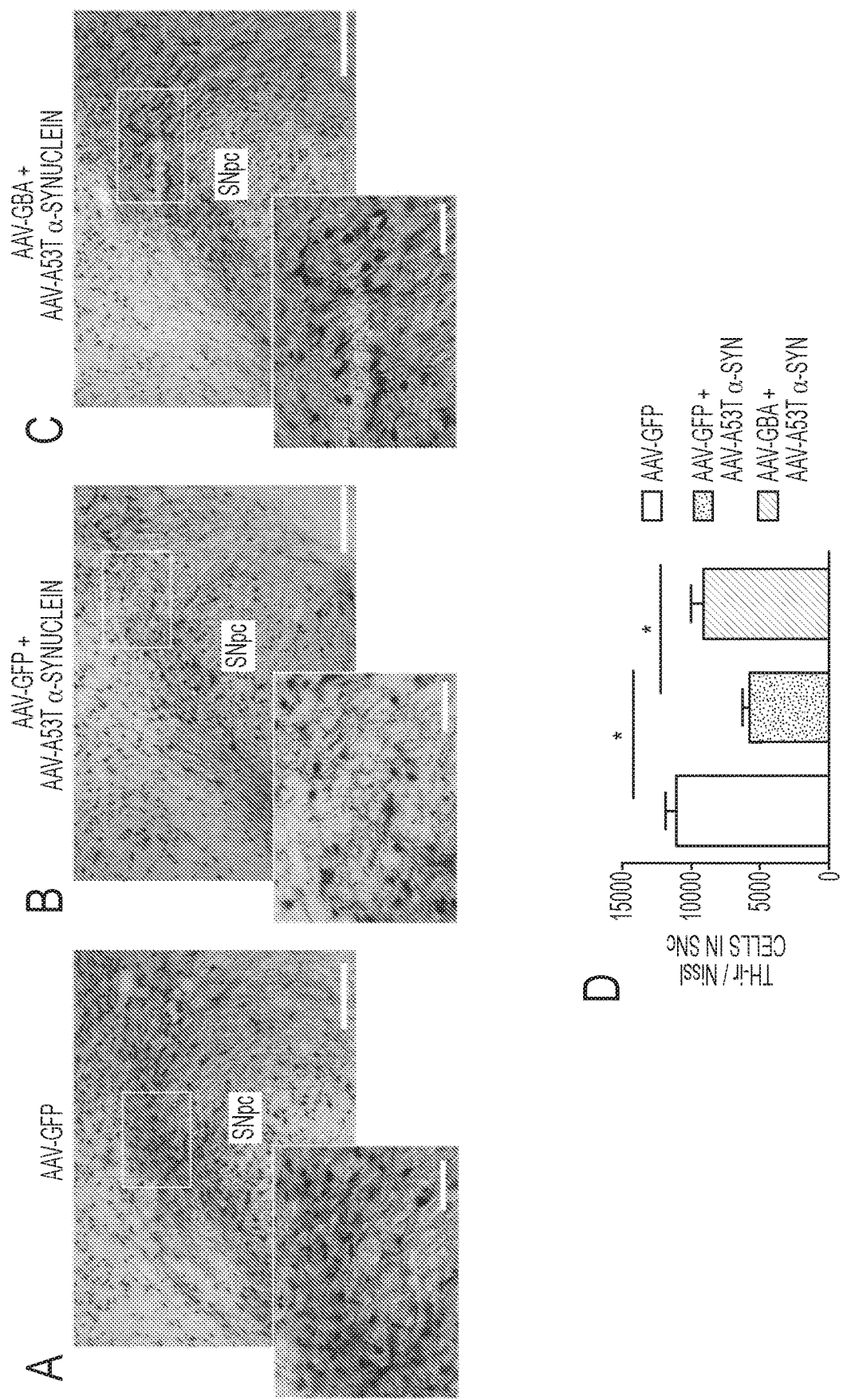
FIG. 5 is a figure including four panels: A, B, C, and D.

It was found that intra-nigral administration of AAV-mutant A53T α-synuclein caused a significant (50%; $F_{2,22}=7.89$, $p<0.05$) decrease in the number DA neurons compared to control rats injected with AAV-GFP (Panel A of FIG. 5, Panel B of FIG. 5, Panel C of FIG. 5, and Panel D of FIG. 5). Moreover, co-administration of AAV-GBA1 with AAV-mutant A53T α-synuclein prevented mutant A53T α-synuclein induced degeneration of the DA neurons of the substantia nigra pars compacta and was identical to AAV-GFP injected control rats (Panel A of FIG. 5, Panel B of FIG. 5, Panel C of FIG. 5, and Panel D of FIG. 5). Therefore, this data demonstrates that intra-nigral administration of AAV-GBA1 can rescue dopaminergic neurons from A53T α-synuclein-induced degeneration.

Example 3

Figure 6:
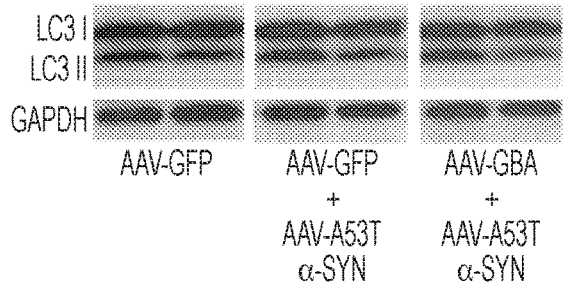
FIG. 6 is a figure including six panels: A, B, C, D, E, and F.
Figure 6:
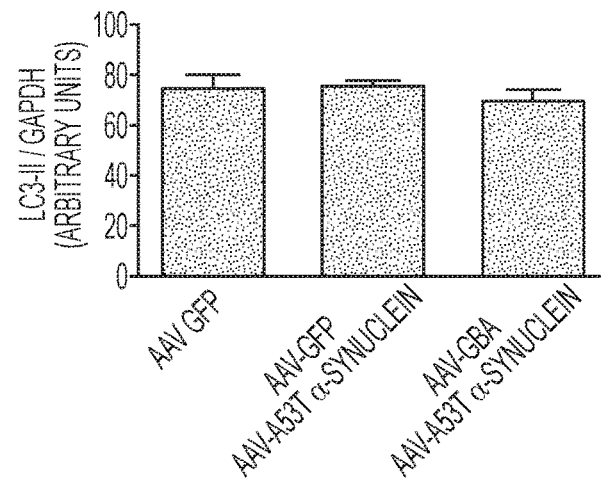
Figure 6:
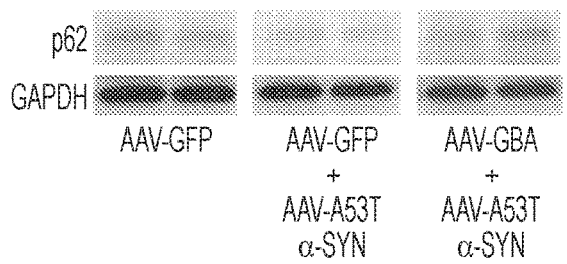
Figure 6:
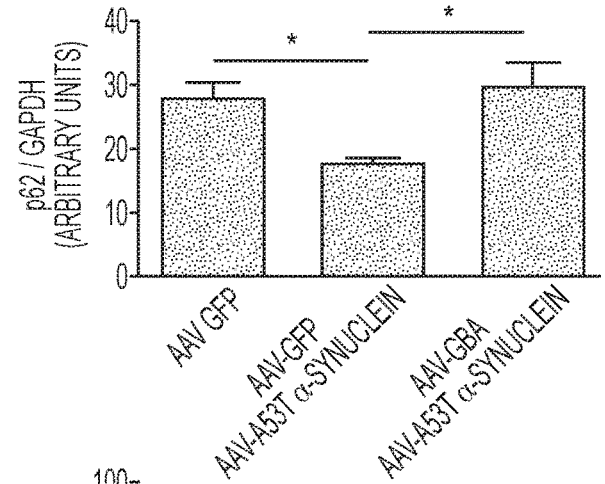
Figure 6:
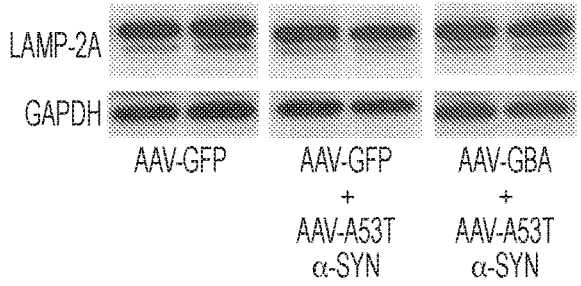
Figure 6:
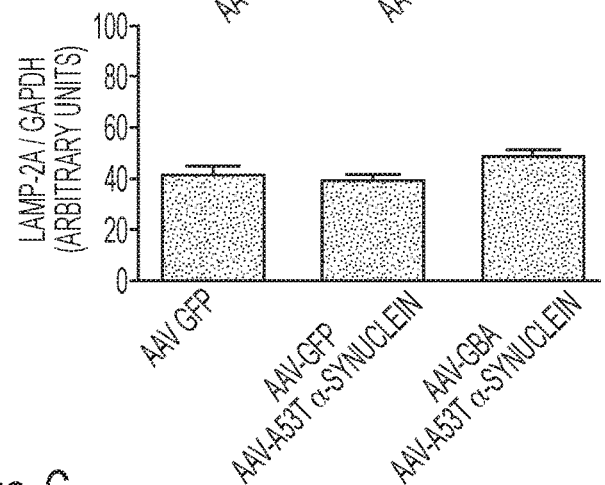
Figure 6:
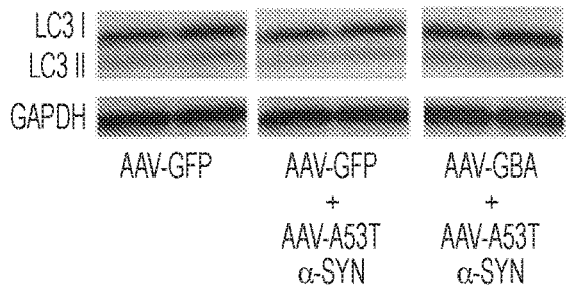
Figure 6:
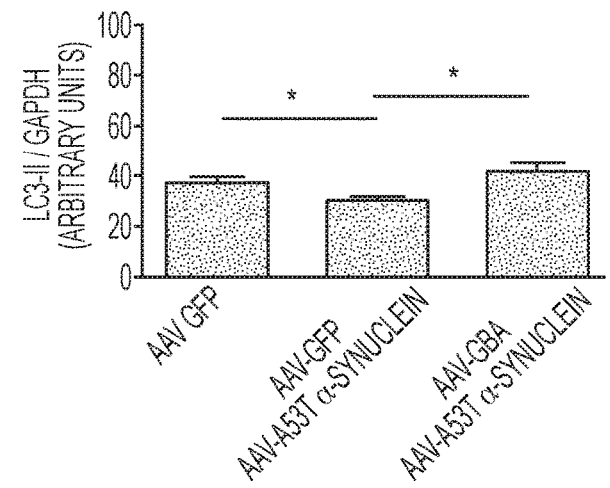
Figure 6:
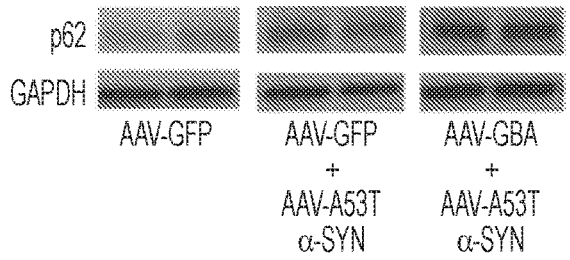
Figure 6:
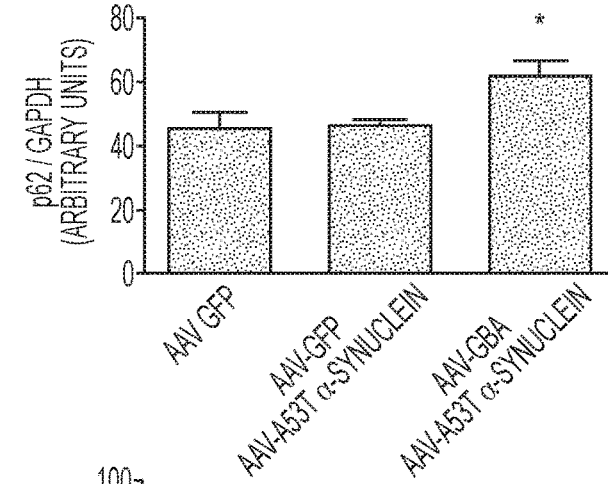
Figure 6:
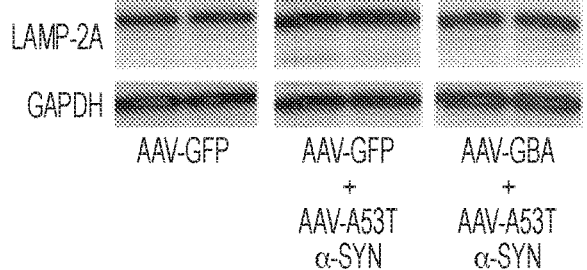
Figure 6:
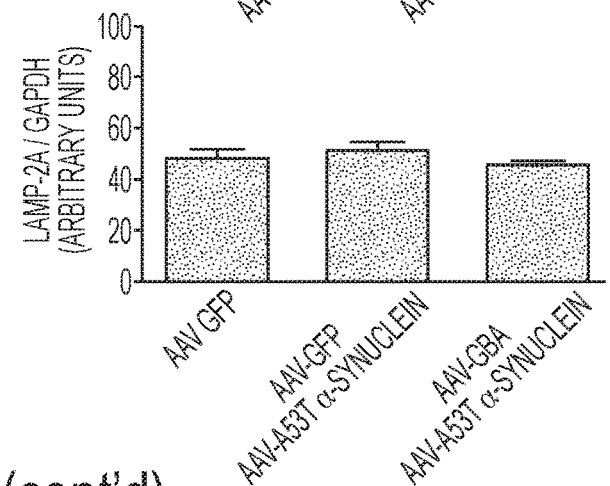

Overexpression of Glucocerebrosidase Restores Macroautophagy-Related Protein Expression This example demonstrates that overexpression of glucocerebrosidase induced macroautophagy and/or chaperone-mediated autophagy. Proteins involved in both pathways were explored at a pre-degenerative time point, 8-weeks post AAV-gene delivery. Specifically, Western blots were performed using total lysate from the substantia nigra and the striatum of naïve rats that received intra-nigral injections of (1) AAV-GFP (control), (2) AAV-GFP+AAV-mutant A53T α-synuclein or (3) AAV-GBA1+AAV-mutant A53T α-synuclein. At 8-weeks post gene delivery, levels of the lipidated form of LC3 (LC3-II) remained unchanged in the substantia nigra (Panel A of FIG. 6). However, levels of LC3-II significantly decreased ($F_{2,11}=8.15$, $p<0.05$) in the striatum of rats that received AAV-mutant A53T α-synuclein, which was restored by gene delivery of GBA1 (Panel B of FIG. 6). The ubiquitin-like protein p62 was decreased ($F_{2,10}=5.45$, $p<0.05$) in the substantia nigra of rats that received an intra-nigral injection AAV-mutant A53T α-synuclein, which was also restored by the administration of AAV-GBA1 (Panel C of FIG. 6). AAV-mutant A53T α-synuclein alone failed to induce a change in p62 in the striatum of rats; however, when co-administered with AAV-GBA1, p62 was significantly increased ($F_{2,12}=5.98$, $p<0.05$) in the striatum (Panel D of FIG. 6). The chaperone-mediated autophagy receptor LAMP-2A remained unchanged in the substantia nigra and striatum following a co-injection of AAV-mutant A53T α-synuclein and AAV-GBA1 (Panel E of FIG. 6 and Panel F of FIG. 6).

In view of at least the above examples, the present invention demonstrates at least that glucocerebrosidase can modulate α-synuclein accumulation using two rodent models of α-synucleinopathy. In a first model, which causes widespread accumulation of insoluble α-synuclein aggregates, the above examples demonstrate that overexpression of GBA1 induces macroautophagy and facilitates the removal of insoluble α-synuclein aggregates. In a second model, which causes selective degeneration of midbrain dopamine neurons, the above examples demonstrate that overexpression of GBA1 by gene therapy in neurons protects against mutant A53T α-synuclein induced neurodegeneration.

Example 4

Glucocerebrosidase Gene Delivery Protects Dopaminergic Neurons in the Substantia Against Neurodegeneration.

Intra-nigral injection of AAV-A53T α-synuclein over a 6-month period induces progressive degeneration of nigral DA neurons. In this context, the present examples demonstrate that mutant A53T α-synuclein decreased the conversion of LC3-I to LC3-II in the striatum, potentially disrupting the formation of autophagosomes and/or causing progressive accumulation of swollen and bulging axons and/or causing eventual loss of DA neurons from the nigrostriatal pathway. Mutant A53T α-synuclein was also associated with a decrease in the expression of ubiquitin-like protein p62 in the substantia nigra, which was restored by AAV-GBA1 gene delivery. These data indicate that overexpression of GBA1 by gene delivery can restore mutant A53T α-synuclein-induced disruption of macroautophagy and protect the DA neurons from mutant A53T α-synuclein induced neurodegeneration.

These findings demonstrate for the first time, to the present knowledge of the inventors, that high levels of glucocerebrosidase and/or glucocerebrosidase activity promotes survival of nigrostriatal DA neurons. These findings may link macroautophagy with GBA1-induced cell survival. Loss of glucocerebrosidase activity may correspond to reduced beclin-1 (regulator of autophagy), reduced LAMP-2A (required for chaperone-mediated autophagy), increased oligomeric α-synuclein levels, and/or a decrease in ceramide. The present invention encompasses the therapeutic potential of delivering AAV-GBA1 to prevent dopaminergic cell loss.

Example 5

Glucocerebrosidase Gene Delivery Enhances Lysosomal Activity and Improves α-Synuclein Clearance in Mice Glucocerebrosidase, as well as several other autophagy-lysosomal related proteins including TFEB, ATP13A2 and LAMP2A, are all downregulated in dopaminergic neurons of sporadic PD patients. Using a transgenic mouse model that causes global overexpression of human wild type α-synuclein, the present example demonstrates that overexpression of human wild type GBA1 by gene delivery stimulates the conversion of LC3-I to its lipidated form LC3-II in the substantia nigra and striatum. This increase in LC3-II coincided with a reduction in the number of insoluble α-synuclein aggregates, including larger aggregates, comparable to the size of Lewy body inclusions in the substantia nigra. The present example demonstrates for the first time, to the present knowledge of the inventors, that overexpression of a lysosomal hydrolase can initiate the clearance of larger insoluble aggregates within the substantia nigra. The present examples also provide support for a role of macroautophagy in AAV-GBA1 induced clearance of α-synuclein. AAV-GBA1 gene delivery can reduce age-dependent accumulation of oligomeric and proteinase-K resistant insoluble α-synuclein aggregates.

Example 6

Glucocerebrosidase and Glucocerebrosidase Constructs

This example describes glucocerebrosidase and glucocerebrosidase constructs such as those used in the above examples.

For the preparation of recombinant adeno-associated virus preparation, e.g., for certain wild type and ASO mouse surgeries, AAV2/5-GBA1 vector containing the coding sequence for the human GBA1 gene and under the synapsin promoter was injected into various brain regions. The final titer for the vector encoding human GBA1 was $2.0 \times 10^{12}$ genome copies/ml and green fluorescent protein (GFP), 2.0×10$^{12}$. For certain rat surgeries AAV2/2-GBA1 and AAV2/2-A53T-α-synuclein vector containing the coding sequences for the human GBA1 gene and for the human α-synuclein gene, respectively, were injected into the SN. Both vectors were under the control of the synapsin promoter. The GBA1 plasmid was obtained from Origene and Virovek completed virus production. Details on the virus production for mutant A53T-α-synuclein is known in the art. The final titer for the vector encoding human GBA1 was 2.0×10$^{12}$ genome copies/ml and green fluorescent protein (GFP), 2.0×10$^{12}$.

The examples of the present invention included, where appropriate, optionally assaying glucocerebrosidase activity. Glucocerebrosidase activities were determined by methods generally in accordance with methods known in the art (see Sellos-Moura, M., et al. 2011 Journal of immunological methods 373, 45-53). In particular assays, mouse brain tissues (~5 mg) were homogenized in 300 µL of water. Samples were diluted in a 2 mg/mL BSA, citric acid sodium phosphate buffer (pH 5). 10 µL of sample was added to 75 µL of 10 mM 4-methylumbelliferyl-β-D-glucopyranoside (Sigma, USA) substrate. After incubation with the substrate for 60 minutes at 37° C., the reaction was terminated using 200 µL of stop solution (0.3 M glycine/0.2 M sodium carbonate, pH 10.7). Plates were read (Ex 360/Em 460) in a Molecular Devices SPECTRAmax plate reader using Softmax Pro software. Enzymatic activity was assessed from a 4-methylumbelliferyl (Sigma, USA) standard curve and normalized to protein content in each sample as determined using a BCA kit (Thermo Scientific Pierce, USA).

Example 7

Transgenic Animals and Surgeries

This example describes transgenic animals and surgeries such as those used in the above examples. Transgenic mice that overexpress human wild type α-synuclein (ASO) on the Thy-1 promoter and wild type (WT) littermate controls were bred. Male mice were used for experimental procedures. Female Sprague-Dawley rats approximately 280 grams (Charles River Laboratories) were used for certain neuroprotection experiments. Animals were housed in standard conditions in a dark/light cycle of 12 h, with ad libitum access to food and water. All animal procedures were performed in accordance with National Institute of Health guidelines and were approved by the Institutional Animal Care and Use Committee (IACUC) at McLean Hospital, Harvard Medical School.

For certain stereotaxic surgeries, stereotaxic coordinates for WT and ASO mice surgeries were obtained using a mouse atlas by Paxinos and Watson (1986). Before surgery, mice were anesthetized using Nembutol sodium (50 mg/kg). The mice were placed in a stereotaxic frame (Stoelting), where a 10 µl Hamilton Syringe and 31 gauge needle was used as a delivery system. Two injection sites into the striatum were achieved using the following coordinates: anteroposterior (AP): +1.4, +0.1 mm, mediolateral (ML): −1.5, −2.0 mm, and dorsoventral (DV): −2.5, −3.5 and −2.2 mm, all relative to bregma. Two injections into the hippocampus were achieved using the following coordinates: AP: −2.0, −3.2 mm, ML: −1.5, −3 mm, and DV: −1.5, −3.2 mm, all relative to bregma. A single injection into the SN was achieved using the following coordinates: AP: −3.2 mm, ML: −1.3 mm, and DV: −1.4 mm, all relative to bregma. Two microliters of either AAV-GFP or AAV-GBA1 were injected unilateral at a rate of 1 µl/min using a microinfusion pump (Stoelting), with a wait time of 2 minutes between injections.

Stereotaxic coordinates for certain rat surgeries were obtained using a rat atlas by Paxinos and Watson (1986). Before surgery, rats were anesthetized using xylazine and ketamine (3 mg/kg and 60 mg/kg, respectively). The rats were placed in a stereotaxic frame (Stoelting), where a 10 µl Hamilton Syringe and 31 gauge needle was used as a delivery system. Two injections into the SN were achieved using the following coordinates: AP: −4.8, −5.5 mm, ML: −2.1, −1.9 mm, and DV: −7.1, −7.0 mm, all relative to bregma. Toothbar was set at −3.3 mm. Two microliters of AAV-GFP or AAV-GBA1 were injected unilateral at a rate of 0.5 µl/min using a microinfusion pump (stoelting), with a wait time of 5 minutes between injections.

Example 8

Antibodies, Staining, Sampling, and Other Analyses

The primary antibodies used in certain assays or experiments of the present examples included one or more of chicken anti-GFP (Ayes, 1:1000), mouse anti-GBA1 (Abcam, 1:1000), rabbit anti-LC3 (Millipore, 1:500), mouse anti-α-synuclein (BD Transduction, 1:1000), rabbit anti-LAMP-2A (Invitrogen, 1:200), rabbit anti-p62 (Cell Signaling, 1:200) and chicken anti-GAPDH (Millipore, 1:5000), anti-rabbit TH (Pelfreeze, 1:300). Horseradish peroxidase-conjugated goat anti-chicken, anti-rabbit, anti-mouse (all Jackson ImmunoResearch, 1:10,000) were used, in various assays or experiments, for Western blot analysis. Donkey biotin-conjugated anti-rabbit (Jackson ImmunoResearch, 1:500) was used for brightfield microscopy.

For immunohistochemical analyses, animals were terminally anaesthetized with sodium pentobarbital and perfused transcardially with 25 ml phosphate buffered 0.9% saline (PBS) followed by 100 ml of 4% paraformaldehyde in phosphate buffer. Brains were removed and post-fixed in 4% paraformaldehyde for 4 h before placing them 25% sucrose. Coronal sections were then cut; 40 µm thick, on a sledge microtome and stored in antifreeze at −20° C. until use. For confocal microscopy, sections were blocked with 10% normal serum and incubated with primary antibodies at 4° C. overnight, mounted using Vecatshield (Vector Laboratories) and visualized using a Ziess LSM 510 microscope.

Insoluble α-synuclein aggregates were, in some instances, stained and quantified. To visualize insoluble α-synuclein aggregates, tissue sections were pre-mounted on gelatin-coated slides and incubated with proteinase-K solution (10 µg/ml; Promega) for 20-30 minutes at 37° C. Endogenous peroxidases were then quenched in 3% hydrogen peroxide for 7 min and placed in a blocking solution (Vectashield MOM kit) for 1 hr at room temperature. Tissue sections were then incubated with anti-α-synuclein (1:1000; BD Transduction) overnight at 4° C. using the primary antibody diluent (Vectashield MOM kit), Sections were incubated with anti-mouse biotinylated secondary antibody (1:200) for 1 hr at RT and visualized using a standard peroxidase-based method (Vectastain Elite, ABC kit, Vector Laboratories, Burlingame Calif., USA) and the chromogen, 3,3'-diaminobenzidine (Sigma). Insoluble α-synuclein aggregates were quantified using the threshold function in Image J.

In certain instances, to quantify the number of DA neurons in the SNc, every 12$^{th}$-section was collected. Free-floating tissue sections were rinsed in PBS before endogenous peroxidases were quenched in 3% hydrogen peroxide for 7 min. After rinsing, the sections were incubated in 0.1%

Triton X-100 in PBS containing 10% normal serum. Tissue sections were then incubated with anti-TH overnight at 4° C. After washing in PBS, sections were incubated in biotinylated secondary antibody (1:200) and visualized using a standard peroxidase-based method (Vectastain Elite, ABC kit, Vector Laboratories, Burlingame Calif., USA) and the chromogen, 3,3'-diaminobenzidine (Sigma) and counter stained with Nissl. A blinded investigator counted the number of neurons using nonbiased stereology using the optical fractionator method at 20× from MBF Bioscience (Stereo-investigator 7) and the following parameters: A 150 μm×150 μm counting frame and 200×200 μm grid. One-way ANVOA statistical analyses were preformed followed by Bonferroni post hoc test. All analyses were conducted using GraphPad Prism (Version 5.0) (GraphPad Software, Inc). Statistical significance was determined at the alpha level of 0.05.

For Western blotting, as used in certain assays or experiments described herein, mice and rats were terminally anesthetized and perfused transcardially with heparinized saline (0.1% heparin in 0.9% saline) and brains were cut with the use of a tissue chopper at 750 μm and 1 mm, respectively. Tissue samples were homogenized in ice cold buffer containing: 300 mM sucrose in TE buffer (Bio-Rad). Phosphatase inhibitors I and II (1:100) and proteinase inhibitors (1:100) (Thermo Halt proteinase inhibitor single use cocktail) and EDTA were then added. Tissues were homogenized for 15 seconds and sonicated in with three short pulses. 20 μg of protein were loaded into the Criterion precast 4-12.5% SDS polyacrylamide gel system (Bio-Rad). The proteins were then transferred to PVDF membranes. Membranes were washed in Tris-buffered saline containing 0.1% Tween 20 (TBS-T) and blocked in 5% milk for 1 hr at room temperature prior to incubation with desired primary antibodies overnight at 4° C. The membranes were probed following the desired primary antibody. After washing in TBS-T, HRP-conjugated secondary antibodies were applied for 1 hr at room temperature. Blots were treated with ECL-Plus (Amersham Biosciences) and exposed using CHEMIDOC™ XRS with image LAB' software. Optical density analysis (NIH image) was used to determine the relative abundance of each protein of interest.

In various assays or experiments described herein, unpaired student's t-test analysis was used to compare sporadic PD-patients and age-matched control patients. 2-way ANOVA with Bonferroni post-hoc tests were also used in certain assays or experiments to compare both ASO and WT mice at different ages. Various analyses were conducted using GraphPad Prism (Version 5.0) (GraphPad Software, Inc). In various instances, statistical significance was determined at the alpha level of 0.05.

Other Embodiments

While a number of embodiments of this invention are described herein, the present disclosure and examples may be altered to provide other methods and compositions of this invention. Therefore, it will be appreciated that the scope of this invention is to be defined by the appended claims in addition to the specific embodiments that have been represented by way of example. All references cited herein are hereby incorporated by reference.

What is claimed is:

1. A method of treating Parkinson's disease (PD), the method comprising delivering to the central nervous system (CNS) of a subject in need thereof a vector comprising a nucleic acid encoding a glucocerebrosidase protein, wherein the nucleic acid encoding the glucocerebrosidase protein is operably linked to a synapsin promoter, wherein the vector is an AAV2/5 vector, wherein the vector is administered by injection, and wherein the method decreases the size or amount of insoluble α-synuclein aggregates in one or more brain tissues relative to a control.

2. The method of claim 1, wherein the sequence of the nucleic acid has at least 90% identity to SEQ ID NO.: 1 or SEQ ID NO.: 2.

3. The method of claim 1, wherein the glucocerebrosidase protein comprises an amino acid sequence having at least 90% identity to SEQ ID NO.: 3, SEQ ID NO.: 4, or SEQ ID NO.: 5.

4. The method of claim 1, wherein the method increases the amount and/or activity of glucocerebrosidase protein in one or more brain tissues relative to a control.

5. The method of claim 1, wherein the method increases the amount of LC3-II in one or more brain tissues relative to a control.

6. The method of claim 1, wherein the method increases, relative to a control, the amount of any of one or more of beclin-1, LAMP-2A, and ceramide in one or more brain tissues.

7. The method of claim 1, wherein the method increases the amount or concentration of ubiquitin-like protein p62 in one or more brain tissues relative to a control.

8. The method of claim 1, wherein the method treats degeneration of neurons.

9. The method of claim 8, wherein the degeneration of neurons is degeneration of dopaminergic neurons.

10. The method of claim 8, wherein the treatment of the degeneration comprises a decrease, relative to a control, in the number or severity of one or more of swollen axons, bulging axons, and axons that are both swollen and bulging.

11. The method of claim 1, wherein the administration of the nucleic acid increases macroautophagy relative to a control.

12. A gene therapy vector for the treatment of Parkinson's disease, the gene therapy vector comprising a nucleic acid encoding a glucocerebrosidase protein operably linked to a synapsin promoter, wherein the vector is an AAV2/5 vector, characterized in that delivery of the vector to the central nervous system (CNS) of a subject suffering from Parkinson's disease (PD), wherein the vector is administered by injection, decreases the size or amount of insoluble α-synuclein aggregates in one or more brain tissues relative to a control.

13. The gene therapy vector of claim 12, wherein the nucleic acid comprises a nucleotide sequence having at least 90% identity to SEQ ID NO.: 1 or SEQ ID NO.: 2.

14. The gene therapy vector of claim 12, wherein the glucocerebrosidase protein comprises an amino acid sequence having at least 90% identity to SEQ ID NO.: 3, SEQ ID NO.: 4, or SEQ ID NO.: 5.

* * * * *

SEQUENCE LISTING

```
<160> NUMBER OF SEQ ID NOS: 5

<210> SEQ ID NO 1
<211> LENGTH: 8850
<212> TYPE: DNA
<213> ORGANISM: Homo sapiens

<400> SEQUENCE: 1
tctagaaaga cttcactgag atcatttaaa gaacaaaaag gatggctggg gtccagcgca      60
gtggctcatg cctgtaatcc cagcactttc ggataccaag gcagcagatc acctgaggtc     120
cagagtttca gaccagcctg gccaacatag tgaaacccca tctctactaa aaataaaaaa     180
attagctgag catgttggag ggcacctgta atcccagcta cttgggaggc tgaggcagga     240
gaatcactcg aacccaggag gtggaggttg cagtgagcca agatcacgcc actgcactcc     300
agcctgggca acagagtgag actctgtctc aaaaaacaac aacaacaaaa aatacaaaca     360
agagacaagt agttcccagg tgcctaccaa gtggtcaggc actgcactta cctcactgac     420
tgcagtaacc accctttgag gttgtggcat tgcctccatt ttccaggcaa ggaaatgggc     480
tgagagctgg gattagtcag gtcatgactg tgtgtgccac tcccgctaaa tctcatttga     540
tgtggttcat gaggccacac catggacagc ttcctccttg tgtccactga ggatatggct     600
ttgtacaaca ctttggtttt ttgaacgact ttacaaacct ccctgtcttg tgaggaagga     660
agaacagtta ttaccatctg catctgatga tgaaacaagg gacgctgcag aggagccgca     720
ctgaccactc cctccctcca gtcctgtcat cccactgcca gtgtcccacc ctcttgtgcc     780
ctgcacttca ctggctaata accccccctca ctttttcctc tgtgaagcca tcctggataa     840
ttccccaccc acgaatggtc cctcctcatc tcagagagct ctccatgcac acctgttacc     900
```

```
gtttctgtct ttatctgtaa atatctgtgt gtctgacttc catgcctcac acacctctat    960
agggcaaaga ctgtcttaaa catcttggta gtgtcagtat tttgcacagt gaagtttttt   1020
ttttttaaatt atatcagctt tatttgtacc tttttgacat ttctatcaaa aaagaagtgt  1080
gcctgctgtg gttcccatcc tctgggattt aggagcctct accccattct ccatgcaaat   1140
ctgtgttcta ggctcttcct aaagttgtca cccatacatg ccctccagag ttttataggg   1200
catataatcg taacagatga gaggaagcca attgcccttt agaaatatgg ctgtgattgc   1260
ctcacttcct gtgtcatgtg acgctcctag tcatcacatg acccatccac atcgggaagc   1320
cggaattact tgcagggcta acctagtgcc tatagctaag gcaggtacct gcatccttgt   1380
ttttgtttag tggatcctct atccttcaga gactctggaa cccctgtggt cttctcttca   1440
tctaatgacc ctgaggggat ggagtttca agtccttcca gagaggtaag agagagagct   1500
cccaatcagc attgtcacag tgcttctgga atcctggcac tggaatttaa tgaatgacag   1560
actctctttg aatccagggc catcatggct ctttgagcaa ggcacagatg gagggagggg   1620
tcgaagttga aatgggtggg aagagtggtg gggagcatcc tgatttgggg tgggcagaga   1680
gttgtcatca gaagggttgc agggagagct gcacccaggt ttctgtgggc cttgtcctaa   1740
tgaatgtggg agaccgggcc atgggcaccc aaaggcagct aagccctgcc caggagagta   1800
gttgagcggt ggagagggc ttgcttttca gtcattcctc attctgtcct caggaatgtc    1860
ccaagccttt gagtagggta agcatcatgg ctggcagcct cacaggattg cttctacttc   1920
aggcagtgtc gtgggcatca ggtgagtgag tcaaggcagt ggggaggtag cacagagcct   1980
cccttctgcc tcatagtcct ttggtagcct tccagtaagc tggtggtaga cttttagtag   2040
gtgctcaata aatccttttg agtgactgag accaacttg gggtgaggat tttgtttttt    2100
ttcttttgaa acagagtctt actctgttgc ctgggctgga gtgcagtggt gcaattttgg   2160
ctcattccaa cctctgcctc ccagattcaa gcgattctct tgcttcagct tcccaggtag   2220
ctgggattac aggcggccac cactacgccc agctaatttt tgtatttta gtagagacgg    2280
ggtttcacca tgctggcaag gcaggtctca aactcctcac ctcaggtgat ccgcccacct   2340
cggcctccta aagtgctagg attacaggtg tgagcccctg cgcccggcca aggggtgagg   2400
aattttgaaa ccgtgttcag tctctcctag cagatgtgtc cattctccat gtcttcatca   2460
gacctcactc tgcttgtact ccctcccctcc caggtgcccg cccctgcatc cctaaaagct   2520
tcggctacag ctcggtggtg tgtgtctgca atgccacata ctgtgactcc tttgaccccc   2580
cgaccttttcc tgcccttggt accttcagcc gctatgagag tacacgcagt gggcgacgga   2640
tggagctgag tatggggccc atccaggcta atcacgggg cacaggtaac cattacaccc    2700
ctcacccct gggccaggct gggtcctcct agaggtaaat ggtgtcagtg atcaccatgg    2760
agtttcccgc tgggtactga taccttatt ccctgtggat gtcctcaggc ctgctactga    2820
ccctgcagcc agaacagaag ttccagaaag tgaagggatt tggagggcc atgacagatg    2880
ctgctgctct caacatcctt gccctgtcac ccctgccca aaatttgcta cttaaatcgt    2940
acttctctga agaaggtgag gaggaagggg acaagatgac atagagccat tgaaactttt   3000
cgttttctt ttctttttt aaattttt tgaggcagaa tctcactctg cccattctgt       3060
cggcgagaca ggagtgcagt ggtgtgatct cccctcacag caacctctgc ctcccaggct   3120
atagtgattc tcctgcctca gcctcctgag tagctggaat tataggcgtg cgccactacc   3180
acctggctaa ttttttgtatt tttagtagag acagggtttc atcatgttga ccaggctagt   3240
```

-continued

```
cttaaactcc tgacctcaaa tgatatacct gccttggcct cccgaagtgc tggaattaca    3300
agtgtgagcc accgagccca gcagacactt ttcttttttc tttttttttt tttgagacag    3360
agtctcgcac tgtcacccag gctggagtgc agtggcacaa tctcagctca ctgcaacctc    3420
cacctcccgg gttcaggtga ttctcctgtc tcagcctctc gagtacctgg gattacaggt    3480
gcctgccacc acgcccggct aattttttgt attttttagta gagacagggt ttcactatgt    3540
tggccaggat gattgcgaac tcctgacctc gtgatctgcc cacatcggcc tcccaaagtg    3600
ctgggattac atgcgtgagc cactgacact tttctttgcc ctttctttgg accctgactt    3660
ctgcccatcc ctgacatttg gttcctgttt taatgccctg tgaaataaga tttcgccgcc    3720
tatcatctgc taactgctac ggactcaggc tcagaaaggc ctgcgcttca cccaggtgcc    3780
agcctccaca ggttccaacc caggagccca agttcccttt ggccctgact cagacactat    3840
taggactggc aagtgataag cagagtccca tactctccta ttgactcgga ctaccatatc    3900
ttgatcatcc ttttctgtag aatcggata taacatcatc cgggtaccca tggccagctg    3960
tgacttctcc atccgcacct acaccctatgc agacacccct gatgatttcc agttgcacaa    4020
cttcagcctc ccagaggaag ataccaagct caaggtaggc attctagctt tttcaggccc    4080
tgagggccct gatgtctggg ggttgagaaa ctgtagggta ggtctgcttg tacagacatt    4140
ttgtcccctg ctgttttgtc ctgggggtgg gagggtggag ctaatggct gaaccggatg    4200 cactggttgg gctagtatgt gttccaactc tgggtgcttc tctcttcact acctttgtct    4260 ctagatacc ctgattcacc gagccctgca gttggcccag cgtcccgttt cactccttgc    4320
cagcccctgg acatcaccca cttggctcaa gaccaatgga gcggtgaatg ggaaggggtc    4380
actcaaggga cagcccggag acatctacca ccagacctgg gccagatact ttgtgaagta    4440
agggatcagc aaggatgtgg gatcaggact ggcctcccat ttagccatgc tgatctgtgt    4500
cccaaccctc aacctagttc cacttccaga tctgcctgtc ctcagctcac ctttctacct    4560
tctgggcctt tcagccttgg gcctgtcaat cttgcccact ccatcaggct tcctgttctc    4620
tcggtctggc ccactttctt tttatttttc ttcttttttt ttttttgag aaggagtctc    4680 tctctctgtc acccaggctg gagtgctgtg gcgccatctt cactcactgt aacctctgcc    4740
tcctgagttc aagcaattct cctgcctcag ccttccaagt agctgggatt ataggcgcct    4800
gccaccaggc ccagctgatt tttctatttt tagtagagac ggggtttcgc caggctgttc    4860
tcgaactcct gaactcaagt gatccacctg cctcggcttc ccaaagtgct gggattacag    4920
gtgtgagcca ccacacccag ctggtctggt ccactttctt ggccggatca ttcatgacct    4980
ttctcttgcc aggttcctgg atgcctatgc tgagcacaag ttacagttct gggcagtgac    5040
agctgaaaat gagccttctg ctgggctgtt gagtggatac ccttccagt gcctgggctt    5100 cacccctgaa catcagcgag acttcattgc ccgtgaccta ggtcctaccc tcgccaacag    5160
tactcaccac aatgtccgcc tactcatgct ggatgaccaa cgcttgctgc tgccccactg    5220
ggcaaaggtg gtaaggcctg gacctccatg gtgctccagt gaccttcaaa tccagcatcc    5280
aaatgactgg ctcccaaaact tagagcgatt tctctaccca actatggatt cctagagcac    5340
cattcccctg gacctccagg gtgccatgga tcccacagtt gtcgcttgaa accttttctag   5400 gggctgggcg aggtggctca ctcatgcaaa cccagcactt gggaagccg aggcgggtga    5460 tcacctgagg tcaggagttt aagaccaccc tggccaacgt gttgaaaccc tgtgtctact    5520
aaaatacaaa aaaaaaaaat tatctgggca tgatggtggg tgtctgtaat cccagctact    5580
caggaggctg agaagggaga atcagttgaa cccgggagat ggtggttgcg gtgagccgag    5640
```

```
atcgcgccac tgcactccag cctgggaggc tgagcgagac tccatctcga aacaaaacaa    5700
aacaaaacta tctaggctgg gggtggtggt tcatgtatgt atgtgtatat acatatatat    5760
gtgtttatat gtatatatat atacacacac acacatacat acacacacat acacacacaa    5820
attagctggg tgtggcaccc gtgtagtccc agctactcag gaggctaatg tgggaggatc    5880
agttgaccct aggaagtcaa ggctgcagtg agtcgtgatt gcgccactgt actccagccc    5940
gagtgacaga gtgacatcct gtctcaaaaa caaaaaaaaa tctccccaaa cctctctagt    6000
tgcattcttc ccgtcaccca actccaggat tcctacaaca ggaactagaa gttccagaag    6060
cctgtgtgca aggtccagga tcagttgctc ttcctttgca ggtactgaca gacccagaag    6120
cagctaaata tgttcatggc attgctgtac attggtacct ggactttctg ctccagcca    6180
aagccaccct aggggagaca caccgcctgt tccccaacac catgctcttt gcctcagagg    6240
cctgtgtggg ctccaagttc tgggagcaga gtgtgcggct aggctcctgg gatcgaggga    6300
tgcagtacag ccacagcatc atcacggtaa gccaccccag tctcccttcc tgcaaagcag    6360
acctcagacc tcttactagt ttcaccaaag actgacagaa gcccttcctg tccagctttc    6420
cccagctagc ctgcccttt gagcaactct ggggaaccat gattccctat cttccctttc    6480
cttcacaggt ctgcacacct cattgcccct tttgcaacta ctgaggcact tgcagctgcc    6540
tcagacttct cagctcccct tgagatgcct ggatcttcac accccaact ccttagctac    6600
taaggaatgt gcccctcaca gggctgacct acccacagct gcctctccca catgtgaccc    6660
ttacctacac tctctgggga cccccagtgt tgagcctttg tctctttgcc tttgtcctta    6720
ccctagaacc tcctgtacca tgtggtcggc tggaccgact ggaaccttgc cctgaacccc    6780
gaaggaggac ccaattgggt gcgtaacttt gtcgacagtc ccatcattgt agacatcacc    6840
aaggacacgt tttacaaaca gcccatgttc taccaccttg ccacttcag gtgagtggag    6900
ggcgggcacc cccattccat accaggccta tcatctccta catcggatgg cttacatcac    6960
tctacaccac gagggagcag gaaggtgttc agggtggaac ctcggaagag gcacacccat    7020
ccccttttgc accatggagg caggaagtga ctaggtagca acagaaaacc ccaatgcctg    7080
aggctggact gcgatgcaga aaagcagggt cagtgcccag cagcatggct ccaggcctag    7140
agagccaggg cagagcctct gcaggagtta tggggtgggt ccgtgggtgg gtgacttctt    7200
agatgagggt ttcatgggag gtaccccgag ggactctgac catctgttcc acattcagc    7260
aagttcattc ctgagggctc ccagagagtg gggctggttg ccagtcagaa gaacgacctg    7320
gacgcagtgg cactgatgca tcccgatggc tctgctgttg tggtcgtgct aaaccggtga    7380
gggcaatggt gaggtctggg aagtgggctg aagacagcgt tgggggcctt ggcaggatca    7440
cactctcagc ttctcctccc tgctccctag ctcctctaag gatgtgcctc ttaccatcaa    7500
ggatcctgct gtgggcttcc tggagacaat ctcacctggc tactccattc acacctacct    7560
gtggcgtcgc cagtgatgga gcagatactc aaggaggcac tgggctcagc ctgggcatta    7620
aagggacaga gtcagctcac acgctgtctg tgactaaaga gggcacagca gggccagtgt    7680
gagcttacag cgacgtaagc ccaggggcaa tggtttgggt gactcacttt ccctctagg    7740
tggtgccagg ggctggaggc ccctagaaaa agatcagtaa gccccagtgt cccccagcc    7800
cccatgctta tgtgaacatg cgctgtgtgc tgcttgcttt ggaaactggg cctgggtcca    7860
ggcctagggt gagctcactg tccgtacaaa cacaagatca gggctgaggg taaggaaaag    7920
aagagactag gaaagctggg cccaaaactg gagactgttt gtctttcctg gagatgcaga    7980
```

```
actgggcccg tggagcagca gtgtcagcat cagggcggaa gccttaaagc agcagcgggt    8040
gtgcccaggc acccagatga ttcctatggc accagccagg aaaaatggca gctcttaaag    8100
gagaaaatgt ttgagcccag tcagtgtgag tggctttatt ctgggtggca gcaccccgtg    8160
tccggctgta ccaacaacga ggaggcacgg gggcctctgg aatgcatgag agtagaaaaa    8220
ccagtcttgg gagcgtgagg acaaatcatt cctcttcatc ctcctcagcc atgcccaggg    8280
tccgggtgcc tggggcccga gcaggcgttg cccgctggat ggagacaatg ccgctgagca    8340
aggcgtagcc caccatggct gccagtcctg ccagcacaga taggatctgg ttccggcgcc    8400
ggtatggctc ctcctcagtc tctgggcctg ctggtgtctg gcgttgcggt ggtacctcag    8460
ctgagggtca aggaaggaag gtgtgttagg agaactagtt cttggatccc tgcccactct    8520
ccccagggct gccctccca tctgccctt acctccatcc caggggaagt agagactgag    8580
aatgtgggta caataggcac agaggttgtg cagcccacgc aggtggacct gcagcttccc    8640
actgggcagc tttgcctgca gcagcagggc caagtagctg aagacgaagg cgtccaagga    8700
ggcagggctg gagcagagag agaagggtgg gatggaggag aaccactggg gtagaagggg    8760
taaagatgga gctggaggaa gagtcagcct tgggaggtgg gctctgggca gcaggcggcc    8820
accaggaagg acaggacaca cagttctaga                                     8850

<210> SEQ ID NO 2
<211> LENGTH: 2587
<212> TYPE: DNA
<213> ORGANISM: Homo sapiens
<220> FEATURE:
<221> NAME/KEY: modified_base
<222> LOCATION: (2318)..(2318)
<223> OTHER INFORMATION: a, c, t, g, unknown or other

<400> SEQUENCE: 2
ccattaggcc tatgaattat aagatacagt cactttaaaa tccactggaa ggctgaagag      60
tgagttaaac ctcttataat gaatatacag tgaaaccagt agaggcattt tatttagggt     120
tcctacaaga aagtgcttaa atagcatcga cgcctacatg ctacatcctg ttcagtctct     180
gcctctgtga tgcagttggc cagcaaatat cctccaagtc atcatttgca tagtgctagg     240
gataaaatga ggagcaatac caaatgctat acctgccctt atgggtctta tagtccaacg     300
ggagaaaaag atattataca ataatcacg gaaataaat agaaaacgca tccttgtttt     360
tgtttagtgg atcctctatc cttcagagac tctggaaccc ctgtggtctt ctcttcatct     420
aatgaccctg aggggatgga gttttcaagt ccttccagag aggaatgtcc caagcctttg     480
agtagggtaa gcatcatggc tggcagcctc acaggtttgc ttctacttca ggcagtgtcg     540
tgggcatcag gtgcccgccc ctgcatccct aaaagcttcg gctacagctc ggtggtgtgt     600
gtctgcaatg ccacatactg tgactccttt gacccccga cctttcctgc ccttggtacc     660
ttcagccgct atgagagtac acgcagtggg cgacggatgg agctgagtat ggggcccatc     720
caggctaatc acacgggcac aggcctgcta ctgaccctgc agccagaaca gaagttccag     780
aaagtgaagg gatttggagg ggccatgaca gatgctgctg ctctcaacat ccttgccctg     840 tcacccctg cccaaaattt gctacttaaa tcgtacttct ctgaagaagg aatcggatat     900
aacatcatcc gggtacccat ggccagctgt gacttctcca tccgcaccta cacctatgca     960
gacacccctg atgatttcca gttgcacaac ttcagcctcc cagaggaaga taccaagctc    1020
aagatacccc tgattcaccg agccctgcag ttggcccagc gtcccgtttc actccttgcc    1080
agcccctgga catcacccac ttggctcaag accaatggag cggtgaatgg gaagggtca    1140
```

```
ctcaagggac agcccggaga catctaccac cagacctggg ccagatactt tgtgaagttc    1200
ctggatgcct atgctgagca caagttacag ttctgggcag tgacagctga aaatgagcct    1260
tctgctgggc tgttgagtgg ataccccttc cagtgcctgg gcttcacccc tgaacatcag    1320
cgagacttca ttgcccgtga cctaggtcct accctcgcca acagtactca ccacaatgtc    1380
cgcctactca tgctggatga ccaacgcttg ctgctgcccc actgggcaaa ggtggtactg    1440
acagacccag aagcagctaa atatgttcat ggcattgctg tacattggta cctggacttt    1500
ctggctccag ccaaagccac cctaggggag acacaccgcc tgttcccaa caccatgctc     1560 tttgcctcag aggcctgtgt gggctccaag ttctgggagc agagtgtgcg gctaggctcc    1620
tgggatcgag ggatgcagta cagccacagc atcatcacga acctcctgta ccatgtggtc    1680
ggctggaccg actggaacct tgccctgaac cccgaaggag acccaattg ggtgcgtaac     1740 tttgtcgaca gtcccatcat tgtagacatc accaaggaca cgttttacaa acagcccatg    1800
ttctaccacc ttggccactt cagcaagttc attcctgagg ctcccagag agtggggctg     1860 gttgccagtc agaagaacga cctggacgca gtggcactga tgcatcccga tggctctgct    1920
gttgtggtcg tgctaaaccg ctcctctaag gatgtgcctc ttaccatcaa ggatcctgct    1980
gtgggcttcc tggagacaat ctcacctggc tactccattc acacctacct gtggcatcgc    2040
cagtgatgga gcagatactc aaggaggcac tgggctcagc ctgggcatta agggacaga    2100 gtcagctcac acgctgtctg tgactaaaga gggcacagca gggccagtgt gagcttacag    2160
cgacgtaagc ccaggggcaa tggtttgggt gactcacttt cccctctagg tggtgcccag    2220
ggctggaggc cctagaaaaa agatcagtaa gcccagtgt cccccagcc cccatgctta      2280 tgtgaacatg cgctgtgtgc tgcttgcttt ggaaactngc ctgggtccag gcctagggtg    2340
agctcactgt ccgtacaaac acaagatcag ggctgagggt aaggaaaaga agagactagg    2400
aaagctgggc ccaaaactgg agactgtttg tctttcctag agatgcagaa ctgggcccgt    2460
ggagcagcag tgtcagcatc agggcggaag ccttaaagca gcagcgggtg tgcccaggca    2520
cccagatgat tcctatggca ccagccagga aaaatggcag ctcttaaagg agaaaatgtt    2580
tgagccc                                                              2587
```

<210> SEQ ID NO 3
<211> LENGTH: 536
<212> TYPE: PRT
<213> ORGANISM: Homo sapiens

<400> SEQUENCE: 3

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110
```

```
Lys Phe Gln Lys Val Lys Gly Phe Gly Gly Ala Met Thr Asp Ala Ala
            115                 120                 125

Ala Leu Asn Ile Leu Ala Leu Ser Pro Pro Ala Gln Asn Leu Leu Leu
        130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
                180                 185                 190

Thr Lys Leu Lys Ile Pro Leu Ile His Arg Ala Leu Gln Leu Ala Gln
            195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
                260                 265                 270

Asn Glu Pro Ser Ala Gly Leu Leu Ser Gly Tyr Pro Phe Gln Cys Leu
            275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
    355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
    515                 520                 525
```

```
His Thr Tyr Leu Trp Arg Arg Gln
    530                 535

<210> SEQ ID NO 4
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
```

```
                    340                 345                 350
Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
        370                 375                 380

Leu Asn Pro Glu Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 5
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190
```

```
Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
        210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln
```